United States Patent
Pasternak et al.

(10) Patent No.: US 9,850,245 B2
(45) Date of Patent: Dec. 26, 2017

(54) INHIBITORS OF THE RENAL OUTER MEDULLARY POTASSIUM CHANNEL

(71) Applicants: Merck Sharp & Dohme Corp., Rahway, NJ (US); Alexander Pasternak, Kenilworth, NJ (US); Fa-Xiang Ding, Kenilworth, NJ (US); Shuzhi Dong, Kenilworth, NJ (US); Jinlong Jiang, Kenilworth, NJ (US); Haifeng Tang, Kenilworth, NJ (US); Xin Gu, Kenilworth, NJ (US); Reynalda K. DeJesus, Kenilworth, NJ (US); Jessica Frie, West Point, PA (US); Qinghong Fu, Plainsboro, NJ (US); Takao Suzuki, Shanghai (CN); Zhifa Pu, Shanghai (CN)

(72) Inventors: Alexander Pasternak, Princeton, NJ (US); Fa-Xiang Ding, Staten Island, NY (US); Shuzhi Dong, Plainsboro, NJ (US); Jinlong Jiang, Scotch Plains, NJ (US); Haifeng Tang, Metuchen, NJ (US); Xin Gu, Scotch Plains, NJ (US); Reynalda K. DeJesus, East Brunswick, NJ (US); Jessica Frie, Harleysville, PA (US); Qinghong Fu, Plainsboro, NJ (US); Takao Suzuki, Shanghai (CN); Zhifa Pu, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/505,277

(22) PCT Filed: Oct. 26, 2015

(86) PCT No.: PCT/US2015/057279
§ 371 (c)(1),
(2) Date: Feb. 21, 2017

(87) PCT Pub. No.: WO2016/069426
PCT Pub. Date: May 6, 2016

(65) Prior Publication Data
US 2017/0275283 A1 Sep. 28, 2017

(30) Foreign Application Priority Data
Oct. 31, 2014 (WO) ................ PCT/CN2014/089998

(51) Int. Cl.
| | |
|---|---|
| *C07D 471/10* | (2006.01) |
| *A61K 31/499* | (2006.01) |
| *C07D 498/10* | (2006.01) |
| *A61K 31/5386* | (2006.01) |
| *A61K 31/55* | (2006.01) |
| *A61K 31/435* | (2006.01) |
| *A61K 31/537* | (2006.01) |
| *C07D 498/20* | (2006.01) |
| *A61K 31/553* | (2006.01) |
| *A61K 45/06* | (2006.01) |

(52) U.S. Cl.
CPC .......... *C07D 471/10* (2013.01); *A61K 31/435* (2013.01); *A61K 31/499* (2013.01); *A61K 31/537* (2013.01); *A61K 31/5386* (2013.01); *A61K 31/55* (2013.01); *A61K 31/553* (2013.01); *A61K 45/06* (2013.01); *C07D 498/10* (2013.01); *C07D 498/20* (2013.01)

(58) Field of Classification Search
None
See application file for complete search history.

(56) References Cited

U.S. PATENT DOCUMENTS

| | | |
|---|---|---|
| 2006/0252797 A1 | 11/2006 | Kajino et al. |
| 2014/0031349 A1 | 1/2014 | Ding et al. |
| 2014/0235628 A1 | 8/2014 | Walsh et al. |

FOREIGN PATENT DOCUMENTS

| | | |
|---|---|---|
| WO | 2014015495 A1 | 1/2014 |
| WO | 2014150132 A1 | 9/2014 |
| WO | WO2016069426 A1 | 5/2016 |
| WO | WO2016065602 A1 | 6/2016 |

OTHER PUBLICATIONS

Bhave,G., Development of a selective small-molecule inhibitor Kir1.1, the renal outer medullary potassium channel, Mol. Pharmacol., 2011, 42-50, 79.
Fringuelli, F. et al., A Simple Procedure for the Synthesis of Labile Aryl Oxiranes by Epoxidation, Organic, Preparations and Procedures Int., 1989, p. 757-761, vol. 21, No. 6.
Hebert, S. C. et al., Molecular Diversity and Regulation of Renal Potassium Channels, Physiol Rev., 2005, p. 319-371, vol. 85.
Ho, K. et al., Cloning and expression of an inwardly rectifying ATP-regulated potassium channel, Nature, 1993, p. 31-38, vol. 362.
International Search Report and Written Opinion for PCT/US2015/057279 dated Jan. 14, 2016; 8 pages.
International Search Report of PCT/CN2014/089998 dated Jul. 29, 2015; pp. 16.
Ji, W. et al., Rare independent mutations in renal salt handling genes contribute to blood pressure variation, Nature Genetics, 2008, p. 592-599, vol. 40, No. 5.
Lerman, Lilach, O. et al., Animal Models of hypertension : An overview, J Lab Clin Med, 2005, p. 160-173, vol. 146, No. 3.

(Continued)

*Primary Examiner* — Heidi Reese
(74) *Attorney, Agent, or Firm* — Baerbel R. Brown; Catherine D. Fitch

(57) ABSTRACT

The present invention provides compounds of Formula I and the pharmaceutically acceptable salts thereof, which are inhibitors of the ROMK (Kir1.1) channel. The compounds may be used as diuretic and/or natriuretic agents and for the therapy and prophylaxis of medical conditions including cardiovascular diseases such as hypertension, heart failure and chronic kidney disease and conditions associated with excessive salt and water retention.

20 Claims, No Drawings

(56) References Cited

OTHER PUBLICATIONS

Lewis, L. M., High-throughput screening reveals a small-molecule inhibitor of the Renal Outer Medullary Potassium Channel and Kir7.1, Mol. Pharncol., 2009, 1094-1103, 76.

Lifton, R. P. et al., Molecular Mechanisms of Human Hypertension, Cell, 2001, p. 545-556, vol. 104.

Lorenz, J. N. et al., Impaired Renal NaCl Absorption inMic Lacking the ROMK Potassium Cannel, a Model for Type II Bartter's Syndrome, The Journal of Biological Chemistry, 2002, p. 37871-37880, vol. 277, No. 40.

Lu, M. et al., Absence of Small Conductance K+ Channel (SK) Activity in Apical Membranes of Thick Ascending Limb and Cortical Collectiong Duct in ROMK (Bartter's) Knockout Mice, The Journal of Biological Chemistry, 2002, p. 37881-37887, vol. 277, No. 40.

Molander, G. A. et al., Stereoselective Suzuki-Miyaura Cross-Coupling Reactions of Potassium Alkenyltrifluoroborates with Alkenyl Bromides, J. Org. Chem, 2005, p. 3950-3956, vol. 70.

Molander, G. A. et al., Suzuki-Miyaura Cross-Coupling Reactions of Potassium Vinyltrifluoroborate with Aryl and Heteroaryl Electrophiles, J. Org. Chem, 2006, p. 9861-9686, vol. 71.

Nomura, Y. et al., Synthesis and Structure-Activity Relationships of 2-(4-Benzhydryl-1-piperazinyl)-1-phenylethanols as New Calcium Blockers, Chem. Phar. Bull, 1995, p. 241-246, vol. 43, No. 2.

Reinalter, S. C. et al., Pharmacotyping of hypokalaemic salt-losing tubular disorders, Acta Physiol Scand, 2004, p. 513-521, vol. 181.

Shuck, M. E. et al., Cloning and Characterization of Multiple Forms of the Human Kidney ROM-K Potassium Channel, The Journal of Biological Chemistry, 1994, p. 24261-24270, Vo. 269, No. 39.

Tobin, M. D. et al., Common Variants in Genes Underlying Monogenic Hypertension and Hypotension and Blood Pressure in the General Population, Hypertension, 2008, p. 1658-1664, vol. 51. No. 6.

Wang, W. et al., Renal potassium channesl: recent developments, Current Opinion in Nephrology and Hypertension, 2004, p. 549-555, vol. 13, No. 5.

INHIBITORS OF THE RENAL OUTER MEDULLARY POTASSIUM CHANNEL

CROSS-REFERENCE TO RELATED APPLICATIONS

This application is a U.S. National Phase application under 35 U.S.C. §371 of PCT Application No. PCT/US2015/057279, filed on Oct. 26, 2015, which claims priority from and the benefit of Chinese PCT Patent Application No. PCT/CN2014/089998, filed Oct. 31, 2014.

FIELD OF THE INVENTION

The present invention relates to novel spirocyclic compounds and salts thereof useful as renal outer medullary potassium channel inhibitors. The present invention further relates to compositions containing such compounds, and methods of use thereof.

BACKGROUND OF THE INVENTION

The Renal Outer Medullary Potassium (ROMK) channel (Kir1.1) (see e.g., Ho, K., et al., *Cloning and expression of an inwardly rectifying ATP-regulated potassium channel*, Nature, 1993, 362(6415): p. 31-8.1, 2; and Shuck, M. E., et al., *Cloning and characterization of multiple forms of the human kidney ROM-K potassium channel*, J Biol Chem, 1994, 269(39): p. 24261-70) is a member of the inward rectifier family of potassium channels expressed in two regions of the kidney: thick ascending loop of Henle (TALH) and cortical collecting duct (CCD) (see Hebert, S. C., et al., *Molecular diversity and regulation of renal potassium channels*, Physiol Rev, 2005, 85(1): p. 319-713). At the TALH, ROMK participates in potassium recycling across the luminal membrane which is critical for the function of the $Na^+/K^+/2Cl^-$ co-transporter, the rate-determining step for salt reuptake in this part of the nephron. At the CCD, ROMK provides a pathway for potassium secretion that is tightly coupled to sodium uptake through the amiloride-sensitive sodium channel (see Reinalter, S. C., et al., *Pharmacotyping of hypokalaemic salt-losing tubular disorders*, Acta Physiol Scand, 2004, 181(4): p. 513-21; and Wang, W., *Renal potassium channels: recent developments*, Curr Opin Nephrol Hypertens, 2004, 13(5): p. 549-55). Selective inhibitors of the ROMK channel (also referred to herein as inhibitors of ROMK or ROMK inhibitors) are expected to represent novel diuretics for the treatment of hypertension and other conditions where treatment with a diuretic would be beneficial with potentially reduced liabilities (i.e., hypo- or hyperkalemia, new onset of diabetes, dyslipidemia) over the currently used clinical agents (see Lifton, R. P., A. G. Gharavi, and D. S. Geller, *Molecular mechanisms of human hypertension*, Cell, 2001, 104(4): p. 545-56). Human genetics (Ji, W., et al., *Rare independent mutations in renal salt handling genes contribute to blood pressure variation*, Nat Genet, 2008, 40(5): p. 592-9; and Tobin, M. D., et al., *Common variants in genes underlying monogenic hypertension and hypotension and blood pressure in the general population*, Hypertension, 2008, 51(6): p. 1658-64) and genetic ablation of ROMK in rodents (see Lorenz, J. N., et al., *Impaired renal NaCl absorption in mice lacking the ROMK potassium channel, a model for type II Bartter's syndrome*, J Biol Chem, 2002, 277(40): p. 37871-80 and Lu, M., et al., *Absence of small conductance K+ channel (SK) activity in apical membranes of thick ascending limb and cortical collecting duct in ROMK (Bartter's) knockout mice*, J Biol Chem, 2002, 277(40): p. 37881-7) support these expectations. To our knowledge, the first publicly disclosed small molecule selective inhibitors of ROMK, including VU590, were reported from work done at Vanderbilt University as described in Lewis, L. M., et al., *High-Throughput Screening Reveals a Small-Molecule Inhibitor of the Renal Outer Medullary Potassium Channel and Kir7.1*, Mol Pharmacol, 2009, 76(5): p. 1094-1103. The compound VU591 was later reported in Bhave, G. et al., *Development of a Selective Small-Molecule Inhibitor of Kir1.1, the Renal Outer Medullary Potassium Channel*, Mol Pharmacol, 2011, 79(1), p. 42-50, the text of which states that "ROMK (Kir1.1), is a putative drug target for a novel class of loop diuretics that would lower blood pressure without causing hypokalemia."

Since then, other ROMK inhibitors have been described.

The continued discovery of selective small molecule inhibitors of ROMK is needed for the development of new treatments for hypertension, heart failure, edematous states and related disorders. The compounds of Formula I and salts thereof of this invention are selective inhibitors of the ROMK channel and could be used for the treatment of hypertension, heart failure and other conditions where treatment with a diuretic or natriuretic would be beneficial.

SUMMARY OF THE INVENTION

The present invention provides compounds of Formula I

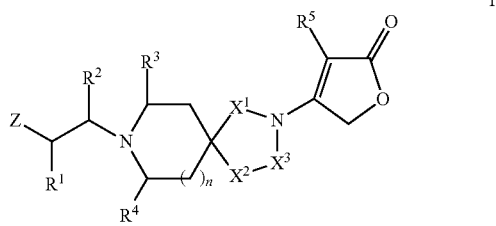

and the pharmaceutically acceptable salts thereof. The compounds of Formula I are inhibitors of the ROMK (Kir1.1) channel. As a result, the compounds of Formula I could be used in methods of treatment, inhibition or amelioration of one or more disease states that could benefit from inhibition of ROMK. The compounds of this invention could be used in methods of treatment which comprise administering a therapeutically or prophylactically effective amount of a compound of Formula I to a patient in need of a diuretic and/or natriuretic agent. Therefore, the compounds of Formula I could be valuable pharmaceutically active compounds for the therapy, prophylaxis or both of medical conditions, including, but not limited to, cardiovascular diseases such as hypertension and heart failure as well as chronic kidney disease, and conditions associated with excessive salt and water retention. The compounds of this invention could further be used in combination with other therapeutically effective agents, including but not limited to, other drugs which are useful for the treatment of hypertension, heart failure and conditions associated with excessive salt and water retention. The invention furthermore relates to processes for preparing compounds of Formula I, and pharmaceutical compositions which comprise compounds of Formula I. These and other aspects of the invention will be evident from the description contained herein.

DETAILED DESCRIPTION OF THE INVENTION

The present invention addresses the following compounds, compounds of (1)-(46):

(1) A compound of Formula I:

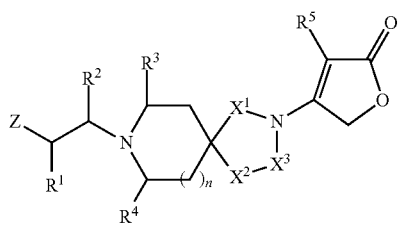

or a pharmaceutically acceptable salt thereof wherein:
$R^1$ is —H, —F, —OH, —$C_{1-3}$alkyl or —$OC_{1-3}$alkyl;
$R^2$ is —H, or $C_{1-4}$alkyl;
$R^3$ is —H, or —$C_{1-3}$alkyl optionally substituted with —OH, —$OCH_3$ or 1 to 3 of —F;
$R^4$ is —H, or —$C_{1-3}$alkyl optionally substituted with —OH, —$OCH_3$ or 1 to 3 of —F;
or $R^3$ and $R^4$ are joined together to form —$CH_2$—$CH_2$—;
n is 1 or 2;
$R^5$ is —H, halo, —$C_{3-6}$cycloalkyl or —$C_{1-3}$alkyl;
$X^1$ is —C(O)—, —$CH_2$—, —$CR^6R^7C(O)$—, —$CH_2CR^6R^7$—, or —$CR^6R^7CH_2$—;
$X^2$ is —O—, —$OCH_2$— or —N($R^8$);
$X^3$ is —C(O)—, —$CH_2$—, —$CR^6R^7C(O)$—, —$CH_2CR^6R^7$—, or —$CR^6R^7CH_2$—;
wherein the ring bearing X1, X2 and X3 is a 5-7 membered ring which results in a (i) 11-13-membered spirocyclic core where n is 1, or a (ii) 12-14-membered spirocyclic core where n is 2; each $R^6$ and $R^7$ is independently —H, halo, —OH, —$OC_{1-3}$alkyl, or —$C_{1-3}$alkyl optionally substituted with —OH, —$OCH_3$ or 1 to 3 of —F;
$R^8$ is —H or —$C_{1-3}$alkyl;
Z is

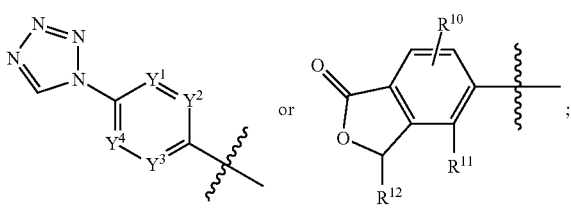

$Y^1$, $Y^2$, $Y^3$ and $Y^4$ are each independently selected from $C(R^9)$ or N;
provided that at most two of $Y^1$, $Y^2$, $Y^3$ and $Y^4$ are N;
each $R^9$ is independently —H, halo, $C_{1-4}$alkyl optionally substituted with 1-3 of —F, or $OC_{1-4}$alkyl;
$R^{10}$ is —H, halo, or $C_{1-4}$alkyl optionally substituted with 1-3 of —F;
$R^{11}$ is —H, $C_{1-4}$alkyl optionally substituted with 1-3 of —F, or halo; and
$R^{12}$ is —H or $C_{1-4}$alkyl.

(2) The compound of (1) having structural Formula Ia or a pharmaceutically acceptable salt thereof:

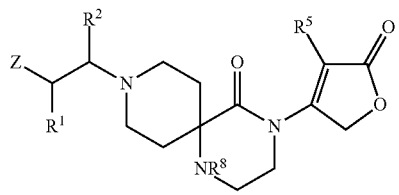

wherein each of the variables Z, $R^1$, $R^2$, $R^5$ and $R^8$, and all other variables therein are as defined above in (1).

(3) The compound of (1) having structural Formula Ib or a pharmaceutically acceptable salt thereof:

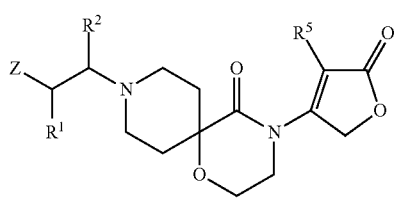

wherein each of the variables Z, $R^1$, $R^2$ and $R^5$, and all other variables therein are as defined above in (1).

(4) The compound of (1) having structural Formula Ic or a pharmaceutically acceptable salt thereof:

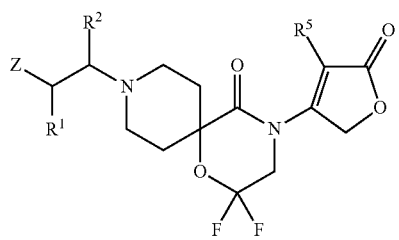

wherein each of the variables Z, $R^1$, $R^2$ and $R^5$, and all other variables therein are as defined above in (1).

(5) The compound of (1) having structural Formula Id or a pharmaceutically acceptable salt thereof:

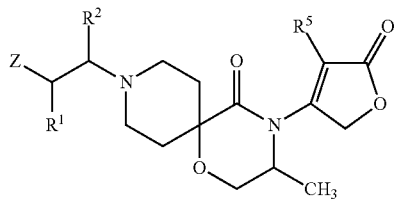

wherein each of the variables Z, $R^1$, $R^2$ and $R^5$, and all other variables therein are as defined above in (1).

(6) The compound of (1) having structural Formula Ie or a pharmaceutically acceptable salt thereof:

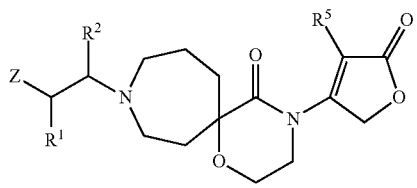

wherein each of the variables Z, $R^1$, $R^2$ and $R^5$, and all other variables therein are as defined above in (1).

(7) The compound of (1) having structural Formula If or a pharmaceutically acceptable salt thereof:

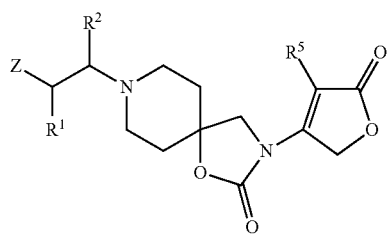

wherein each of the variables Z, $R^1$, $R^2$ and $R^5$, and all other variables therein are as defined above in (1).

(8) The compound of (1) having structural Formula Ig or a pharmaceutically acceptable salt thereof:

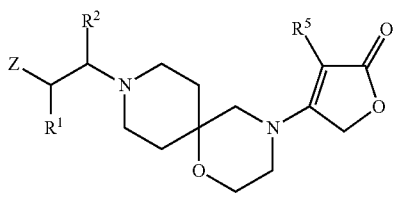

wherein each of the variables Z, $R^1$, $R^2$ and $R^5$, and all other variables therein are as defined above in (1).

(9) The compound of (1) having structural Formula Ih or a pharmaceutically acceptable salt thereof:

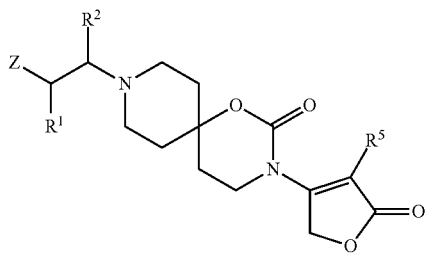

wherein each of the variables Z, $R^1$, $R^2$ and $R^5$, and all other variables therein are as defined above in (1).

(10) The compound of (1) having structural Formula Ii or a pharmaceutically acceptable salt thereof:

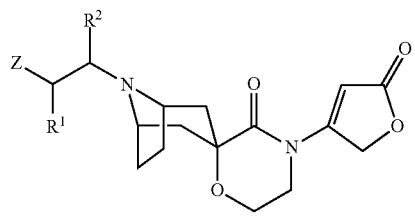

wherein each of the variables Z, $R^1$, $R^2$ and $R^5$, and all other variables therein are as defined above in (1).

(11) The compound of (1) having structural Formula Ij or a pharmaceutically acceptable salt thereof:

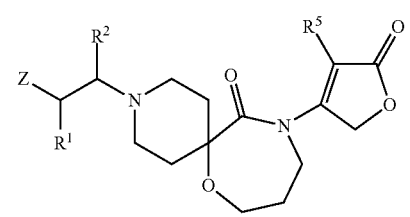

wherein each of the variables Z, $R^1$, $R^2$ and $R^5$, and all other variables therein are as defined above in (1).

(12) The compound of (1) having structural Formula Ik or a pharmaceutically acceptable salt thereof:

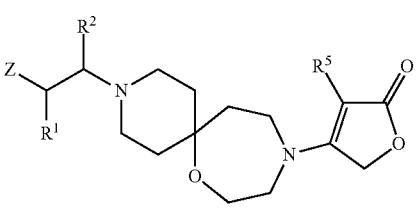

wherein each of the variables Z, $R^1$, $R^2$ and $R^5$, and all other variables therein are as defined above in (1).

(13) The compound of (1) having structural Formula Il or a pharmaceutically acceptable salt thereof:

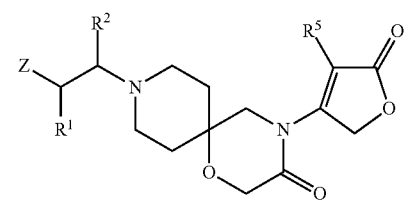

wherein each of the variables Z, $R^1$, $R^2$ and $R^5$, and all other variables therein are as defined above in (1).

(14) The compound of any of (1)-(13), or a pharmaceutically acceptable salt thereof, wherein $R^1$ is —H, —F or —OH.

(15) The compound of any of (1)-(14), or a pharmaceutically acceptable salt thereof, wherein $R^1$ is —OH.

(16) The compound of any of (1)-(15), or a pharmaceutically acceptable salt thereof, wherein $R^2$ is —H.

(17) The compound of any of (1)-(16), or a pharmaceutically acceptable salt thereof, wherein each of $R^3$ and $R^4$ are —H.

(18) The compound of any of (1)-(16), or a pharmaceutically acceptable salt thereof, wherein $R^3$ and $R^4$ are joined together to form —$CH_2CH_2$—.

(19) The compound of any of (1)-(17), or a pharmaceutically acceptable salt thereof, wherein n is 1.

(20) The compound of any of (1)-(19), or a pharmaceutically acceptable salt thereof, wherein $R^5$ is —H, —Cl, —$CH_3$ or cyclopropyl.

(21) The compound of any of (1)-(20), or a pharmaceutically acceptable salt thereof, wherein $R^5$ is —H.

(22) The compound of any of (1)-(20), or a pharmaceutically acceptable salt thereof, wherein $R^5$ is —$CH_3$.

(23) The compound of (1), or a pharmaceutically acceptable salt thereof, wherein $X^1$ is —C(O)—, $X^2$ is —N($R^8$)— and $X^3$ is —$CH_2CH_2$—, wherein $R^8$ is —H or —$CH_3$.

(24) The compound of (1), or a pharmaceutically acceptable salt thereof, wherein $X^1$ is —C(O)—, $X^2$ is —O— and $X^3$ is —$CH_2CH_2$—.

(25) The compound of (1), or a pharmaceutically acceptable salt thereof, wherein $X^1$ is —C(O)—, $X^2$ is —O— and $X^3$ is —$CF_2CH_2$—.

(26) The compound of (1), or a pharmaceutically acceptable salt thereof, wherein $X^1$ is —C(O)—, $X^2$ is —O— and $X^3$ is —$CH_2C(H)(CH_3)$—.

(27) The compound of (1), or a pharmaceutically acceptable salt thereof, wherein $X^1$ is —$CH_2$—, $X^2$ is —O— and $X^3$ is —C(O)—.

(28) The compound of (1), or a pharmaceutically acceptable salt thereof, wherein $X^1$ is —$CH_2$—, $X^2$ is —O— and $X^3$ is —$CH_2CH_2$—.

(29) The compound of (1), or a pharmaceutically acceptable salt thereof, wherein $X^1$ is —$CH_2CH_2$—, $X^2$ is —O— and $X^3$ is —C(O)—.

(30) The compound of (1), or a pharmaceutically acceptable salt thereof, wherein $X^1$ is —C(O)—, $X^2$ is —$OCH_2$— and $X^3$ is —$CH_2CH_2$—.

(31) The compound of (1), or a pharmaceutically acceptable salt thereof, wherein $X^1$ is —$CH_2CH_2$—, $X^2$ is —O— and $X^3$ is —$CH_2CH_2$—.

(32) The compound of (1), or a pharmaceutically acceptable salt thereof, wherein $X^1$ is —$CH_2$—, $X^2$ is —O— and $X^3$ is —$CH_2C(O)$—.

(33) The compound of any of (1)-(32), or a pharmaceutically acceptable salt thereof, wherein Z is

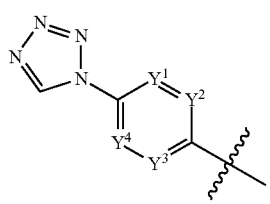

wherein each of the variables $Y^1$, $Y^2$, $Y^3$ and $Y^4$, and all other variables therein are as defined above in (1).

(34) The compound of any of (1)-(33), or a pharmaceutically acceptable salt thereof, wherein Z is

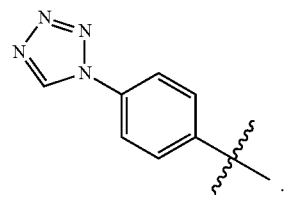 [SMILES: *c1ccc(-n2cnnn2)cc1]

(35) The compound of any of (1)-(33), or a pharmaceutically acceptable salt thereof, wherein Z is

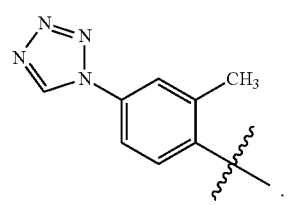 [SMILES: *c1ccc(-n2cnnn2)cc1C]

(36) The compound of any of (1)-(33), or a pharmaceutically acceptable salt thereof, wherein Z is

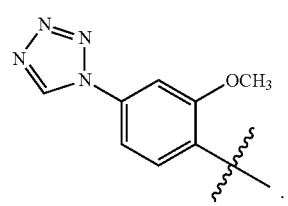 [SMILES: *c1ccc(-n2cnnn2)cc1OC]

(37) The compound of any of (1)-(33), or a pharmaceutically acceptable salt thereof, wherein Z is

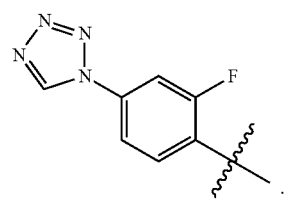 [SMILES: *c1ccc(-n2cnnn2)cc1F]

(38) The compound of any of (1)-(33), or a pharmaceutically acceptable salt thereof, wherein Z is

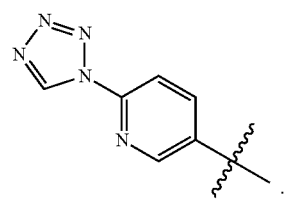 [SMILES: *c1ccc(-n2cnnn2)nc1]

(39) The compound of any of (1)-(33), or a pharmaceutically acceptable salt thereof, wherein Z is

(40) The compound of any of (1)-(33), or a pharmaceutically acceptable salt thereof, wherein Z is

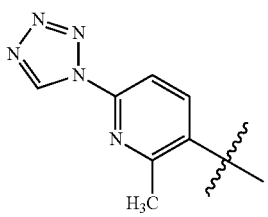

(41) The compound of any of (1)-(33), or a pharmaceutically acceptable salt thereof, wherein Z is

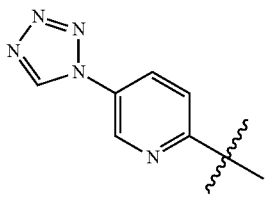

(42) The compound of any of (1)-(33), or a pharmaceutically acceptable salt thereof, wherein Z is

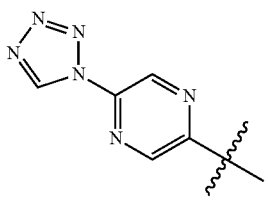

(43) The compound of any of (1)-(33), or a pharmaceutically acceptable salt thereof, wherein Z is

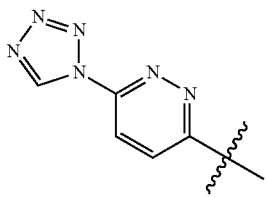

(44) The compound of any of (1)-(32), or a pharmaceutically acceptable salt thereof, wherein Z is

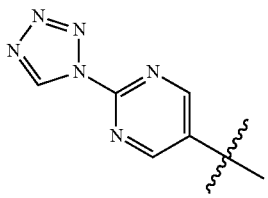

wherein each of the variables $R^{10}$, $R^{11}$ and $R^{12}$ are as defined above in (1).

(45) The compound of any of (1)-(32), or a pharmaceutically acceptable salt thereof, wherein Z is

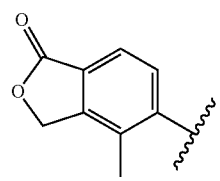

(46) A compound of (1) which is:
9-[(2R)-2-hydroxy-2-(4-methyl-1-oxo-1,3-dihydro-2-benzofuran-5-yl)ethyl]-4-(4-methyl-5-oxo-2,5-dihydrofuran-3-yl)-1,4,9-triazaspiro[5.5]undecan-5-one dihydrochloride [see Example 1];
9-(2-hydroxy-2-(2-methyl-6-(1H-tetrazol-1-yl)pyridin-3-yl)ethyl)-4-(4-methyl-5-oxo-2,5-dihydrofuran-3-yl)-1,4,9-triazaspiro[5.5]undecan-5-one [see Examples 2A-B];
9-(2-(5-(1H-tetrazol-1-yl)pyrazin-2-yl)-2-hydroxyethyl)-4-(4-methyl-5-oxo-2,5-dihydrofuran-3-yl)-1,4,9-triazaspiro[5.5]undecan-5-one [see Examples 3A-B];
(R)-9-(2-(6-(1H-tetrazol-1-yl)pyridin-3-yl)-2-hydroxyethyl)-4-(4-methyl-5-oxo-2,5-dihydrofuran-3-yl)-1,4,9-triazaspiro[5.5]undecan-5-one [see Example 4A];
(S)-9-(2-(6-(1H-tetrazol-1-yl)pyridin-3-yl)-2-hydroxyethyl)-4-(4-methyl-5-oxo-2,5-dihydrofuran-3-yl)-1,4,9-triazaspiro[5.5]undecan-5-one [see Example 4B];
9-(2-(4-(1H-tetrazol-1-yl)phenyl)-2-hydroxyethyl)-4-(4-methyl-5-oxo-2,5-dihydrofuran-3-yl)-1,4,9-triazaspiro[5.5]undecan-5-one [see Examples 5A-B];
(R)-9-(2-(6-(1H-tetrazol-1-yl)pyridin-3-yl)-2-hydroxyethyl)-4-(4-methyl-5-oxo-2,5-dihydrofuran-3-yl)-1-oxa-4,9-diazaspiro[5.5]undecan-5-one [see Example 6A];
(S)-9-(2-(6-(1H-tetrazol-1-yl)pyridin-3-yl)-2-hydroxyethyl)-4-(4-methyl-5-oxo-2,5-dihydrofuran-3-yl)-1-oxa-4,9-diazaspiro[5.5]undecan-5-one [see Example 6B];
(R)-4-(9-(2-(6-(1H-tetrazol-1-yl)pyridin-3-yl)-2-hydroxyethyl)-2,2-difluoro-1-oxa-4,9-diazaspiro[5.5]undecan-4-yl)-3-methylfuran-2(5H)-one [see Example 7A];
(S)-4-(9-(2-(6-(1H-tetrazol-1-yl)pyridin-3-yl)-2-hydroxyethyl)-2,2-difluoro-1-oxa-4,9-diazaspiro[5.5]undecan-4-yl)-3-methylfuran-2(5H)-one [see Example 7B];
(R)-9-(2-hydroxy-2-(4-methyl-1-oxo-1,3-dihydroisobenzofuran-5-yl)ethyl)-4-(4-methyl-5-oxo-2,5-dihydrofuran-3-yl)-1-oxa-4,9-diazaspiro[5.5]undecan-5-one [see Example 8A];
(S)-9-(2-hydroxy-2-(4-methyl-1-oxo-1,3-dihydroisobenzofuran-5-yl)ethyl)-4-(4-methyl-5-oxo-2,5-dihydrofuran-3-yl)-1-oxa-4,9-diazaspiro[5.5]undecan-5-one [see Example 8B];
9-(2-(4-(1H-tetrazol-1-yl)phenyl)-2-hydroxyethyl)-4-(4-methyl-5-oxo-2,5-dihydrofuran-3-yl)-1-oxa-4,9-diazaspiro[5.5]undecan-5-one [see Examples 9A-B];

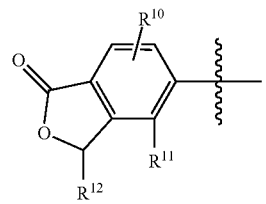

9-((S)-2-(6-(1H-tetrazol-1-yl)pyridin-3-yl)-2-hydroxyethyl)-3-methyl-4-(4-methyl-5-oxo-2,5-dihydrofuran-3-yl)-1-oxa-4,9-diazaspiro[5.5]undecan-5-one [see Examples 10A or 10C];

9-((R)-2-(6-(1H-tetrazol-1-yl)pyridin-3-yl)-2-hydroxyethyl)-3-methyl-4-(4-methyl-5-oxo-2,5-dihydrofuran-3-yl)-1-oxa-4,9-diazaspiro[5.5]undecan-5-one [see Example 10B];

9-((R)-2-hydroxy-2-(4-methyl-1-oxo-1,3-dihydroisobenzofuran-5-yl)ethyl)-3-methyl-4-(4-methyl-5-oxo-2,5-dihydrofuran-3-yl)-1-oxa-4,9-diazaspiro[5.5]undecan-5-one [see Example 11];

(R)-9-(2-(6-(1H-tetrazol-1-yl)pyridin-3-yl)-2-hydroxyethyl)-4-(5-oxo-2,5-dihydrofuran-3-yl)-1-oxa-4,9-diazaspiro[5.5]undecan-5-one [see Example 12];

9-((S)-2-(6-(1H-tetrazol-1-yl)pyridin-3-yl)-2-hydroxyethyl)-3-methyl-4-(5-oxo-2,5-dihydrofuran-3-yl)-1-oxa-4,9-diazaspiro[5.5]undecan-5-one [see Example 13A];

9-((R)-2-(6-(1H-tetrazol-1-yl)pyridin-3-yl)-2-hydroxyethyl)-3-methyl-4-(5-oxo-2,5-dihydrofuran-3-yl)-1-oxa-4,9-diazaspiro[5.5]undecan-5-one [see Example 13B];

9-((R)-2-hydroxy-2-(4-methyl-1-oxo-1,3-dihydroisobenzofuran-5-yl)ethyl)-3-methyl-4-(5-oxo-2,5-dihydrofuran-3-yl)-1-oxa-4,9-diazaspiro[5.5]undecan-5-one [see Example 14];

9-((S)-2-(6-(1H-tetrazol-1-yl)pyridin-3-yl)-2-hydroxyethyl)-4-(4-methyl-5-oxo-2,5-dihydrofuran-3-yl)-1-oxa-4,9-diazaspiro[5.6]dodecan-5-one [see Example 15];

(R)-8-(2-hydroxy-2-(4-methyl-1-oxo-1,3-dihydroisobenzofuran-5-yl)ethyl)-3-(5-oxo-2,5-dihydrofuran-3-yl)-1-oxa-3,8-diazaspiro[4.5]decan-2-one [see Example 16];

8-(2-hydroxy-2-(2-methyl-6-(1H-tetrazol-1-yl)pyridin-3-yl)ethyl)-3-(5-oxo-2,5-dihydrofuran-3-yl)-1-oxa-3,8-diazaspiro[4.5]decan-2-one [see Example 17];

9-(2-(5-(1H-tetrazol-1-yl)pyrazin-2-yl)-2-hydroxyethyl)-4-(4-methyl-5-oxo-2,5-dihydrofuran-3-yl)-1-oxa-4,9-diazaspiro[5.5]undecan-5-one [see Examples 18A-B];

(R)-4-(9-(2-(6-(1H-tetrazol-1-yl)pyridin-3-yl)-2-hydroxyethyl)-1-oxa-4,9-diazaspiro[5.5]undecan-4-yl)furan-2(5H)-one [see Example 19A];

(S)-4-(9-(2-(6-(1H-tetrazol-1-yl)pyridin-3-yl)-2-hydroxyethyl)-1-oxa-4,9-diazaspiro[5.5]undecan-4-yl)furan-2(5H)-one [see Example 19B];

4-(9-(2-(2-methyl-6-(1H-tetrazol-1-yl)pyridin-3-yl)ethyl)-1-oxa-4,9-diazaspiro[5.5]undecan-4-yl)furan-2(5H)-one [see Examples 20A-B];

(R)-5-(1-hydroxy-2-(4-(4-methyl-5-oxo-2,5-dihydrofuran-3-yl)-1-oxa-4,9-diazaspiro[5.5]undecan-9-yl)ethyl)-4-methylisobenzofuran-1(3H)-one [see Example 21];

4-(9-(2-hydroxy-2-(2-methyl-6-(1H-tetrazol-1-yl)pyridin-3-yl)ethyl)-1-oxa-4,9-diazaspiro[5.5]undecan-4-yl)-3-methylfuran-2(5H)-one [see Examples 22A-B];

(R)-5-(2-(4-(4-chloro-5-oxo-2,5-dihydrofuran-3-yl)-1-oxa-4,9-diazaspiro[5.5]undecan-9-yl)-1-hydroxyethyl)-4-methylisobenzofuran-1(3H)-one [see Example 23];

(R)-4-(9-(2-(6-(1H-tetrazol-1-yl)pyridin-3-yl)-2-hydroxyethyl)-1-oxa-4,9-diazaspiro[5.5]undecan-4-yl)furan-2(5H)-one [see Example 24A];

(S)-4-(9-(2-(6-(1H-tetrazol-1-yl)pyridin-3-yl)-2-hydroxyethyl)-1-oxa-4,9-diazaspiro[5.5]undecan-4-yl)-3-chlorofuran-2(5H)-one [see Example 24B];

3-chloro-4-(9-(2-hydroxy-2-(2-methyl-6-(1H-tetrazol-1-yl)pyridin-3-yl)ethyl)-1-oxa-4,9-diazaspiro[5.5]undecan-4-yl)furan-2(5H)-one [see Examples 25A-B];

(R)-9-(2-(6-(1H-tetrazol-1-yl)pyridin-3-yl)-2-hydroxyethyl)-3-(5-oxo-2,5-dihydrofuran-3-yl)-1-oxa-3,9-diazaspiro[5.5]undecan-2-one [see Example 26A];

9-(2-hydroxy-2-(2-methyl-6-(1H-tetrazol-1-yl)pyridin-3-yl)ethyl)-3-(5-oxo-2,5-dihydrofuran-3-yl)-1-oxa-3,9-diazaspiro[5.5]undecan-2-one [see Example 27];

(R)-4-(9-(2-(6-(1H-tetrazol-1-yl)pyridin-3-yl)-2-hydroxyethyl)-1-oxa-4,9-diazaspiro[5.5]undecan-4-yl)-3-cyclopropylfuran-2(5H)-one [see Example 28A];

(S)-4-(9-(2-(6-(1H-tetrazol-1-yl)pyridin-3-yl)-2-hydroxyethyl)-1-oxa-4,9-diazaspiro[5.5]undecan-4-yl)-3-cyclopropylfuran-2(5H)-one [see Example 28B];

3-cyclopropyl-4-(9-(2-hydroxy-2-(2-methyl-6-(1H-tetrazol-1-yl)pyridin-3-yl)ethyl)-1-oxa-4,9-diazaspiro[5.5]undecan-4-yl)furan-2(5H)-one [see Examples 29A-B];

4-(9-(2-hydroxy-2-(2-methyl-4-(1H-tetrazol-1-yl)phenyl)ethyl)-1-oxa-4,9-diazaspiro[5.5]undecan-4-yl)furan-2(5H)-one [see Examples 30A-B];

4-(9-(2-hydroxy-2-(2-methyl-4-(1H-tetrazol-1-yl)phenyl)ethyl)-1-oxa-4,9-diazaspiro[5.5]undecan-4-yl)-3-methylfuran-2(5H)-one [see Examples 31A-B];

4-(9-(2-(2-fluoro-4-(1H-tetrazol-1-yl)phenyl)-2-hydroxyethyl)-1-oxa-4,9-diazaspiro[5.5]undecan-4-yl)-3-methylfuran-2(5H)-one [see Examples 32A-B];

4-(9-(2-hydroxy-2-(2-methoxy-4-(1H-tetrazol-1-yl)phenyl)ethyl)-1-oxa-4,9-diazaspiro[5.5]undecan-4-yl)-3-methylfuran-2(5H)-one [see Examples 33A-B];

(R)-9-(2-hydroxy-2-(4-methyl-1-oxo-1,3-dihydroisobenzofuran-5-yl)ethyl)-1-methyl-4-(4-methyl-5-oxo-2,5-dihydrofuran-3-yl)-1,4,9-triazaspiro[5.5]undecan-5-one [see Example 34];

9-(2-hydroxy-2-(2-methyl-6-(1H-tetrazol-1-yl)pyridin-3-yl)ethyl)-1-methyl-4-(4-methyl-5-oxo-2,5-dihydrofuran-3-yl)-1,4,9-triazaspiro[5.5]undecan-5-one [see Examples 35A-B];

(1R,2'R,5S)-8-((R)-2-hydroxy-2-(4-methyl-1-oxo-1,3-dihydroisobenzofuran-5-yl)ethyl)-4'-(5-oxo-2,5-dihydrofuran-3-yl)-8-azaspiro[bicyclo[3.2.1]octane-3,2'-morpholin]-3'-one [see Example 36];

(R)-3-(2-hydroxy-2-(4-methyl-1-oxo-1,3-dihydroisobenzofuran-5-yl)ethyl)-11-(4-methyl-5-oxo-2,5-dihydrofuran-3-yl)-7-oxa-3,11-diazaspiro[5.6]dodecan-12-one [see Example 37];

3-(2-hydroxy-2-(2-methyl-6-(1H-tetrazol-1-yl)pyridin-3-yl)ethyl)-11-(4-methyl-5-oxo-2,5-dihydrofuran-3-yl)-7-oxa-3,11-diazaspiro[5.6]dodecan-12-one [see Example 38];

9-(2-hydroxy-2-(2-methyl-6-(1H-tetrazol-1-yl)pyridin-3-yl)ethyl)-4-(4-methyl-5-oxo-2,5-dihydrofuran-3-yl)-1-oxa-4,9-diazaspiro[5.5]undecan-5-one [see Example 39];

4-(3-(2-(5-(1H-tetrazol-1-yl)pyrazin-2-yl)-2-hydroxyethyl)-7-oxa-3,10-diazaspiro[5.6]dodecan-10-yl)-3-methylfuran-2(5H)-one [see Example 40];

(R)-5-(1-hydroxy-2-(10-(4-methyl-5-oxo-2,5-dihydrofuran-3-yl)-7-oxa-3,10-diazaspiro[5.6]dodecan-3-yl)ethyl)-4-methylisobenzofuran-1(3H)-one [see Example 41];

(1R,2'R,5S)-8-((R)-2-hydroxy-2-(4-methyl-1-oxo-1,3-dihydroisobenzofuran-5-yl)ethyl)-4'-(4-methyl-5-oxo-2,5-dihydrofuran-3-yl)-8-azaspiro[bicyclo[3.2.1]octane-3,2'-morpholin]-3'-one [see Example 42];

9-(2-(5-(1H-tetrazol-1-yl)pyridin-2-yl)-2-hydroxyethyl)-4-(4-methyl-5-oxo-2,5-dihydrofuran-3-yl)-1-oxa-4,9-diazaspiro[5.5]undecan-5-one [see Example 43];

(1R,2'r,5S)-8-(2-(5-(1H-tetrazol-1-yl)pyrazin-2-yl)-2-hydroxyethyl)-4'-(4-methyl-5-oxo-2,5-dihydrofuran-3-yl)-8-azaspiro[bicyclo[3.2.1]octane-3,2'-morpholin]-3'-one [see Example 44];

9-(2-(6-(1H-tetrazol-1-yl)pyridazin-3-yl)-2-hydroxyethyl)-4-(4-methyl-5-oxo-2,5-dihydrofuran-3-yl)-1-oxa-4,9-diazaspiro[5.5]undecan-5-one [see Examples 45A-B];

9-(2-(2-(1H-tetrazol-1-yl)pyrimidin-5-yl)-2-hydroxyethyl)-4-(4-methyl-5-oxo-2,5-dihydrofuran-3-yl)-1-oxa-4,9-diazaspiro[5.5]undecan-5-one [see Examples 46A-B];

(1R,2'R,5S)-8-((R)-2-(2-(6-(1H-tetrazol-1-yl)pyridin-3-yl)-2-hydroxyethyl)-4'-(4-methyl-5-oxo-2,5-dihydrofuran-3-yl)-8-azaspiro[bicyclo[3.2.1]octane-3,2'-morpholin]-3'-one [see Example 47];

4-(9-(2-(5-(1H-tetrazol-1-yl)pyrazin-2-yl)-2-hydroxyethyl)-1-oxa-4,9-diazaspiro[5.5]undecan-4-yl)-3-methylfuran-2(5H)-one [see Examples 48A-B];

9-(2-(4-methyl-1-oxo-1,3-dihydroisobenzofuran-5-yl)ethyl)-4-(4-methyl-5-oxo-2,5-dihydrofuran-3-yl)-1-oxa-4,9-diazaspiro[5.5]undecan-5-one [see Example 49];

9-(2-(4-methyl-1-oxo-1,3-dihydroisobenzofuran-5-yl)ethyl)-4-(4-methyl-5-oxo-2,5-dihydrofuran-3-yl)-1-oxa-4,9-diazaspiro[5.5]undecan-5-one [see Example 50];

9-(2-(6-(1H-tetrazol-1-yl)pyridazin-3-yl)ethyl)-4-(4-methyl-5-oxo-2,5-dihydrofuran-3-yl)-1-oxa-4,9-diazaspiro[5.5]undecan-5-one [see Example 51];

9-(2-(5-(1H-tetrazol-1-yl)pyrazin-2-yl)ethyl)-4-(4-methyl-5-oxo-2,5-dihydrofuran-3-yl)-1-oxa-4,9-diazaspiro[5.5]undecan-5-one [see Example 52];

9-(2-(6-(1H-tetrazol-1-yl)pyridin-3-yl)ethyl)-4-(4-methyl-5-oxo-2,5-dihydrofuran-3-yl)-1-oxa-4,9-diazaspiro[5.5]undecan-5-one [see Example 53];

(1R,2'r,5S)-8-(2-(6-(1H-tetrazol-1-yl)pyridazin-3-yl)ethyl)-4'-(5-oxo-2,5-dihydrofuran-3-yl)-8-azaspiro[bicyclo[3.2.1]octane-3,2'-morpholin]-3'-one [see Example 54];

(R)-9-(2-(6-(1H-tetrazol-1-yl)pyridin-3-yl)-2-fluoroethyl)-4-(4-methyl-5-oxo-2,5-dihydrofuran-3-yl)-1-oxa-4,9-diazaspiro[5.5]undecan-5-one [see Example 55];

(S)-9-(2-(6-(1H-tetrazol-1-yl)pyridin-3-yl)-2-fluoroethyl)-4-(4-methyl-5-oxo-2,5-dihydrofuran-3-yl)-1-oxa-4,9-diazaspiro[5.5]undecan-5-one [see Example 56];

(R)-9-(2-fluoro-2-(4-methyl-1-oxo-1,3-dihydroisobenzofuran-5-yl)ethyl)-4-(4-methyl-5-oxo-2,5-dihydrofuran-3-yl)-1-oxa-4,9-diazaspiro[5.5]undecan-5-one [see Example 57];

(S)-9-(2-fluoro-2-(4-methyl-1-oxo-1,3-dihydroisobenzofuran-5-yl)ethyl)-4-(4-methyl-5-oxo-2,5-dihydrofuran-3-yl)-1-oxa-4,9-diazaspiro[5.5]undecan-5-one [see Example 58];

(R)-9-(2-hydroxy-2-(4-methyl-1-oxo-1,3-dihydroisobenzofuran-5-yl)ethyl)-4-(4-methyl-5-oxo-2,5-dihydrofuran-3-yl)-1-oxa-4,9-diazaspiro[5.5]undecan-3-one [see Example 59];

9-(2-hydroxy-2-(2-methyl-6-(1H-tetrazol-1-yl)pyridin-3-yl)ethyl)-4-(4-methyl-5-oxo-2,5-dihydrofuran-3-yl)-1-oxa-4,9-diazaspiro[5.5]undecan-3-one [see Example 60]; or a pharmaceutically acceptable salt thereof.

The compounds of the present invention are further described herein using the terms defined below unless otherwise specified.

"Alkyl", as well as other groups having the prefix "alk", such as alkoxy, and the like, means carbon chains which may be linear or branched, or combinations thereof, containing the indicated number of carbon atoms. Examples of alkyl groups include methyl, ethyl, propyl, isopropyl, butyl, sec- and tert-butyl, pentyl, hexyl, heptyl, octyl, nonyl and the like. In specific embodiments, alkyl means a linear or branched $C_{1-6}$ or $C_{1-3}$alkyl.

"Alkoxy" refers to an alkyl group linked to oxygen. In specific embodiments, alkoxy means a linear or branched $C_{1-6}$ or $C_{1-3}$ alkoxy in which the point of attachment is at oxygen.

"Cycloalkyl" means a saturated cyclic hydrocarbon radical having the number of carbon atoms designated. Examples of cycloalkyl include cyclopropyl, cyclobutyl, cyclopentyl and cyclohexyl. In specific embodiments, cycloalkyl means a $C_{3-6}$ or $C_{3-4}$ cycloalkyl. In particular embodiments, cycloalkyl means $C_3$ cycloalkyl (or cyclopropyl).

"Halogen" or "halo" includes fluorine, chlorine, bromine and iodine.

Unless expressly depicted or described otherwise, variables depicted in a structural formula with a "floating" bond, such as substituent $R^{10}$, are permitted on any available carbon atom in the ring to which each is attached.

Substitution, where applicable, may be on any available carbon atom that results in a stable structure.

Also, number ranges where provided (e.g., 1-6) expressly include each and every number in that range as a discrete embodiment. For example, "1-6" includes 1-6, 1-5, 1-4, 1-3, 1-2, 6, 5, 4, 3, 2 and 1 as distinct embodiments.

Atoms of the compounds described herein may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of any of (1)-(46). For example, different isotopic forms of hydrogen (H) include protium (1H) and deuterium (2H). Protium is the predominant hydrogen isotope found in nature. Enriching for deuterium may yield certain therapeutic advantages, such as increasing in vivo half-life or reducing dosage requirements, or may provide a compound useful as a standard for characterization of biological samples. Isotopically-enriched compounds of any of (1)-(46) described herein can be prepared without undue experimentation by conventional techniques well known to those skilled in the art or by processes analogous to those described in the Examples herein using appropriate isotopically-enriched reagents and/or intermediates.

Individual tautomers of the compounds of any of (1)-(46), as well as mixtures thereof, are encompassed herein. Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers.

Compounds described herein may contain an asymmetric center and may thus exist as enantiomers. Where the compounds according to the invention possess two or more asymmetric centers, they may additionally exist as diastereomers. When bonds to the chiral carbon are depicted as straight lines in the formulas of the invention, it is understood that both the (R) and (S) configurations of the chiral carbon, and hence both enantiomers and mixtures thereof, are embraced. The present invention includes all such possible stereoisomers as substantially pure resolved enantiomers, racemic mixtures thereof, as well as mixtures of diastereomers. Except where otherwise specified, the formulae encompassing compounds of the present invention are shown without a definitive stereochemistry at certain positions. The present invention therefore may be understood to include all stereoisomers of compounds of any of (1)-(46) and pharmaceutically acceptable salts thereof.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of any of (1)-(46) may be obtained by stereospecific synthesis using optically pure starting materials or reagents of known configuration.

Furthermore, some of the crystalline forms for compounds of the present invention may exist as polymorphs and as such are intended to be included in the present invention. In addition, some of the compounds of the instant invention may form solvates with water or common organic solvents. Solvates, and in particular, the hydrates of the compounds of any of (1)-(46) are also included in the present invention.

The term "pharmaceutically acceptable salt" refers to a salt prepared from pharmaceutically acceptable non-toxic bases or acids including inorganic bases or acids and organic bases or acids.

Salts of basic compounds encompassed within the term "pharmaceutically acceptable salt" refer to non-toxic salts of the compounds described herein which are generally prepared by reacting the free base with a suitable organic or inorganic acid. Representative salts of basic compounds described herein include, but are not limited to, the following: acetate, benzenesulfonate, benzoate, bicarbonate, bisulfate, bitartrate, borate, bromide, camsylate, carbonate, chloride, clavulanate, citrate, edetate, edisylate, estolate, esylate, formate, fumarate, gluceptate, gluconate, glutamate, hexylresorcinate, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, palmitate, pamoate (embonate), pantothenate, phosphate/diphosphate, polygalacturonate, salicylate, stearate, sulfate, subacetate, succinate, tannate, tartrate, teoclate, tosylate, triethiodide and valerate. Furthermore, where the compounds described herein carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. In particular embodiments, the salt is selected from ammonium, calcium, magnesium, potassium, or sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, isopropylamine, lysine, methylglucamine, morpholine, piperazine, piperidine, polyamine resins, procaine, purines, theobromine, triethylamine, trimethylamine, tripropylamine, tromethamine, and the like.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$alkyl esters and —$C_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

The compounds of Formula I according to the invention are inhibitors of ROMK, and therefore could be used as diuretic and/or natriuretic agents. ROMK inhibitors may be used to help to increase urination and increase urine volume and also to prevent or reduce reabsorption of sodium in the kidneys leading to increased excretion of sodium and water. Therefore, the compounds could be used for treatment or prophylaxis or both of disorders that benefit from increased excretion of water and sodium from the body. Accordingly, the compounds of this invention could be used in a method for inhibiting ROMK comprising administering a compound of Formula I in a ROMK-inhibitory effective amount to a patient in need thereof. This also encompasses the use of the compounds for inhibiting ROMK in a patient comprising administering a compound of Formula I in a therapeutically effective amount to a patient in need of diueresis, natriuresis or both. The inhibition of ROMK by the compounds of Formula I can be examined, for example, in the Thallium Flux Assay described below. Moreover, this invention also relates to the use of the compounds of Formula I or salts thereof to validate in vitro assays, for example but not limited to the Thallium Flux Assay described herein.

The compounds of this invention could be used in a method for causing diuresis, natriuresis or both, comprising administering a compound of Formula I in a therapeutically effective amount to a patient in need thereof. Therefore, the compounds of Formula I of this invention could be used in methods for treatment of, prevention of or reduction of risk for developing medical conditions that benefit from increased excretion of water and sodium, such as but not limited to one or more of hypertension, such as essential hypertension (also known as primary or idiopathic hypertension) which is a form of hypertension for which no cause can be found, heart failure (which includes both acute heart failure and chronic heart failure, the latter also known as congestive heart failure) and/or other conditions associated with excessive salt and water retention. The compounds could also be used to treat hypertension which is associated with any of several primary diseases, such as renal, pulmonary, endocrine, and vascular diseases, including treatment of patients with medical conditions such as heart failure and/or chronic kidney disease. Furthermore, the compounds of Formula I could be used in methods for treatment of, prevention of or reduction of risk for developing one or more disorders such as pulmonary hypertension, particularly pulmonary arterial hypertension (PAH), cardiovascular disease, edematous states, diabetes mellitus, diabetes insipidus, postoperative volume overload, endothelial dysfunction, diastolic dysfunction, systolic dysfunction, stable and unstable angina pectoris, thromboses, restenosis, myocardial infarction, stroke, cardiac insufficiency, pulmonary hypertonia, atherosclerosis, hepatic cirrhosis, ascites, pre-eclampsia, cerebral edema, nephropathy, glomerulonephritis, nephrotic syndrome, acute kidney insufficiency, chronic kidney insufficiency (also referred to as chronic kidney disease, or more generally as renal impairment), acute tubular necrosis, hypercalcemia, idiopathic edema, Dent's disease, Meniere's disease, glaucoma, benign intracranial hypertension, and other conditions for which a diuretic or natriuretic or both would have therapeutic or prophylactic benefit. The compounds of the invention may be administered to a patient having, or at risk of having, one or more conditions for which a diuretic or natriuretic or both would have therapeutic or prophylactic benefit such as those described herein.

The compounds of Formula I may potentially have reduced unintended effects (for example, hypo- or hyperkalemia, new onset of diabetes, dyslipidemia, etc.) over currently used clinical agents. Also the compounds may have reduced risk for diuretic tolerance, which can be a problem with long-term use of loop diuretics.

In general, compounds that are ROMK inhibitors can be identified as those compounds which, when tested, have an IC50 of 5 µM or less, preferably 1 µM or less, and more particularly 0.25 µM or less, in the Thallium Flux Assay, described in more detail further below.

The dosage amount of the compound to be administered depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of Formula I. A consideration of these factors is well within the purview of the ordinarily skilled clinician for the purpose of determining the therapeutically effective or prophylactically effective dosage amount needed to prevent, counter, or arrest the progress of the condition. It is expected that the compound will be administered chronically on a daily basis for a length of time appropriate to treat or prevent the medical condition relevant to the patient, including a course of therapy lasting days, months, years or the life of the patient.

In general, a daily dose of approximately 0.001 to 100 mg/kg, particularly 0.001 to 30 mg/kg, in particular 0.001 to 10 mg/kg (in each case mg per kg of bodyweight) is appropriate for administration to an adult weighing approximately 75 kg in order to obtain the desired results. The daily dose is particularly administered in a single dose or can be divided into several, for example two, three or four individual doses, and may be, for example but not limited to, 0.1 mg, 0.25 mg, 0.5 mg, 0.75 mg, 1 mg, 1.25 mg, 2 mg, 2.5 mg, 5 mg, 10 mg, 20 mg, 40 mg, 50 mg, 75 mg, 100 mg, 125 mg, 150 mg, 175 mg, 200 mg, etc., on a daily basis. In some cases, depending on the potency of the compound or the individual response, it may be necessary to deviate upwards or downwards from the given daily dose. Furthermore, the compound may be formulated for immediate or modified release such as extended or controlled release.

The term "patient" includes animals, particularly mammals and especially humans, who use the instant active agents for the prophylaxis or treatment of a medical condition. Administering of the drug to the patient includes both self-administration and administration to the patient by another person. The patient may be in need of treatment for an existing disease or medical condition, or may desire prophylactic treatment to prevent or reduce the risk for developing said disease or medical condition or developing long-term complications from a disease or medical condition.

The term "therapeutically effective amount" is intended to mean that amount of a drug or pharmaceutical agent that will elicit the biological or medical response of a tissue, a system, animal or human that is being sought by a researcher, veterinarian, medical doctor or other clinician. A "prophylactically effective amount" is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. The terms "preventing," "prevention," "prophylactic" and derivatives of these terms as used herein refer to administering a compound to a patient before the onset of clinical symptoms of a condition not yet present in the patient. It is understood that a specific daily dosage amount can simultaneously be both a therapeutically effective amount, e.g., for treatment of hypertension, and a prophylactically effective amount, e.g., for prevention or reduction of risk of myocardial infarction or prevention or reduction of risk for complications related to hypertension.

In the methods of treatment of this invention, the ROMK inhibitors may be administered via any suitable route of administration such as, for example, orally, parenterally, or rectally in dosage unit formulations containing conventional non-toxic pharmaceutically acceptable carriers, adjuvants and vehicles. The term parenteral as used herein includes subcutaneous injections, intravenous (IV), intramuscular, intrasternal injection or infusion techniques. Oral formulations are preferred for treatment of chronic indications such as hypertension or chronic heart failure, particularly solid oral dosage units such as pills, tablets or capsules, and more particularly tablets. IV dosing is preferred for acute treatment, for example for the treatment of acute heart failure.

This invention also provides pharmaceutical compositions comprised of a compound of Formula I and a pharmaceutically acceptable carrier which is comprised of one or more excipients or additives. An excipient or additive is an inert substance used to formulate the active drug ingredient. For oral use, the pharmaceutical compositions of this invention containing the active ingredient may be in forms such as pills, tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Tablets contain the active ingredient in admixture with non-toxic pharmaceutically acceptable excipients which are suitable for the manufacture of tablets. The excipients may be for example, inert diluents, such as calcium carbonate, sodium carbonate, lactose, mannitol, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc.

Pharmaceutical compositions may also contain other customary additives, for example but not limited to, wetting agents, stabilizers, emulsifiers, dispersants, preservatives, sweeteners, colorants, flavorings, aromatizers, thickeners, buffer substances, solvents, solubilizers, agents for achieving a depot effect, salts for altering the osmotic pressure, coating agents or antioxidants. Oral immediate-release and time-controlled release dosage forms may be employed, as well as enterically coated oral dosage forms. Tablets may be uncoated or they may be coated by known techniques for aesthetic purposes, to mask taste or for other reasons. Coatings can also be used to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an anti-oxidant such as ascorbic acid. Syrups and elixirs may be formulated with sweetening agents, for example glycerol, propylene glycol, sorbitol or sucrose.

The instant invention also encompasses a process for preparing a pharmaceutical composition comprising combining a compound of Formula I with a pharmaceutically acceptable carrier. Also encompassed is the pharmaceutical composition which is made by combining a compound of Formula I with a pharmaceutically acceptable carrier. Furthermore, a therapeutically effective amount of a compound of this invention can be used for the preparation of a medicament useful for inhibiting ROMK, for causing diuresis and/or natriuresis, and/or for treating, preventing or reducing the risk for any of the medical conditions described herein, in dosage amounts described herein.

The amount of active compound of Formula I and/or its pharmaceutically acceptable salts in the pharmaceutical composition may be, for example but not limited to, from about 0.1 mg to 1 g, particularly 0.1 mg to about 200 mg, more particularly from about 0.1 mg to about 100 mg, and even more particularly from about 0.1 to about 50 mg, per dose on a free acid/free base weight basis, but depending on the type of the pharmaceutical composition, potency of the active ingredient and/or the medical condition being treated, it could also be lower or higher. Pharmaceutical compositions usually comprise about 0.5 to about 90 percent by weight of the active compound on a free acid/free base weight basis.

The compounds of Formula I inhibit ROMK. Due to this property, apart from use as pharmaceutically active compounds in human medicine and veterinary medicine, they can also be employed as a scientific tool or as aid for biochemical investigations in which such an effect on ROMK is intended, and also for diagnostic purposes, for example in the in vitro diagnosis of cell samples or tissue samples. The compounds of Formula I can also be employed as intermediates for the preparation of other pharmaceutically active compounds.

One or more additional pharmacologically active agents may be administered in combination with a compound of Formula I. The additional active agent (or agents) is intended to mean a medicinal compound that is different from the compound of Formula I, and which is a pharmaceutically active agent (or agents) that is active in the body, including pro-drugs, for example esterified forms, that convert to pharmaceutically active form after administration, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of Formula I in a single dosage formulation (a fixed dose drug combination), or may be administered to the patient in one or more separate dosage formulations which allows for concurrent or sequential administration of the active agents (co-administration of the separate active agents). Examples of the one or more additional active agents which may be employed include but are not limited to thiazide-like diuretics, e.g., hydrochlorothiazide (HCTZ or HCT); angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); dual inhibitors of angiotensin converting enzyme (ACE) and neutral endopeptidase (NEP) such as omapatrilat, sampatrilat and fasidotril; angiotensin II receptor antagonists, also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO®), losartan, e.g., losartan potassium (COZAAR®), olmesartan, e.g, olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®), etc.); potassium sparing diuretics such as amiloride HCl, spironolactone, epleranone, triamterene, each with or without HCTZ; carbonic anhydrase inhibitors, such as acetazolamide; neutral endopeptidase inhibitors (e.g., thiorphan and phosphoramidon); angiotensin receptor neprilysin inhibitors (e.g., LCZ696); aldosterone antagonists; aldosterone synthase inhibitors; renin inhibitors (e.g., enalkrein; RO 42-5892; A 65317; CP 80794; ES 1005; ES 8891; SQ 34017; aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate), SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine, bepridil, nisoldipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists; peripheral vasodilators (e.g. hydralazine); nitrates or nitric oxide donating compounds, e.g. isosorbide mononitrate; lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), SGLT2 inhibitors (e.g., canagliflozin, dapagliflozin, ipragliflozin, empagliflozin, tofogliflozin, luseogliflozin/TS-071, ertugliflozin, and remogliflozin), dipeptidyl peptidase inhibitors, (e.g., sitagliptin (JANUVIA®), omarigliptin, alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; phosphodiesterase-5 (PDE5) inhibitors such as sildenafil (Revatio, Viagra), tadalafil (Cialis, Adcirca) vardenafil HCl (Levitra); or with other drugs beneficial for the prevention or the treatment of the above-mentioned diseases including but not limited to diazoxide; and including the free-acid, free-base, and pharmaceutically acceptable salt forms, pro-drug forms (including but not limited to esters), and salts of pro-drugs of the above medicinal agents where chemically possible. Trademark names of pharmaceutical drugs noted above are provided for exemplification of the marketed form of the active agent(s); such pharmaceutical drugs could be used in a separate dosage form for concurrent or sequential administration with a compound of Formula I, or the active agent(s) therein could be used in a fixed dose drug combination including a compound of Formula I.

EXAMPLES

Several methods for preparing the compounds of this invention are described in the following Schemes and Examples. Starting materials and intermediates are purchased, made from known procedures, or as otherwise illustrated. Some frequently applied routes to the compounds of Formula I are also described by the Schemes as follows. In some cases the order of carrying out the steps of reaction schemes may be varied to facilitate the reaction or to avoid unwanted reaction products. Unless specified otherwise, the "R", "Z", "X", "Y" and "n" substituents in the Schemes correspond to the substituents defined in Formula I at the same positions on the structures.

Compound 1.3, which is substituted at the benzylic position with an OH group, can be prepared following the sequence detailed in Scheme 1. Coupling of epoxide 1.1 to spirocyclic amines 1.2 at elevated temperatures leads to the formation of alcohols 1.3 (Nomura, Y. et al. Chemical & Pharmaceutical Bulletin, 1995, 43(2), 241-6). The reaction can be carried out with conventional heating, or by heating using a microwave apparatus. A number of solvents can be used in this reaction, for example, ethanol and 2-propanol. Spirocyclic amines may be free bases, or they may be salts, in which case a base such as triethylamine or N,N-diisopropylethylamine may be added. Note that when enantiopure chiral epoxides are employed (such as (R)-1.1 in Scheme 1) epoxide opening occurs with retention of stereochemistry in the benzylic position and individual isomer (R)-1.3 may be obtained (and if the (S)-epoxide is employed the alcohol produced will have the opposite stereochemistry to that shown). Alternatively, chiral HPLC separation of enantiomers or diastereomers of 1.3 may be performed to provide single enantiomers or diastereomers.

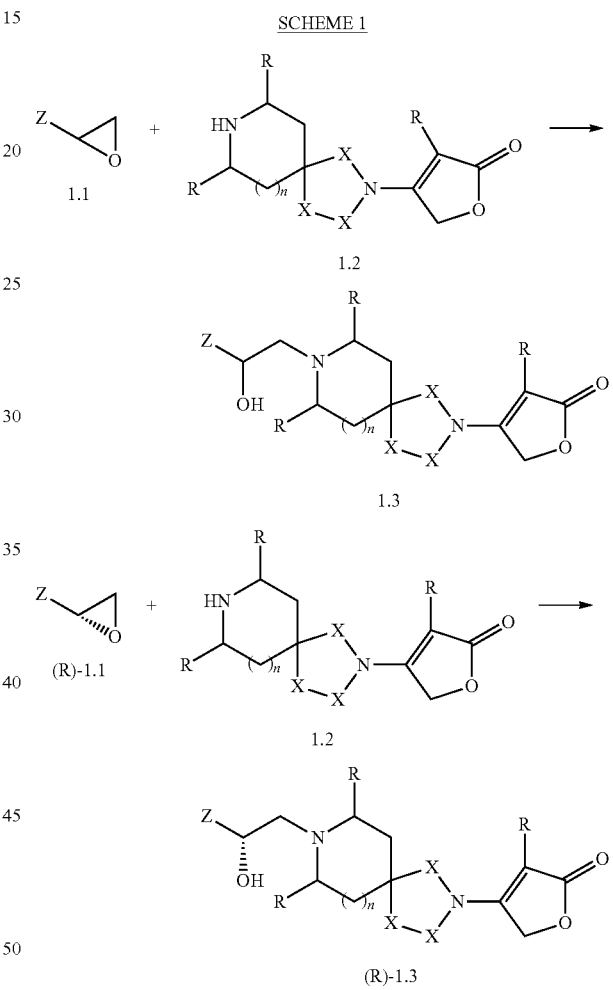

Compounds of formula 2.3 can be prepared by the sequence detailed in Scheme 2. Alhehydes or ketones 2.1 may be used in reductive alkylation reactions of spirocyclic amines 1.2 to afford ROMK inhibitors of the formula 2.3 by using various reductive amination conditions (for example using sodium cyanoborohydride, sodium triacetoxy borohydride, or titanium tetra-isopropoxide, followed by sodium borohydride or sodium cyanoborohydride). Alternatively, compounds of formula 2.3 can also be prepared by addition of amine 1.2 to an olefin of type 2.2 in the presence of a catalyst, e.g., Rh(COD)$_2$BF$_4$/DPEPhos. Under this condition, the olefins of type 2.2 may be required to be activated by a nitrogen atom or other electron-withdrawing group at the position ortho to the double bond on the aromatic ring.

SCHEME 2

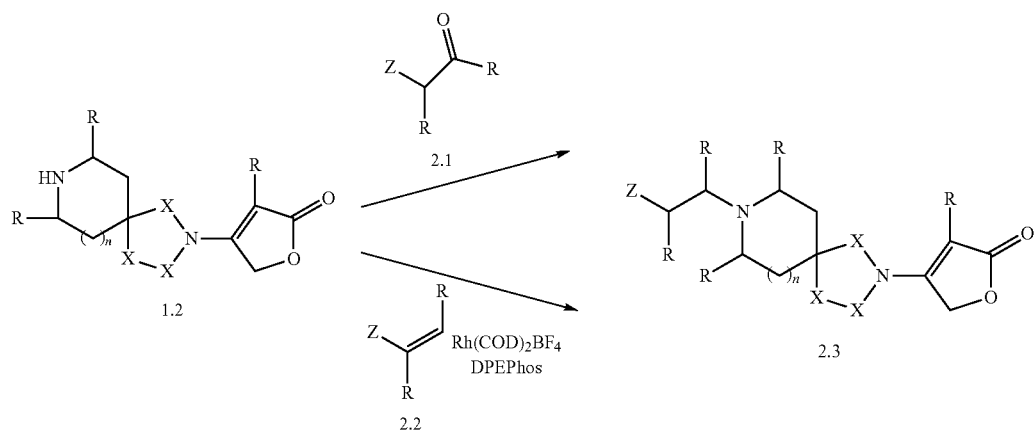

Preparation of tetrazole styrene and tetrazole-epoxide intermediates of types 3.4 and 3.5 may start from halo-substituted aniline 3.1 (Scheme 3, X=halo). Thus, formation of the tetrazole ring can be accomplished by stirring $CF_3CO_2TMS$, $N_3TMS$ and $CH(OEt)_3$ in ethyl acetate or $NaN_3$ and $CH(OEt)_3$ in acetic acid at room temperature. The epoxide ring in intermediate 3.5 can be built by treatment of 3.2 (where X is chloride, bromide, iodide, or trifluoromethane sulfonate) with potassium vinyl trifluoroborate (Molander, G.; Luciana, A. Journal of Organic Chemistry, 2005, 70(10), 3950-3956) under palladium catalyzed coupling conditions followed by epoxidation of the formed styrene with NBS/NaOH. The intermediate styrene 3.4 can be used to prepare ROMK inhibitors in place of 2.2 according to Scheme 2. Other methods for formation of styrene may be employed, for example, using vinylstannane reagents and palladium catalysis, and other methods for epoxidation of the styrene may be used, for rexample, mCPBA. The racemic epoxides of formula 3.5 can be resolved under chiral HPLC chromatography conditions to afford its enantiomers (R)-3.5 and (S)-3.5, which can be used in place of 1.1 according to Scheme 1.

SCHEME 3

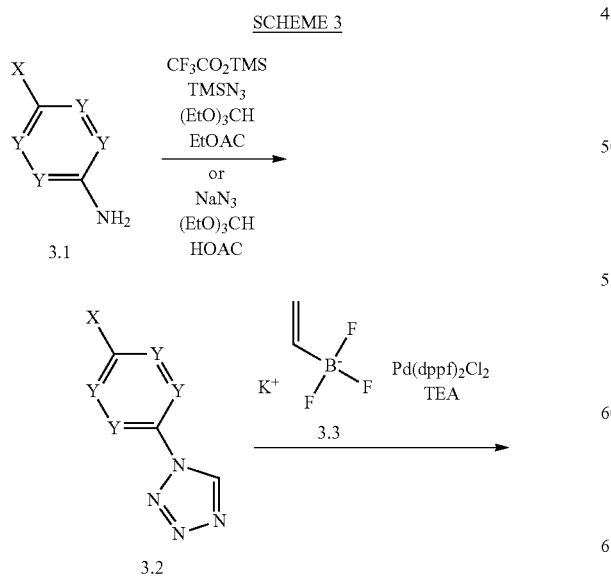

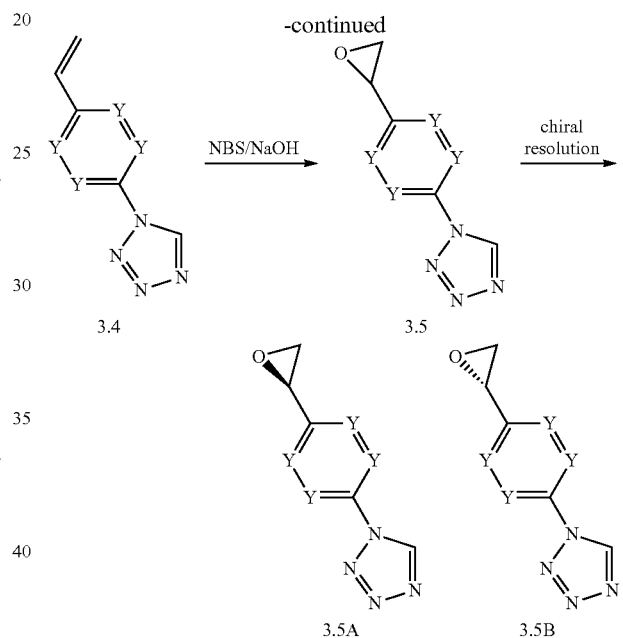

Aldehydes 4.3 can be prepared in numerous ways, including that described in Scheme 4. Aldehyde 4.3 can be prepared by hydrogenation of intermediate epoxides 3.5 followed by oxidation with Dess-Martin periodinane. Aldehydes 4.3 can be used in place of intermediates 2.1 in Scheme 2 to prepare ROMK inhibitors.

SCHEME 4

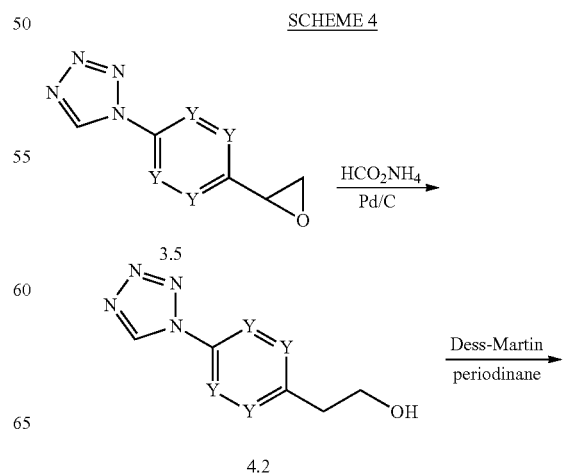

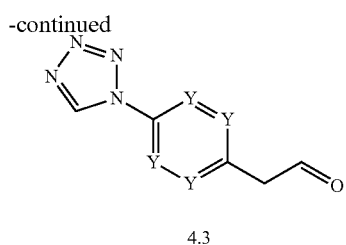

4.3

The epoxides 5.3 (and single enatiomers (R)-5.3 and (S)-5.3) can be prepared following the method detailed in Scheme 5. Treatment of 5.1 (where X is chloride, bromide, iodide, or trifluoromethane sulfonate) with commercially available potassium vinyl trifluoroborate (Molander, G.; Luciana, A. Journal of Organic Chemistry, 2005, 70(10), 3950-3956) under palladium catalyzed coupling conditions with an appropriate phosphine ligand gives rise to styrene 5.2 (Molander, G.; Brown, A. Journal of Organic Chemistry, 2006, 71(26), 9681-9686). Alternatively, other methods may be employed, for example, using vinylstannane reagents and palladium catalysis. The resulting styrenes 5.2 can be converted to the corresponding epoxides 5.3 under various epoxidation conditions, for example, with m-CPBA (Fringuelli, F. et al. Organic Preparations and Procedures International, 1989, 21(6), 757-761). The racemic epoxide 5.3 can be resolved under chiral HPLC chromatography conditions to afford its enantiomers (R)-5.3 and (S)-5.3), which can be used in place of 1.1 according to Scheme 1.

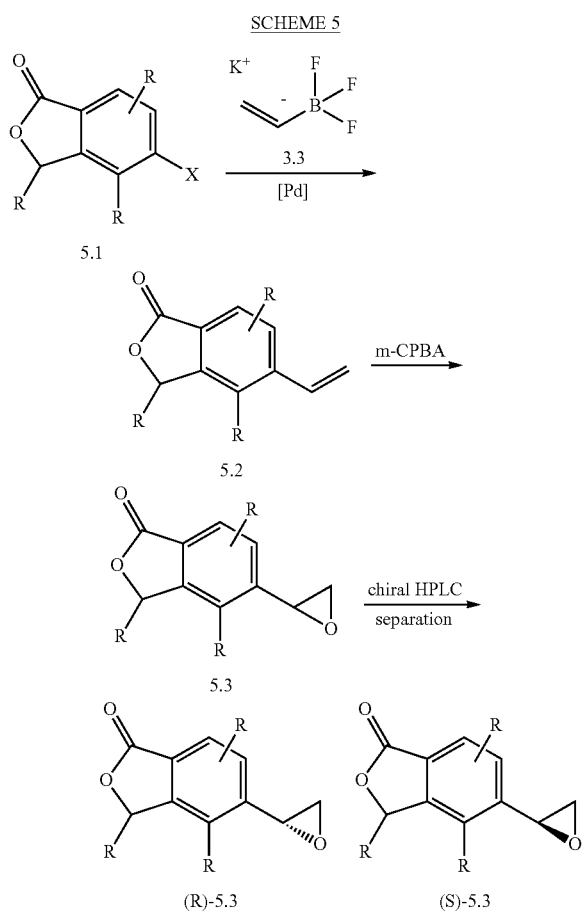

Alternatively, enantiopure epoxides (R)-5.3 or (S)-5.3 can be prepared as shown in Scheme 6. Treatment of 5.1 (where X is bromide, iodide, or trifluoromethane sulfonate) with commercial available vinyl butylether 6.1 under palladium catalyzed conditions with a suitable ligand (for example Pd(OAc)$_2$, DPPP) can provide the enol ethers 6.2. Enol ethers may be prepared using other methods known to the chemist. Treatment of the resulting enol ethers 6.2 with NBS or other similar reagents affords the corresponding bromomethyl ketones 6.3. These can be subjected to a variety of asymmetric ketone reduction conditions, for example with an enzyme that can affect such a transformation with high enantioselectivity. Subsequent treatment with a base such as triethylamine leads to cyclization, affording the enantioenriched epoxides (R)-5.3 or (S)-5.3 (depending upon the asymmetric reducing agent).

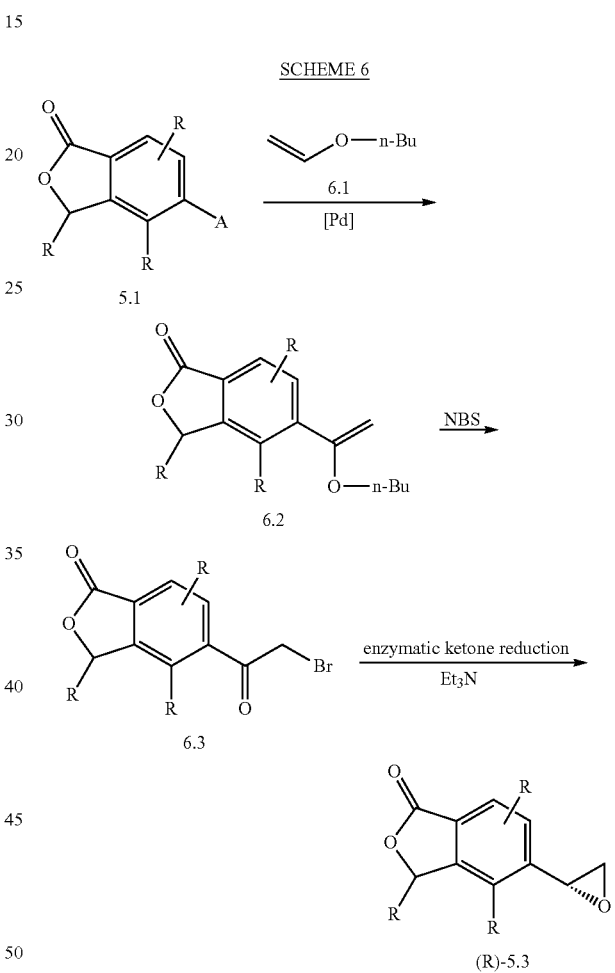

Aldehydes 7.2 may be prepared in numerous ways, with two approaches described in Scheme 7. Treatment of 5.1 (where X is bromide, iodide, or trifluoromethane sulfonate) with bromo(1,3-dioxolan-2-ylmethyl)zinc in the presence of an appropriate palladium catalyst and ligand, such as palladium(II) acetate and tri-t-butylphosphine-BF$_4$ complex, provides the corresponding aryl 1,3-dioxolan-2-ylmethyl derivative 7.1A. Then the aldehydes 7.2 may be obtained by treatment with HCl in the presence of water and an organic solvent. Alternatively, reaction of 5.1 (where X is bromide, iodide, or trifluoromethane sulfonate) with allyltributylstannane in the presence of palladium catalyst affords the allyl product 7.1. Oxidation, for example with ozone, followed by dimethyl sulfide, provides aldehydes 7.2.

SCHEME 7

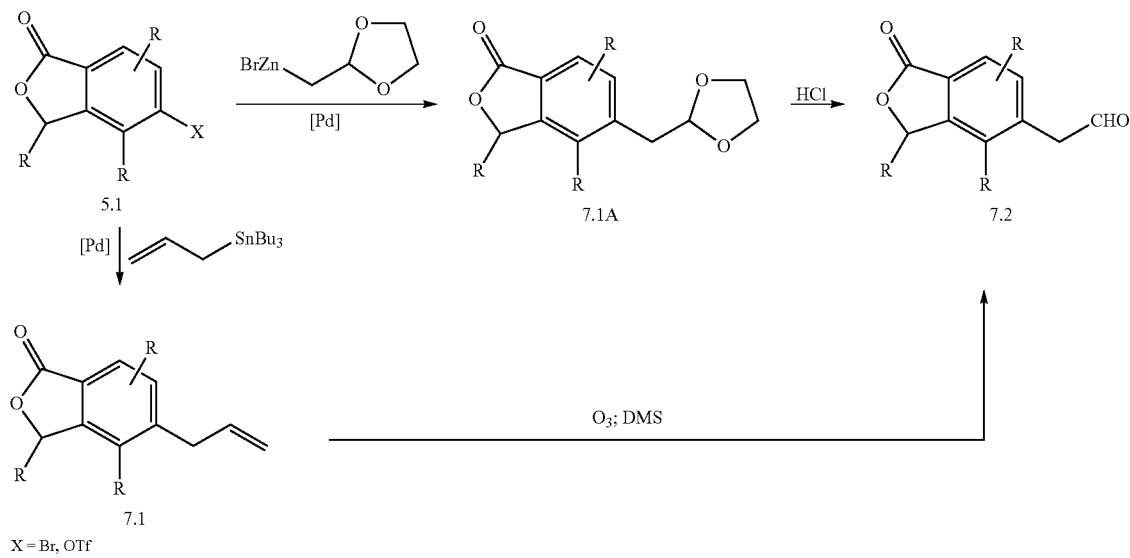

X = Br, OTf

Spirocyclic aminofuranones 8.4 can be prepared as described in Scheme 8. Spirocyclic diamines, amino lactams or aminocarbamates 8.1, where an amine is protected as appropriate (Greene, T.; Wuts, P. G. M. *protective Groups in Organic Synthesis*, John Wiley and Sons, Inc., New York, N.Y. 1991), can be coupled to furanone triflates or bromides 8.2 using a palladium catalyst and ligand, for example palladium acetate and 4,5-Bis(diphenylphosphino)-9,9-dimethylxanthene. Some spirocyclic diamines, amino lactams or aminocarbamates 8.1 described herein are commercially available; others can prepared as described in the experimental section below. 4-Bromofuran-2(5H)-one is commercially available; other furanones 8.2 can be prepared as described in the examples below. Intermediates 8.3 are converted to spirocyclic aminofuranones 8.4 by removal of the protective group, for example, tert-butoxycarbonyl can be removed with TFA or HCl.

SCHEME 8

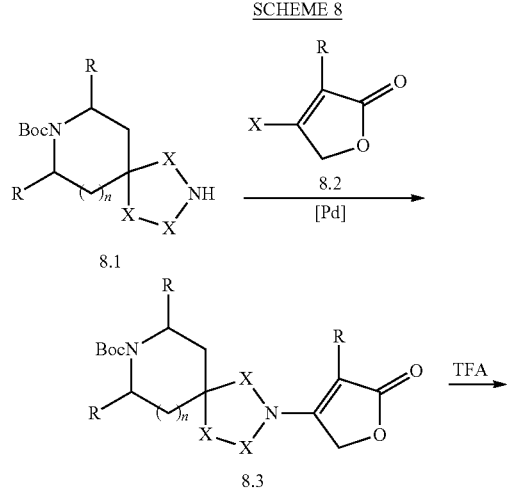

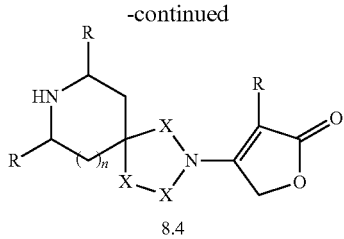

X = Br, OTf

Methods for the synthesis of spirocyclic diamines, amino lactams or aminocarbamates 8.1 are varied and are detailed in the experimental section below. One general method for preparing spiromorpholinones 9.5 is depicted in Scheme 9 below. According to the Scheme, the commercially available alcohol 9.1 can be alkylated with an allyl halide (such as allyl bromide as shown) to provide 9.2. Oxidative cleavage of the alkene 9.2 with, for example, $OsO_4$ and $NaIO_4$, affords the aldehyde 9.3. Reductive mination of the aldehyde with dibenzylamine using, for example, $NaB(OAc)_3H$ or $NaBH_3CN$ as reducing agents, provides aminoalcohols 9.4. Hydrogenolysis of 9.4 removes the benzyl groups with concomitant cyclization to form the morpholinone spirocyclic ring system 9.5. Hydrogenolysis can be achieved in a number of ways, including by using hydrogen gas in the presence of a catalyst such as palladium over carbon. Spiromorpholinones 9.5 can be used in place of 8.1 in Scheme 8 to afford the furanone coupled intermediates 8.4.

SCHEME 9

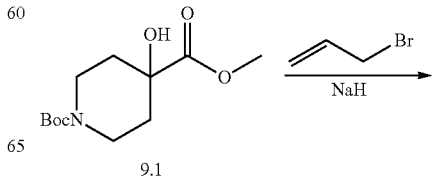

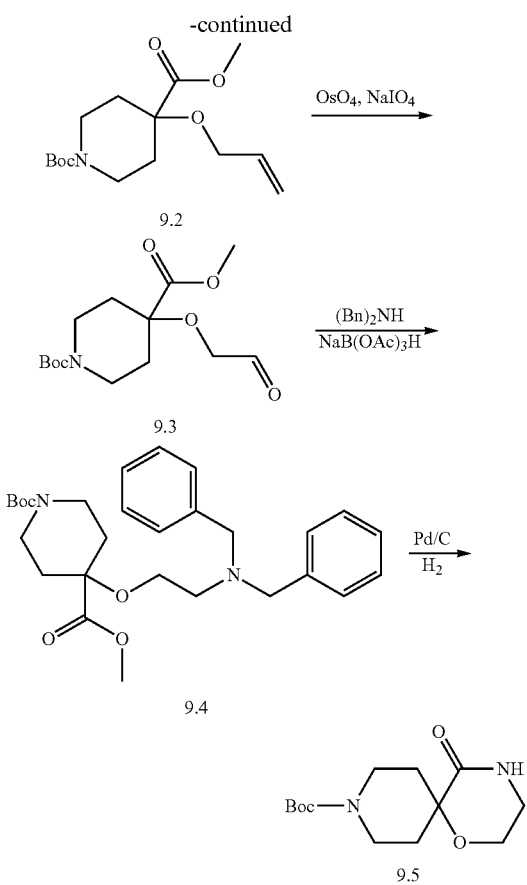

The independent synthesis of diastereomers and enantiomers or their chromatographic separations may be achieved as known in the art by appropriate modification of the methodology disclosed herein. Their absolute stereochemistry may be determined by x-ray crystallography of crystalline products or crystalline intermediates which are derivatized, if necessary, with a reagent containing an asymmetric center of known absolute stereochemistry, or by vibrational circular dichroism (VCD) spectroscopy.

The subject compounds may be prepared by modification of the procedures disclosed in the Examples as appropriate. Starting materials are commercially available or made by known procedures or as illustrated.

Reactions sensitive to moisture or air were performed under nitrogen or argon using anhydrous solvents and reagents. The progress of reactions was determined by either analytical thin layer chromatography (TLC) usually performed with E. Merck pre-coated TLC plates, silica gel 60F-254, layer thickness 0.25 mm or liquid chromatography-mass spectrometry (LC-MS).

Typically the analytical LC-MS system used consisted of a WATERS ZQ platform with electrospray ionization in positive ion detection mode with an Agilent 1100 series HPLC with autosampler. The column was usually a WATERS XTERRA MS C18, 3.0×50 mm, 5 µm. The flow rate was 1 mL/min, and the injection volume was 10 µL. UV detection was in the range 210-400 nm. The mobile phase consisted of solvent A (water plus 0.05% TFA) and solvent B (acetonitrile plus 0.05% TFA) with a gradient of 100% solvent A for 0.7 min changing to 100% solvent B over 3.75 min, maintained for 1.1 min, then reverting to 100% solvent A over 0.2 min.

Preparative HPLC purifications were usually performed using a mass spectrometry directed system. Usually they were performed on a WATERS Chromatography Workstation configured with an LC-MS System consisting of: WATERS ZQ single quad MS system with Electrospray Ionization, WATERS 2525 Gradient Pump, WATERS 2767 Injector/Collector, WATERS 996 PDA Detector, the MS Conditions of: 150-750 amu, Positive Electrospray, Collection Triggered by MS, and a WATERS SUNFIRE C-18 5 micron, 30 mm (id)×100 mm column. The mobile phases consisted of mixtures of acetonitrile (10-100%) in water containing 0.1% TFA. Flow rates were maintained at 50 mL/min, the injection volume was 1800 µL, and the UV detection range was 210-400 nm. Mobile phase gradients were optimized for the individual compounds.

Reactions performed using microwave irradiation were normally carried out using an Emrys Optimizer manufactured by Personal Chemistry, or an Initiator manufactured by BIOTAGE.

Concentration of solutions was carried out on a rotary evaporator under reduced pressure. Flash chromatography was usually performed using a BIOTAGE Flash Chromatography apparatus (Dyax Corp.) on silica gel (32-63 mM, 60 Å pore size) in pre-packed cartridges of the size noted. $^1$H NMR spectra were acquired at 500 MHz spectrometers in CDCl$_3$ solutions unless otherwise noted. Chemical shifts were reported in parts per million (ppm). Tetramethylsilane (TMS) was used as the internal reference in CDCl$_3$ solutions, and residual CH$_3$OH peak or TMS was used as the internal reference in CD$_3$OD solutions. Coupling constants (J) were reported in hertz (Hz).

Chiral analytical chromatography was usually performed on one of CHIRALPAK AS, CHIRALPAK AD, CHIRALCEL OD, CHIRALCEL IA, or CHIRALCEL OJ columns (250×4.6 mm) (Daicel Chemical Industries, Ltd.) with noted percentage of either ethanol in hexane (% Et/Hex) or isopropanol in heptane (% IPA/Hep) as isocratic solvent systems. Chiral preparative chromatography was sometimes conducted on one of CHIRALPAK AS, CHIRALPAK AD, CHIRALCEL OD, CHIRALCEL IA, or CHIRALCEL OJ columns (20×250 mm) (Daicel Chemical Industries, Ltd.) with desired isocratic solvent systems identified on chiral analytical chromatography or by supercritical fluid (SFC) conditions. Alternatively, chiral preparative chromatography was conducted by supercritical fluid (SFC) conditions using one of CHIRALPAK AS, CHIRALPAK AD-H, CHIRALCEL OD-H, CHIRALPAK IC, or CHIRALCEL OJ-H columns (250×21.2 mm) (Daicel Chemical Industries, Ltd.). Where retention times are provided in the Examples and Tables, they are not intended to be a definitive characteristic of a particular compound since, as known to those skilled in the art, retention times will vary and the timing and/or order of peak elution may change depending on the chromatographic conditions, such as the column used, the condition of the column, and the solvent system and instruments used.

Flash chromatography was carried out on silica gel (230-400 mesh). NMR spectra were obtained in CDCl$_3$ solution unless otherwise noted. Coupling constants (J) are in hertz (Hz).

Abbreviations used herein include: —C(O)CH$_3$ (Ac); —OC(O)CH$_3$ (OAc); ethyl acetate (EtOAc), benzyloxycarbonyl (Cbz); dibenzylideneacetone (dba); 11-chloroethylchloroformate (ACE-Cl); phenyl (Ph); dichloromethane (DCM), starting material (SM), diethyl ether (ether or Et$_2$O), trifluoroacetic acid (TFA), triethylamine (TEA), 1,8-Diazabicyclo[5.4.0]undec-7-ene (DBU); N,N-diisopropylethylamine (DIEA, Hunig's base, DIPEA), dimethylsulfide (DMS); 1-ethyl-3-(3-dimethylaminopropyl), carbodiimide (EDC, EDAC, or EDCI), 2-(7-Aza-1H-benzotriazole-1-yl)-1,1,3,3-tetramethyluronium hexafluorophosphate (HATU), 1-Hydroxybenzotriazole hydrate (HOBt), hexane (Hex); methyl tert-butyl ether (MTBE), Cyclopentyl methyl ether (CPME), 1,3-Bis(diphenylphosphino)propane (DPPP), 2-Dicyclohexylphosphino-2',4',6'-triisopropylbiphenyl (X-Phos), 1,2-dichloroethane (DCE), methanol (MeOH); N-bromo succinimide (NBS), N-chlorosuccinimide (NCS); N-iodosuccinimide (NIS), lithium diisopropylamide (LDA), tetrahydrofuran (THF), Diethylaminosulfur trifluoride (DAST); dimethylsulfoxide (DMSO), isopropanol (IPA), t-butyloxycarbonyl (Boc or BOC), di-t-butyl dicarbonate (BOC$_2$O, Boc$_2$O), acetic acid (AcOH; HOAc), N;N-dimethylformamide (DMF), 4-dimethylaminopyridine (DMAP), dimethylacetamide (DMA; DMAC); ethylene glycol tetraacetic acid (EGTA); 3-chloroperoxybenzoic acid (mCPBA); nicotinamide adenine dinucleotide phosphate (NADP), petroleum ether (PE), lithium aluminum hydride (LAH), di-isopropylamine (DIPA), Carbonyldiimidazole (CDI), p-toluenesulfonic acid (TsOH), p-toluene-SO$_2$— (tosyl or Ts), methane sulfonyl chloride or mesyl chloride (Ms-Cl), methanesulfonic acid (MsOH), CH$_3$SO$_2$-(mesyl or Ms), dimethoxyethane (DME), 1,1'-bis(diphenylphosphino) ferrocene (dppf, DPPF); Pd(dppf)Cl$_2$ or PdCl$_2$(dppf) is 1,1'-Bis(diphenylphosphino)ferrocene]dichloropalladium(II) which may be complexed with CH$_2$Cl$_2$, (Oxydi-2,1-phenylene)bis(diphenylphosphine) (DPEPhos); hexamethylphosphoramide (HMPA); isopropyl acetate (IPAc); N-methylmorpholine-N-oxide (NMO); tetrakis(triphenylphosphine) palladium (Pd(PPh$_3$)$_4$); tris(dibenzylidineacetone) dipalladium (Pd$_2$(dba)$_3$); Diethylaminodifluorosulfinium tetrafluoroborate (XtalFluor-E); 4,5-Bis(diphenylphosphino)-9,9-dimethylxanthene (Xantphos); N,N,N',N'-Tetramethylethylenediamine (TMEDA); [1,4-Bis(diphenylphosphino)butane](1,5-cyclooctadiene)rhodium(I) tetrafluoroborate (Rh(COD)BF$_4$); round-bottom flask (RB or RBF); aqueous (aq); saturated aqueous (sat'd), saturated aqueous sodium chloride solution (brine); medium pressure liquid chromatography (MPLC), high pressure liquid chromatography (HPLC), flash chromatography (FC); liquid chromatography (LC), supercritical fluid chromatography (SFC); thin layer chromatography (TLC), mass spectrum (ms or MS); liquid chromatography-mass spectrometry (LC-MS or LC/MS), column volume (CV), room temperature (rt, r.t. or RT), hour(s) (h or hr), minute(s) (min), retention time (R$_t$); gram(s) (g); milligram(s) (mg); milliliter(s) (mL); microliter(s) (μL); millimole (mmol). CELITE is a trademark name for diatomaceous earth, and SOLKA FLOK is a trademark name for powdered cellulose. X or x may be used to express the number of times an action was repeated (e.g., washed with 2×200 mL 1N HCl), or to convey a dimension (e.g., the dimension of a column is 30×250 mm).

The following are representative procedures for the preparation of intermediates used to prepare the final products described in the Examples that follow thereafter. These examples are provided for the purpose of further illustration only and are not intended to be limitations on the disclosed invention.

It is understood that a chiral center in a compound may exist in the "S" or "R" stereo-configurations, or as a mixture of both. In many of the examples for intermediate compounds and final compounds, such compounds having a racemic chiral center were separated into individual stereoisomers, for example, referred to as isomer A (or enantiomer A or the like), which refers to the observed faster eluting isomer, and isomer B (or enantiomer B or the like), which refers to the observed slower eluting isomer, and each such isomer may be noted in the example as either the fast or slow eluting isomer. When a single "A" or "B" isomer intermediate is used to prepare a downstream compound, the downstream compound may take the "A" or "B" designation that corresponds to the previously used intermediate. Any Intermediates described below may be referred to herein by their number preceded by "I-" or "Int-." For illustration, in the example titled "Intermediate 3," the racemic parent title compound would be referred to as Intermediate 3 (or I-3), and the separated stereoisomers are noted as Intermediates 3A and 3B (or I-3A and I-3B). In some examples, compounds having a chiral center were derived synthetically from a single isomer intermediate; e.g., Example 4A was made using stereoisomer I-5A. Except for a defined chiral center in a parent isomer mixture, absolute stereochemistry (R or S) of each of the separated isomers was not determined, unless specifically described otherwise. An asterisk (*) may be used in a chemical structure drawing that indicates the location of a chiral center.

INTERMEDIATE 1

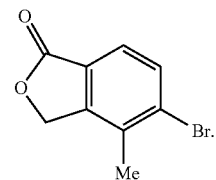

5-bromo-4-methyl-2-benzofuran-1 (3H)-one

Step A: (3-bromo-2-methylphenyl)methanol: To a solution of 3-bromo-2-methyl benzoic acid (35 g, 163 mmol) in THF (200 mL) was added Borane THF Complex (1.0 M, 212 mL, 212 mmol). The mixture was allowed to stir for 24 h. TLC showed one single product spot. The reaction was quenched with water. The solvent THF was removed under reduced pressure. The resulting solid was dissolved in ethyl acetate (500 mL), washed with 1N HCl, sodium carbonate, and brine. The organic layer was dried over sodium sulfate and concentrated to afford (3-bromo-2-methylphenyl)methanol. $^1$H NMR (500 MHz, CDCl$_3$) δ 7.76 (d, J=8.0 Hz, 1H), 7.63 (d, J=8.0 Hz, 1H), 5.30 (s, 2H), 2.42 (s, 3H).

Step B: 5-bromo-4-methyl-2-benzofuran-1(3H)-one

To a flask charged with (3-bromo-2-methylphenyl)methanol (6.0 g, 30 mmol) was added a 1M TFA solution of Thallium Trifluoroacetate (16.2 g, 29.8 mmol). The mixture was stirred at RT overnight. Analysis by TLC showed no starting material remaining. The solvent was removed under vacuum, and the residue was pumped under high vacuum for 30 min to ensure complete removal of TFA. To the residue was then added Palladium(II) Chloride (529 mg, 2.98 mmol), Lithium Chloride (2.53 g, 59.7 mmol), Magnesium Oxide (2.41 g, 59.7 mmol), and MeOH (150 mL). The reaction was flushed with CO twice, and kept under CO at room temperature. Analysis by LC showed a big product spot within 2 hours. To this solution was added ethyl acetate to precipitate the salts. The black solution was filtered through a CELITE pad, washed with EtOAc, adsorbed onto silica and purified by silica gel chromatography to afford title compound. ¹H-NMR (500 MHz, CDCl₃) δ ppm 7.71 (d, J=8.0 Hz, 1H), 7.58 (d, J=8.0 Hz, 1H), 5.25 (s, 2H), 2.37 (s, 3H).

INTERMEDIATE 2

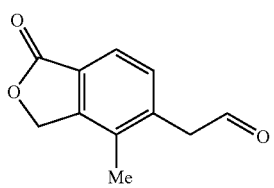

(4-Methyl-1-oxo-1,3-dihydro-2-benzofuran-5-yl)acetaldehyde

Step A: 4-Methyl-5-prop-2-en-1-yl-2-benzofuran-1(3H)-one

To a flask charged with 5-bromo-4-methyl-2-benzofuran-1 (3H)-one (320 mg, 1.409 mmol) and a stir bar was added allyl tri-n-butyltin (0.655 mL, 2.11 mmol), Pd(PPh₃)₄(244 mg, 0.211 mmol), lithium chloride (179 mg, 4.23 mmol), and toluene (15 mL). The reaction was purged with nitrogen 2 times then was heated at reflux for 4 hours. The product was separated by silica gel chromatography to give 4-methyl-5-prop-2-en-1-yl-2-benzofuran-1 (3H)-one.

Step B: (4-Methyl-1-oxo-1,3-dihydro-2-benzofuran-5-yl)acetaldehyde

A solution of the above olefin (220 mg, 1.2 mmol) in MeOH (20 mL) was cooled to −78° C. To this solution was bubbled ozone until the reaction turned blue. Nitrogen was bubbled through the reaction to drive off excess ozone, followed by addition of DMS (0.870 mL, 11.7 mmol). The reaction was allowed to warm up to RT. The crude product was purified by flash chromatography to afford the title compound. ¹H-NMR (500 MHz, CDCl₃) δ ppm 9.78 (s, 1H), 7.75 (d, J=7.5 Hz, 1H), 7.34 (d, J=7.5 Hz, 1H), 5.27 (s, 2H), 3.90 (s, 2H), 2.23 (s, 3H).

INTERMEDIATE 3

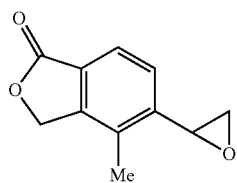

4-methyl-5-oxiran-2-yl-2-benzofuran-1(3H)-one

Step A: 5-ethenyl-4-methyl-2-benzofuran-1(3H)-one

5-Bromo-4-methyl-2-benzofuran-1(3H)-one (598 mg, 4.47 mmol), potassium vinyl trifluoroborate (507 mg, 2.23 mmmol), PdCl₂(dppf)-CH₂Cl₂Adduct (182 mg, 0.223 mmmol), and TEA (0.622 mL, 4.47 mmol) were added to 10 mL ethanol in a 20 mL microwave tube. The tube was sealed and degassed, then heated to 140° C. for 20 min. Analysis by LC-MS showed product peak. The reaction mixture was diluted with ethyl acetate, washed with brine twice, dried and evaporated to dryness. The crude product was purified by MPLC chromatography using a 120 g REDI-SEP column and 0-80% ETOAC/Hexane solvent system to yield 5-ethenyl-4-methyl-2-benzofuran-1(3H)-one. ¹H-NMR (500 MHz, CDCl₃): δ ppm 7.76 (d, J=8 Hz, 1H), 7.03 (dd, J=11, 17 Hz, 1H), 5.84 (d, J=17 Hz, 1H), 5.55 (d, J=11 Hz, 1H), 5.29 (s, 2H), 2.34 (s, 3H); LC-MS: M+1=175;

Step B: 4-methyl-5-oxiran-2-yl-2-benzofuran-1(3H)-one 5-ethenyl-4-methyl-2-benzofuran-1(3H)-one (1.46 g, 8.38 mmol) was added to DCM (25 mL) at 0° C. then mCPBA (2.89 g, 16.8 mmol) was added and the mixture was stirred at RT overnight. The reaction mixture was washed once each with saturated aqueous Na₂S₂O₃, NaHCO₃, and brine. The organic layer was dried over Na₂SO₄, filtered, and evaporated to dryness. The crude material was purified by MPLC chromatography through 120 g REDI-SEP column eluting with 0-80% EtOAc/hexane solvent system to yield target 4-methyl-5-oxiran-2-yl-2-benzofuran-1(3H)-one. ¹H-NMR (500 MHz, CDCl₃): δ ppm 7.77 (d, J=8 Hz, 1H), 7.43 (d, J=8 Hz, 1H), 5.30 (s, 2H), 4.12 (s, 1H), 3.27 (t, J=4 Hz, 1H), 2.735 (dd, J=2.2, 5.5 Hz, 1H), 2.43 (s, 3H). LC-MS: M+1=191.

INTERMEDIATE 3A AND 3B (Method 1)

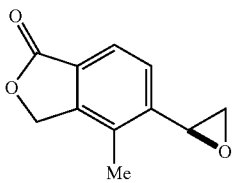 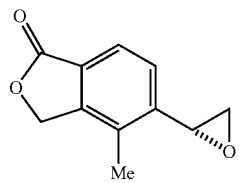

Slow eluting 3A          Fast eluting 3B

3A: 4-methyl-5-[(2S)-oxiran-2-yl]-2-benzofuran-1(3H)-one

3B: 4-methyl-5-[(2R)-oxiran-2-yl]-2-benzofuran-1(3H)-one

Racemic 4-methyl-5-oxiran-2-yl-2-benzofuran-1(3H)-one was resolved on a ChiralPak® AD-H column (5×25 cm) under supercritical fluid chromatography (SFC) conditions on a Berger MGIII preparative SFC instrument. The racemate was diluted to 50 mg/mL in 1:1 DCM:MeOH. The separation was accomplished using 10% EtOH/CO₂, flow rate 200 mL/min, 100 bar, 25° C. 500 ul Injections were spaced every 2.12 mins. The fast epoxide (4-methyl-5-[(2R)-oxiran-2-yl]-2-benzofuran-1(3H)-one, 3B) eluted first, and the slow epoxide (4-methyl-5-[(2S)-oxiran-2-yl]-2-benzofuran-1 (3H)-one, 3A) eluted second.

Alternatively, the resolution could also be achieved using a mobile phase of 8% MeOH/92% CO₂ with a flow rate of 100 mL/min. In that case the sample was prepared by dissolving in methanol, 20 mg/mL, and using a 1 mL volume per injection. After separation, the fractions were dried via rotary evaporator at bath temperature 40° C.

The absolute stereochemistry of each enantiomer was inferred based on the X-ray crystal structure determination of a final compound made with 3B and by Mosher ester and Trost ester HNMR analysis of esters made starting from 3B. Both epoxide isomers find utility in the present invention.

INTERMEDIATE 3B (Method 2)

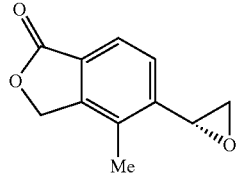

4-methyl-5-[(2R)-oxiran-2-yl]-2-benzofuran-1(3H)-one

StepA: 3-hydroxymethyl-2-methyl phenol

To a 5 L 3 neck RB equipped with overhead stirrer was charged NaBH$_4$ (87.0 g, 2.30 mol) and THF (3.0 L) and the resulting slurry was cooled to 10° C. To the slurry was then added 3-hydroxy-2-methyl benzoic acid (175 g, 1.15 mol) portionwise over 20 min (Tmax 17° C.). A stirrable slurry formed, and was aged for an additional 45 min at 10-15° C. after which BF$_3$—OEt$_2$ (321 mL, 2.53 mol) was added slowly over 1.5 hours. The slurry was aged at 10° C.-15° C. for 2 h then assayed for reaction completion (98.5% conversion). The slurry was cooled to <10° C. and quenched with 931 mL MeOH slowly over 1.5 h (gas evolution). The resulting slurry was aged overnight at RT. The batch was cooled to <10° C. then quenched with 1 N HCl (1.5 L) to get a homogeneous solution (pH solution~1), which was aged for 30 min and then the organic solvents were removed by rotary evaporation to approximately 1.8 L of total reaction volume (bath temperature was set to 50° C.; internal temp of concentrate after rotary evaporation was ~40° C.). The slurry was held at 45° C. for 30 min then cooled slowly to 15° C. The solids were filtered and washed with cold (15° C.) water (2×300 mL), providing 3-hydroxymethyl-2-methyl phenol. $^1$H-NMR (400 MHz, DMSO-d$_6$): δ 9.11 (s, 1H), 6.95 (t, J=7.8 Hz, 1H), 6.82 (d, J=7.4 Hz, 1H), 6.71 (d, J=7.8 Hz, 1H), 4.93 (t, J=5.5 Hz, 1H), 4.44 (d, J=5.5 Hz, 2H), 2.06 (s, 3H).

Step B: 4-Bromo-3-hydroxymethyl-2-methyl phenol

3-Hydroxymethyl-2-methyl phenol (113.9 g, 824.0 mmol) was dissolved in a mixture of acetonitrile (850 mL) and trifluoroacetic acid (750.0 mL, 9,735 mmol) in a 3-neck 5-L flask under nitrogen. The reaction mixture was cooled to −33° C. N-bromosuccinimide (141 g, 791 mmol) was added over 15 minutes, with the temperature during addition in the range of −35 to −33° C. The reaction mixture was allowed to stir for an additional 15 min during which time the temperature decreased to −40° C. The cooling bath was removed, and potassium carbonate (741.0 g, 5,358 mmol) diluted with water to a total of 1.0 L was added. Off-gassing was observed, and the temperature increased to 25° C. MTBE (1.5 L) was added, and the reaction mixture was transferred to a separatory funnel. The layers were separated. The aqueous layer was diluted with water (500 mL) and extracted with MTBE (1 L)+EtOAc (500 mL), and then MTBE (500 mL)+EtOAc (250 mL). The combined organic layers were washed with water (240 mL) and dried over sodium sulfate. The sodium sulfate was removed by filtration, washed with additional MTBE and concentrated under reduced pressure. MTBE (684 mL, 2 volumes) was added, and the suspension was heated to 40° C. to produce a homogeneous solution. The solution was allowed to cool to room temperature. Six volumes of heptane were added, and the supension was stirred overnight. The suspension was filtered, and the crystals were washed with 4:1 heptane: MTBE (500 mL), followed by heptane (500 mL). The solid was dried under vacuum, providing 4-bromo-3-hydroxymethyl-2-methyl phenol. $^1$H NMR (400 MHz, DMSO-d$_6$): δ 9.52 (s, 1H), 7.21 (d, J=8.6 Hz, 1H), 6.71 (d, J=8.6 Hz, 1H), 4.88 (t, J=5.1 Hz, 1H), 4.59 (d, J=5.1 Hz, 2H), 2.23 (s, 3H)

Step C:
5-Hydroxy-4-methyl-3H-isobenzofuran-1-one

To a 2 L 3 neck flask equipped with overhead stirrer, N$_2$ inlet, and condenser were charged 4-bromo-3-hydroxymethyl-2-methyl phenol (100 g, 461 mmol), CuCN (83.0 g, 921 mmol), and DMF (500 mL). The solution was sparged with N$_2$ for 15 min then heated to 145° C. to obtain a homogeneous solution. The solution was aged at 145° C. for 2 h, then the reaction mixture was cooled to 95° C. 41.5 mL water was added (sparged with N$_2$), and the reaction aged for 20 h. The reaction was cooled to RT then the solids filtered through SOLKA FLOK and the cake washed with 50 mL DMF. To a 3 L flask containing 1 L EtOAc was added the DMF filtrate. A precipitate coating formed in bottom of flask. The DMF/EtOAc suspension was filtered through SOLKA FLOK and the cake was washed with 250 mL EtOAc. The resulting filtrate was washed with 5% brine solution (3×500 mL). The aqueous layers were extracted with 500 mL EtOAc and the combined organics were dried over MgSO4, filtered and evaporated. The solids were slurried in 250 mL MTBE at RT then filtered and washed with 100 mL MTBE. The solids were dried under vacuum at RT, providing 5-hydroxy-4-methyl-3H-isobenzofuran-1-one. $^1$H NMR (400 MHz, DMSO-d$_6$): δ 10.52 (s, 1H), 7.51 (d, J=8.3 Hz, 1H), 6.99 (d, J=8.3 Hz, 1H), 5.28 (s, 2H), 2.07 (s, 3H).

Step D:
4-methyl-1-oxo-1,3-dihydroisobenzofuran-5-yl trifluoromethanesulfonate

5-Hydroxy-4-methyl-3H-isobenzofuran-1-one (46.8 g, 285 mmol) was suspended in dichloromethane (935 mL) in 2-L roundbottom flask equipped with overhead stirrer under nitrogen. Triethylamine (59.5 mL, 427 mmol) was added, and the reaction mixture was cooled in an ice bath to 3.8° C. Trifluoromethanesulfonic anhydride (67.4 mL, 399 mmol) was added via addition funnel over 50 min, keeping the temperature<10° C. After stirring the reaction mixture for an additional 15 min, the reaction mixture was quenched with water (200 mL), then stirred with DARCO® KB (activated carbon, 25 g) for 15 min. The biphasic mixture was filtered over SOLKA FLOK, washing with additional dichloromethane, and transferred to a separatory funnel, whereupon it was diluted with additional water (300 mL). The layers were separated, and the organic layer was washed with water (500 mL) and 10% brine (200 mL). The dichloromethane solution was dried over sodium sulfate, filtered and evaporated. The solid was adsorbed onto silica gel (27.5 g) and eluted through a pad of silica gel (271 g) with 25% ethyl acetate/hexanes. The resulting solution was concentrated under vacuum with the product crystallizing during concentration. The suspension was filtered, the solid washed with heptane and dried under vacuum and nitrogen, providing trifluoromethanesulfonic acid 4-methyl-1-oxo-1,3-dihydro-isobenzofuran-5-yl ester. $^1$H NMR (400 MHz, CDCl$_3$): δ 7.87 (d, J=8.4 Hz, 1H), 7.47 (d, J=8.4 Hz, 1H), 5.32 (s, 2H), 2.41 (s, 3H)

Step E: 5-(1-Butoxy-vinyl)-4-methyl-3H-isobenzofuran-1-one

To a 1 L 3-neck was charged trifluoromethanesulfonic acid 4-methyl-1-oxo-1,3-dihydro-isobenzofuran-5-yl ester (63.0 g, 213 mmol), DMF (315 mL), butyl vinyl ether (138 mL, 1063 mmol)) then Et$_3$N (35.6 mL, 255 mmol). The solution was sparged with N$_2$ for 20 min. To the solution was added Pd(OAc)$_2$ (1.19 g., 5.32 mmol) and DPPP (2.41 g., 5.85 mmol) and sparged for an additional 10 min then heated to 80° C. After a 1 hr age, the solution was cooled to <10° C. then quenched with 630 mL EtOAc and washed with 5% NH$_4$Cl (2×315 mL), 10% brine (2×315 mL), dried over MgSO$_4$, filtered, concentrated by rotary evaporation and flushed with EtOAc (3×100 mL) to remove excess butyl vinyl ether, providing crude 5-(1-butoxy-vinyl)-4-methyl-3H-isobenzofuran-1-one. $^1$H NMR (400 MHz, DMSO-d$_6$): δ 7.67 (d, J=7.7 Hz, 1H), 7.48 (d, J=7.7 Hz, 1H), 5.42 (s, 2H), 4.54 (d, J=2.3 Hz, 1H), 4.27 (d, J=2.3 Hz, 1H), 3.85 (t, J=6.4 Hz, 2H), 2.27 (s, 3H), 1.71-1.64 (m, 2H), 1.46-1.37 (m, 2H), 0.92 (t, J=7.4 Hz, 3H)

Step F: 5-(2-Bromo-acetyl)-4-methyl-3H-isobenzofuran-1-one

To a 1 L 3-neck flask equipped with overhead stirrer was added crude 5-(1-butoxy-vinyl)-4-methyl-3H-isobenzofuran-1-one (55.8 g) and THF (315 mL). The solution was cooled to <5° C. after which water (79 mL) was added and the solution was maintained at <5° C. NBS (41.6 g) was then added portion-wise while maintaining Tmax=19° C. The solution was then warmed to RT for 30 minutes. HBr (48%, 0.241 mL) was added and the reaction was aged at RT for approximately 1 h after which 236 mL water was then added to the batch. A water bath is used to maintain temp at 20° C. Another 315 mL of water was added (solvent composition 1:2 THF:water) and the slurry was cooled to 15° C. The resulting solids were filtered and washed with cold 1:2 THF:water (15° C.): 150 mL displacement wash followed by 100 mL slurry wash. The solids were dried under vacuum at RT to provide 5-(2-bromo-acetyl)-4-methyl-3H-isobenzofuran-1-one. $^1$H NMR (400 MHz, DMSO-d$_6$): δ 7.99 (d, J=7.8 Hz, 1H), 7.82 (d, J=7.8 Hz, 1H), 5.49 (s, 2H), 4.92 (s, 2H), 2.33 (s, 3H)

Step G: 4-methyl-5-[(2R)-oxiran-2-yl]-2-benzofuran-1(3H)-one 5-(2-Bromo-acetyl)-4-methyl-3H-isobenzofuran-1-one (48.8 g., 181 mmol) was charged to a 5 L 3 neck round bottom equipped with overhead stirrer, thermocouple, and heating mantle. 2-Propanol (1.22 L) was added, followed by 610 mL of pH 7 0.1M potassium phosphate buffer. Buffer solution (610 mL) was charged to a 1.0 L erlenmeyer, and 2.44 g of NADP was added to the erlenmeyer and swirled to dissolve. A reducing enzyme, KRED MIF-20 (2.44 g) (available from Codexis, Inc., 200 Penobscot Drive, Redwood City, Calif. 94063, www.codexis.com, tel. 1-650-421-8100) was added to the erlenmeyer flask and the mixture was swirled to dissolve the solids. The resulting solution was added to the 5 L round bottom, which was then heated to 28° C. and aged for 6 hours, at which point the reaction was cooled to RT and triethylamine (50.2 mL, 360 mmol) was added. The resulting solution was aged at 40° C. for 1 h. The light slurry solution was cooled to RT, after which 122 g NaCl was added. The solution was aged at RT then extracted with 1.22 L isopropyl acetate (IPAc). The aqueous layer was re-extracted with 400 mL IPAc and the combined organics were washed with 400 mL 20% brine solution, dried over MgSO$_4$, filtered and concentrated by rotary evaporation. The resulting solids were taken up in 100 mL IPAc (thick slurry). Hexanes were added (400 mL) and the suspension aged at RT then filtered and washed w/ 5:1 Hexanes:IPAc solution (150 mL). The crystalline solids were dried under vacuum at RT to provide 4-methyl-5-[(2R)-oxiran-2-yl]-2-benzofuran-1(3H)-one. 1H NMR (400 MHz, CDCl$_3$): δ 7.75 (d, J=8.1 Hz, 1H), 7.42 (d, J=8.1 Hz, 1H), 5.28 (s, 2H), 4.10 (dd, J=4.0, 2.8, 1H), 3.26 (dd, J=5.6, 4.0, 1H), 2.72 (dd, J=5.6, 2.8, 1H), 2.42 (s, 3H).

INTERMEDIATE 4

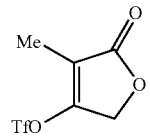

4-methyl-5-oxo-2,5-dihydrofuran-3-yl trifluoromethanesulfonate

Step A: ethyl 4-bromo-2-methyl-3-oxobutanoate

To the solution of ethyl 2-methyl-3-oxobutanoate (5.05 g, 35.0 mmol) in water (10 mL) at 0° C. was added bromine (1.805 mL, 35.0 mmol) dropwise over 2 h. The resulting solution was stirred at rt for 16 h. The reaction mixture was extracted with ethyl acetate, the organic phase was dried over sodium sulfate, and concentrated to give ethyl 4-bromo-2-methyl-3-oxobutanoate. $^1$HNMR (500 MHz, CDCl$_3$), δ4.322-4.274 (m, 2H), 2.455 (s, 2H), 1.991 (s, 3H), 1.337-1.309 (t, 3H).

Step B: 4-hydroxy-3-methylfuran-2(5H)-one

Ethyl 4-bromo-2-methyl-3-oxobutanoate (7.81 g, 35 mmol) was treated with hydrogen bromide (0.040 mL, 48%, 0.35 mmol) and the mixture was heated at 100° C. for 6 h. The precipitate was collected by filtration followed by washing with ethyl acetate to give 4-hydroxy-3-methylfuran-2(5H)-one. $^1$HNMR (500 MHz, CDCl$_3$), δ4.595 (s, 2H), 3.314 (s, 1H), 1.668 (s, 3H).

Step C: 4-methyl-5-oxo-2,5-dihydrofuran-3-yl trifluoromethanesulfonate

To the solution of 4-hydroxy-3-methylfuran-2(5H)-one (400 mg, 3.51 mmol) in dichloromethane (10 mL) at −78° C. was added 2,6-lutidine (0.612 mL, 5.26 mmol) and triflic anhydride (0.711 mL, 4.21 mmol) dropwise. The reaction temperature was maintained at −78° C. for 0.5 h before being warmed to rt for 1 h. The mixture was diluted with DCM (100 mL) and washed with 1 N hydrogen chloride (3 times 100 mL), then with diluted sodium bicarbonate solution, then dried over sodium sulfate, and concentrated to give 4-methyl-5-oxo-2,5-dihydrofuran-3-yl trifluoromethanesulfonate. LC/MS: (M+1)$^+$: 247.0.

INTERMEDIATE 5

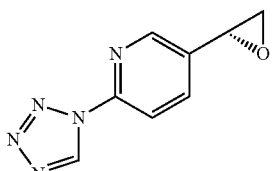

5A

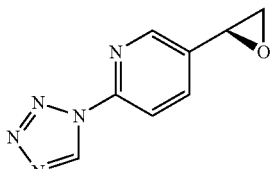

5B (R)-5-(Oxiran-2-yl)-2-(1H-tetrazol-1-yl)pyridine (5A) and (S)-5-(Oxiran-2-yl)-2-(1H-tetrazol-1-yl)pyridine (5B)

Step A: 5-Bromo-2-(1H-tetrazol-1-yl)pyridine

To a solution of 5-bromopyridin-2-amine (5.0 g, 28.9 mmol) in acetic acid (40 mL, 699 mmol) was added (diethoxymethoxy) ethane (7.70 mL, 46.2 mmol), followed by sodium azide (2.82 g, 43.3 mmol). The mixture was heated at 80° C. for 1 h, cooled to room temperature and diluted with water. Precipitate was collected by filtration and dried under high vacuum to provide the title compound.

Step B: 5-Ethenyl-2-(1H-tetrazol-1-yl)pyridine

To a stirring solution of 5-bromo-2-(1H-tetrazol-1-yl)pyridine (1.0 g, 4.42 mmol), in EtOH (70 mL) was added bis[(diphenylphosphino)ferrocene]dichloropalladium(II), complex with dichloromethane (0.361 g, 0.442 mmol), potassium vinyl trifluoroborate (1.18 g, 8.85 mmol, 2 equiv.), triethylamine (1.23 mL, 8.85 mmol, 2 equiv), and water (0.5 mL). The reaction mixture was heated at reflux (90° C., oil bath) under $N_2$. Upon completion (1-2 h) as determined by reverse phase HPLC-MS and TLC (eluent: 10% ethyl acetate in hexane), the mixture was cooled to room temperature, and then diluted with water. The organic layer was separated, and the aqueous layer was extracted with EtOAc. The combined organic layers were washed with brine, dried over $MgSO_4$, and concentrated. The crude material was chromatographed over a column of $SiO_2$ (0-20% EtOAc in hexane as eluent). Evaporation of the solvent yielded the title compound. LCMS $[M+1]^+=174.0$.

Step C: 5-(Oxiran-2-yl)-2-(1H-tetrazol-1-yl)pyridine (5)

To a solution of 5-ethenyl-2-(1H-tetrazol-1-yl)pyridine (0.664 g, 3.83 mmol) in a 2:1 ratio of $H_2O$:t-BuOH (30 mL) was added N-bromosuccinimide (0.751 g, 4.22 mmol) in portions over 5 min. The mixture was heated at 40° C. for 1 h, cooled to 5° C., made basic with sodium hydroxide aqueous solution (0.46 g in 5 mL of $H_2O$, 11.50 mmol), stirred for another 1 h at the same temperature, and poured into $H_2O$ (10 mL). The product precipitated out. The solid was collected by filtration, washed with water, and dried in vacuo. $^1$H NMR (500 MHz, DMSO-$d_6$), δ 10.17 (s, 1H), 8.60 (d, J=1.4 Hz, 1H), 8.04-7.99 (m, 2H), 4.14 (dd, J=2.7 Hz, J=2.8 Hz, 1H), 3.23 (t, J=4.6 Hz, 1H), 3.02 (dd, J=25 Hz, 1H); LCMS $[M+1]^+=190$. Further chiral separation (CHIRALPAK AD-H 30×250 mm, 50% MeOH/$CO_2$, 70 mL/min, 100 bar, 46 mg in MeOH/DCM) afforded faster eluted 5A (R)-5-(oxiran-2-yl)-2-1H-tetrazol-1-yl)pyridine and slower eluted 5B (S)-5-(oxiran-2-yl)-2-(1H-tetrazol-1-yl)pyridine. Absolute chemistry was determined by using Vibrational Circular Dichroism (VCD) spectroscopy with high confidence. Analysis was done comparing experimental data to the calculated VCD and IR spectra of the (R) and (S) compounds.

INTERMEDIATES 6A and 6B

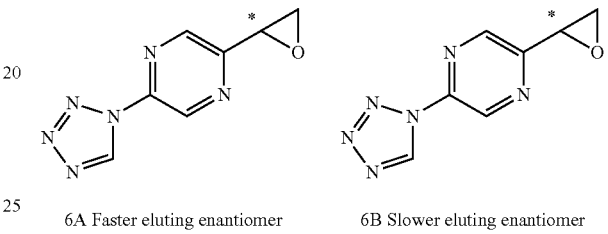

6A Faster eluting enantiomer   6B Slower eluting enantiomer (R)-2-(Oxiran-2-yl)-5-(1H-tetrazol-1-yl)pyrazine and (S)-2-(Oxiran-2-yl)-5-(1H-tetrazol-1-yl)pyrazine Step A: 2-Bromo-5-(1H-tetrazol-1-yl)pyrazine To a solution of 5-bromopyrazin-2-amine (10.75 g, 57.5 mmol) in ethyl acetate (150 ml) was added trimethylsilyl 2,2,2-trifluoroacetate (16.88 ml, 98 mmol). After the mixture was stirred for 5 min, triethoxymethane (17.21 ml, 103 mmol) was added. The resulting mixture was stirred for another five min, and this was followed by addition of azidotrimethylsilane (12.09 ml, 92 mmol). Stirring continued at rt for 2 days, and the mixture was concentrated under reduced pressure. Recrystallization of the residue from ethyl acetate afforded 2-bromo-5-(1H-tetrazol-1-yl)pyrazine. LCMS $[M+2+1]^+=228.9$.

Step B: 2-(1H-Tetrazol-1-yl)-5-vinylpyrazine

A solution of 2-bromo-5-(1H-tetrazol-1-yl)pyrazine (11.2 g, 49.3 mmol), potassium vinyltrifluoroborate (13.22 g, 99.0 mmol), 1,1'-bis(diphenylphosphino)ferrocene-palladium(ii) dichloride dichloromethane complex (2.01 g, 2.47 mmol), and TEA (13.75 ml, 99.0 mmol) in ethanol (150 ml) heated at reflux at 82° C. for 4 h. The reaction mixture was cooled to rt, and the precipitate was filtered off. The filtrate was concentrated, and the residue was purified by flash chromatography (Biotage, Si, ethyl acetate in hexane: 35 to 45%) affording 2-(1H-tetrazol-1-yl)-5-vinylpyrazine LCMS $[M+1]^+=175.10$. The filter cake was stirred in DCM (50 mL), and the solid was filtered off. The filtrate was concentrated to afford more 2-(1H-tetrazol-1-yl)-5-vinylpyrazine.

Step C: 2-(Oxiran-2-yl)-5-(1H-tetrazol-1-yl)pyrazine

To a suspension of 2-(1H-tetrazol-1-yl)-5-vinylpyrazine (6.7 g, 38.5 mmol) in t-BuOH:water (96 ml: 190 ml) was added N-bromosuccinimide (7.53 g, 42.3 mmol) in portions at rt. The mixture was heated at 50° C. for 1 h, and cooled to 0° C. in an ice bath. NaOH (4.61 g in 30 mL water, 115 mmol) was added dropwise, and the resulting mixture was stirred at the same temperature for 20 min. The product was collected by filtration, washed with water, dried under vacuum to give 2-(1H-tetrazol-1-yl)-5-vinylpyrazine LCMS [M+1]$^+$=191.07. Chiral separation (CHIRALPAK AD-H 30×250 mm, 50% MeOH/CO$_2$, 70 mL/min, 100 bar, MeOH/DCM) afforded faster eluted isomer 6A and slower eluted isomer 6B. LCMS [M+1]$^+$=191.1. Both isomers were useful for the preparation of potent ROMK inhibitors.

The following epoxide intermediates in Table 1 were prepared employing a similar synthetic method as that described for Intermediates 5, 5A, 5B or 6, 6A, 6B. Column 2 shows the structure of the starting material followed by the method used (either I-5 for the procedure described for Intermediate 5, or I-6 for the procedure described for Intermediate 6). Note that the absolute stereochemistry was not determined unambiguously for these intermediates. Both isomers were useful for the preparation of potent ROMK inhibitors.

TABLE 1

Epoxides prepared using the method described for I-5 or I-6

| Intermediate No. | Column 2 | Structure and name | Structure and name | LC-MS [M + 1]$^+$ |
| --- | --- | --- | --- | --- |
| 7 | (NH$_2$-, Br-pyridine); Method: I-5 | Fast eluted 7A | Slow eluted 7B | 190.10 |
| 8 | (Br, Me, NH$_2$-pyridine); Method: I-5 | Fast eluted 8A | Slow eluted 8B | 188.10 ([M + 1 − 28]$^+$) |
| 9 | (Cl, NH$_2$-pyridazine); Method: I-6 | Fast eluted 9A | Slow eluted 9B | 191.16 |
| 10 | (Br, NH$_2$-pyrimidine); Method: I-6 | Fast eluted 10A Chiralpak IA column | Slow eluted 10B | 191.07 |
| 11 | (Br, NH$_2$-phenyl); Method: I-6 | Fast eluted 11A | Slow eluted 11B | 189.13 |

TABLE 1-continued

Epoxides prepared using the method described for I-5 or I-6

| Intermediate No. | Column 2 | Structure and name | Structure and name | LC-MS [M + 1]⁺ |
|---|---|---|---|---|
| 12 | Br-phenyl-Me with NH₂ (Method: I-6) | Fast eluted 12A (tetrazolyl-phenyl-Me-epoxide) | Slow eluted 12B (tetrazolyl-phenyl-Me-epoxide) | 203.1 |
| 13 | Br-phenyl-OCH₃ with NH₂ (Method: I-6) | Fast eluted 13A (tetrazolyl-phenyl-OCH₃-epoxide) | Slow eluted 13B (tetrazolyl-phenyl-OCH₃-epoxide) | 219.3 |
| 14 | Br-phenyl-F with NH₂ (Method: I-6) | Fast eluted 14A (tetrazolyl-phenyl-F-epoxide) | Slow eluted 14B (tetrazolyl-phenyl-F-epoxide) | 207.3 |

INTERMEDIATE 15

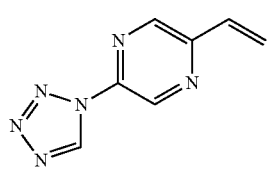

2-(1H-Tetrazol-1-yl)-5-vinylpyrazine

Step A: 2-Bromo-5-(1H-tetrazol-1-yl)pyrazine

To a solution of 5-bromopyrazin-2-amine (10.75 g, 57.5 mmol) in ethyl acetate (150 mL) was added trimethylsilyl 2,2,2-trifluoroacetate (17 mL, 98 mmol). The mixture was stirred for 5 min, and triethoxymethane (17.21 ml, 103 mmol) was added. After the resulting mixture was stirred for another five min, azidotrimethylsilane (12.09 ml, 92 mmol) was added. Stirring continued at rt for 2 days, and the mixture was concentrated under reduced pressure. Recrystallization of the residue from ethyl acetate afforded the title compound. LCMS [M+2+1]⁺=228.9.

Step B: 2-(1H-Tetrazol-1-yl)-5-vinylpyrazine

A solution of 2-bromo-5-(1H-tetrazol-1-yl)pyrazine (11.2 g, 49.3 mmol), potassium vinyltrifluoroborate (13.2 g, 99.0 mmol), 1,1'-bis(diphenylphosphino)ferrocene-palladium(ii) dichloride dichloromethane complex (2.01 g, 2.47 mmol), and TEA (13.8 mL, 99.0 mmol) in ethanol (150 mL) was heated at reflux at 82° C. for 4 h. The reaction mixture was allowed to cool to rt, and the precipitation was filtered off. The filtrate was concentrated, and the residue was purified by flash chromatography (Biotage, Si, ethyl acetate in hexane: 35 to 45%) affording the title compound. The filter cake was stirred in DCM (50 mL), and the solid was filtered off. The filtrate was concentrated to afford more of the title compound. LCMS [M+1]⁺=175.1.

The following arylvinyl intermediates in Table 2 were prepared employing a similar synthetic method as that described for Intermediate 15 using the noted starting material.

TABLE 2

Arylvinyls prepared according to the method described for INTERMEDIATE 15

| Intermediate No. | Starting material | Structure and name | LC-MS [M + 1]⁺ |
|---|---|---|---|
| 16 | Br-pyridazine-NH₂ | 3-(1H-tetrazol-1-yl)-6-vinylpyridazine | 175 |

TABLE 2-continued

Arylvinyls prepared according to the method described for INTERMEDIATE 15

| Intermediate No. | Starting material | Structure and name | LC-MS [M + 1]+ |
|---|---|---|---|
| 17 | 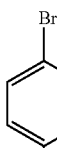 | 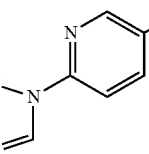<br>2-(1H-tetrazol-1-yl)-5-vinylpyridine | 174 |

INTERMEDIATE 18

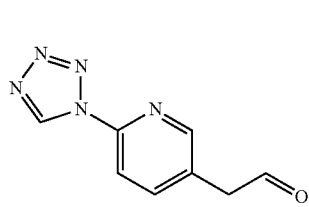

2-(6-(1H-Tetrazol-1-yl)pyridin-3-yl)acetaldehyde

Step A: 2-(6-(1H-Tetrazol-1-yl)pyridin-3-yl)ethanol

To a solution of 5-(oxiran-2-yl)-2-(1H-tetrazol-1-yl)pyridine (500 mg, 2.64 mmol) in ethanol (5.3 mL) were added 10% Pd/C (101 mg, 0.952 mmol) and HCOONH$_4$ (500 mg, 7.93 mmol). The reaction mixture was vigorously stirred for 1.5 h, and filtered through a pad of silica gel. The filtrate was evaporated to give 2-(6-(1H-tetrazol-1-yl)pyridin-3-yl)ethanol. $^1$H NMR (500 MHz, CDCl$_3$) δ 9.54 (s, 1H), 8.43 (d, J=2.0 Hz, 1H), 8.02 (d, J=8.3 Hz, 1H), 7.90 (dd, J=8.3, 2.0 Hz, 1H), 3.91 (t, J=6.3 Hz, 2H), 2.96 (t, J=6.3 Hz, 2H).

Step B: 2-(6-(1H-Tetrazol-1-yl)pyridin-3-yl)acetaldehyde

To a solution of 2-(6-(1H-tetrazol-1-yl)pyridin-3-yl)ethanol (100 mg, 0.523 mmol) in DCM (2.6 mL) was added Dess-Martin periodinane (333 mg, 0.785 mmol). The mixture was stirred for 1.5 h, diluted with 10% Na$_2$S$_2$O$_2$, NaHCO$_3$, and stirred for 20 min. The aqueous layer was extracted with DCM, and the combined organic layers were washed with brine, dried (MgSO$_4$), and concentrated to give the title compound. LC/MS: [(M+1)]$^+$=190

INTERMEDIATE 19

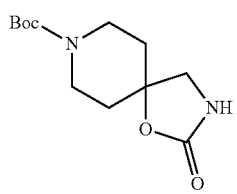

tert-butyl 2-oxo-1-oxa-3,8-diazaspiro[4.5]decane-8-carboxylate

Step A: tert-butyl 4-(2-ethoxy-2-oxoethyl)-4-hydroxypiperidine-1-carboxylate

To a solution of lithium bis(trimethylsilyl)amide (120 mL, 1.0 M solution in THF, 0.12 mol) in THF (120 mL) at −78° C. was added ethyl acetate (13 mL); then, a solution of tert-butyl 4-oxopiperidine-1-carboxylate (20 g, 0.1 mol) in THF (80 mL) was added at −78° C. After the addition, the mixture was warmed up to 0° C. and stirred for another 2 h. The aqueous layer was extracted with ethyl acetate; the organic phase was washed with brine, dried over Na$_2$SO$_4$ and concentrated to afford the crude title compound.

Step B: 2-(1-(tert-butoxycarbonyl)-4-hydroxypiperidin-4-yl)acetic acid

A solution of tert-butyl 4-(2-ethoxy-2-oxoethyl)-4-hydroxypiperidine-1-carboxylate (30.0 g, 0.105 mol) in methanol (130 mL) and 2N NaOH solution (100 mL, 0.2 mol) was stirred at 25° C. for 1.5 h, then the mixture was evaporated and the aqueous layer was extracted with ethyl acetate. The water phase was adjusted to pH 6 with 2N HCl, the aqueous layer was extracted with ethyl acetate, then the organic phase was washed with brine, dried over Na$_2$SO$_4$ and concentrated to afford the crude title compound.

Step C: tert-butyl 2-oxo-1-oxa-3,8-diazaspiro[4.5]decane-8-carboxylate

A mixture of 2-(1-(tert-butoxycarbonyl)-4-hydroxypiperidin-4-yl)acetic acid (22 g, 0.085 mol), DPPA (30 g, 0.11 mol), Et$_3$N (150 mL) in Toluene (400 mL) was stirred at 105° C. under nitrogen for 12 h. The reaction mixture was quenched by the addition of the saturated aqueous NaHCO$_3$, the organic phase was washed with brine, dried over Na$_2$SO$_4$, the mixture was concentrated to remove most of toluene, then ether was added and filtered. The filter cake was washed with ether, the solid was dried under vacuum to afford the pure title compound. $^1$H NMR (300 MHz, CDCl$_3$) δ: 5.35 (brs, 1H), 3.83-3.85 (m, 2H), 3.26-3.35 (m, 4H), 1.93-1.97 (m, 2H), 1.68-1.75 (m, 2H), 1.46 (s, 9H).

INTERMEDIATE 20

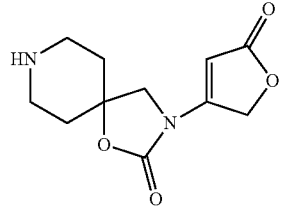

3-(5-oxo-2,5-dihydrofuran-3-yl)-1-oxa-3,8-diazaspiro[4.5]decan-2-one

Step A: tert-butyl 2-oxo-3-(5-oxo-2,5-dihydrofuran-3-yl)-1-oxa-3,8-diazaspiro[4.5]decane-8-carboxylate To a microwave vial was charged tert-butyl 2-oxo-1-oxa-3,8-diazaspiro[4.5]decane-8-carboxylate (100 mg, 0.390 mmol), commercially available 4-bromofuran-2(5H)-one (76 mg, 0.468 mmol), Pd$_2$(dba)$_3$ (18 mg, 0.020 mmol), Xantphos (34 mg, 0.059 mmol), and cesium carbonate (191 mg, 0.585 mmol). The vial was sealed, degassed, and filled with Toluene (1561 µL). The reaction mixture was heated at 90° C. for 4 h. The reaction mixture was diluted with water, extracted with ethyl acetate, washed with brine, dried over MgSO$_4$, evaporated to give the crude product, which was purified by ISCO MPLC eluting with a (0-10% MeOH/DCM) gradient.

Step B: 3-(5-oxo-2,5-dihydrofuran-3-yl)-1-oxa-3,8-diazaspiro[4.5]decan-2-one tert-Butyl 2-oxo-3-(5-oxo-2,5-dihydrofuran-3-yl)-1-oxa-3,8-diazaspiro[4.5]decane-8-carboxylate (80 mg, 0.236 mmol) in DCM (1182 μL) was treated with TFA (546 μl, 7.09 mmol) at 0° C. until the Boc protective group was removed and then concentrated to remove volatiles. Then a 2 g BOND ELUT SCX (ion exchange cartridge) was first rinsed with MeOH, loaded sample with MeOH, washed with MeOH dropwise to remove TFA, finally rinsed with 2N NH$_3$/MeOH to get product as free amine after concentration. (M+H)$^+$ 239

INTERMEDIATE 21

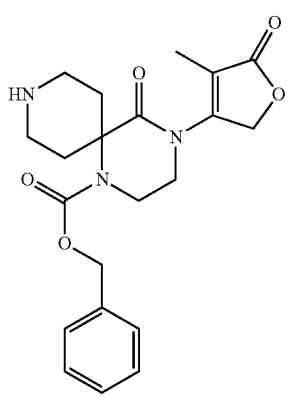

benzyl 4-(4-methyl-5-oxo-2,5-dihydrofuran-3-yl)-5-oxo-1,4,9-triazaspiro[5.5]undecane-1-carboxylate

Step A: 1-benzyl 9-tert-butyl 5-oxo-1,4,9-triazaspiro[5.5]undecane-1,9-dicarboxylate A THF (8.25 mL) solution of commercially available (ChemBridge Building Block Library catalog #4042448; Aldrich catalog # CDS019358) tert-butyl 5-oxo-1,4,9 triazaspiro[5.5]undecane-9-carboxylate (2.00 g, 7.43 mmol) was treated with a solution of potassium carbonate (1.03 g, 7.43 mmol) in H$_2$O (6.7 mL) followed by benzyl chloroformate (1.17 mL, 8.17 mmol). The reaction mixture was allowed to stir at ambient temperature for 2 hours and then concentrated in vacuo (THF removal). The remaining aqueous layer was then extracted with DCM (3×15 mL). The combined organic layers were then dried over sodium sulfate, filtered and concentrated in vacuo. The crude residue was purified via MPLC (0-100% EtOAc/Hex gradient) to afford the title compound. (M+H)$^+$ 404

Step B: 1-benzyl 9-tert-butyl 4-(4-methyl-5-oxo-2,5-dihydrofuran-3-yl)-5-oxo-1,4,9-triazaspiro[5.5]undecane-1,9-dicarboxylate A solution of 1-benzyl 9-tert-butyl 5-oxo-1,4,9-triazaspiro[5.5]undecane-1,9-dicarboxylate (350 mg, 0.867 mmol) in toluene (10 mL) was treated with 4-methyl-5-oxo-2,5-dihydrofuran-3-yl trifluoromethanesulfonate (Int. 4, 214 mg, 0.867 mmol), cesium carbonate (424 mg, 1.30 mmol), Xantphos (75 mg, 0.130 mmol) and Pd$_2$(dba)$_3$ (39.7 mg, 0.043 mmol). The reaction vessel was sealed and the atmosphere was evacuated/purged with N$_2$ (3 cycles). The reaction mixture was then heated at 90° C. for 5 h, cooled to ambient temperature and filtered through a plug of CELITE (rinsing with EtOAc). The filtrate was concentrated in vacuo and the crude residue was purified via MPLC (0-70% EtOAc/Hex gradient) to afford the title compound. (M+H)$^+$ 500

Step C: benzyl 4-(4-methyl-5-oxo-2,5-dihydrofuran-3-yl-5-oxo-1,4,9-triazaspiro[5.5]undecane-1-carboxylate A DCM solution (2 mL) of 1-benzyl 9-tert-butyl 4-(4-methyl-5-oxo-2,5-dihydrofuran-3-yl)-5-oxo-1,4,9-triazaspiro[5.5]undecane-1,9-dicarboxylate (343.6 mg, 0.688 mmol) was treated with TFA (2 mL, 26.0 mmol) and stirred at ambient temperature for 15 h. The reaction mixture was concentrated in vacuo and the crude residue was passed through a Varian BOND ELUT SCX ion-exchange column eluting with MeOH followed by 2M NH$_4$OH/MeOH. The desired band was concentrated in vacuo to afford the title compound. (M+H)$^+$ 400

INTERMEDIATE 22

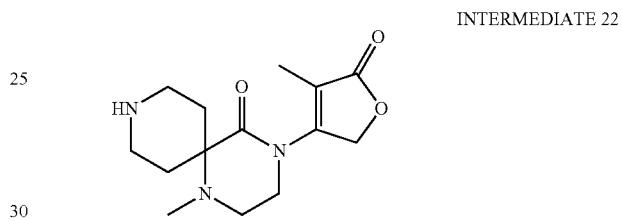

1-methyl-4-(4-methyl-5-oxo-2,5-dihydrofuran-3-yl)-1,4,9-triazaspiro[5.5]undecan-5-one

Step A: 1-benzyl 9-tert-butyl 5-oxo-1,4,9-triazaspiro[5.5]undecane-1,9-dicarboxylate 1-benzyl 9-tert-butyl 5-oxo-1,4,9-triazaspiro[5.5]undecane-1,9-dicarboxylate was prepared in the same manner as benzyl 4-(4-methyl-5-oxo-2,5-dihydrofuran-3-yl)-5-oxo-1,4,9-triazaspiro[5.5]undecane-1-carboxylate (Int. 21, step A). (M+H)$^+$ 404.

Step B: 1-benzyl 9-tert-butyl 4-(4-methyl-5-oxo-2,5-dihydrofuran-3-yl)-5-oxo-1,4,9-triazaspiro[5.5]undecane-1,9-dicarboxylate 1-benzyl 9-tert-butyl 4-(4-methyl-5-oxo-2,5-dihydrofuran-3-yl)-5-oxo-1,4,9-triazaspiro[5.5]undecane-1,9-dicarboxylate was prepared in the same manner as benzyl 4-(4-methyl-5-oxo-2,5-dihydrofuran-3-yl)-5-oxo-1,4,9-triazaspiro[5.5]undecane-1-carboxylate (Int. 21, step B). (M+H)$^+$ 500

Step C: tert-butyl 4-(4-methyl-5-oxo-2,5-dihydrofuran-3-yl)-5-oxo-1,4,9-triazaspiro[5.5]undecane-9-carboxylate A solution of 1-benzyl 9-tert-butyl 4-(4-methyl-5-oxo-2,5-dihydrofuran-3-yl)-5-oxo-1,4,9-triazaspiro[5.5]undecane-1,9-dicarboxylate (410 mg, 0.821 mmol) in DCM (20 mL) was treated with palladium on carbon (103 mg, 0.968 mmol) followed by MeOH (4 mL). The atmosphere in the reaction vessel was evacuated and purged with H$_2$ (3 cycles) and the reaction mixture was stirred under a balloon of H$_2$ over 15 h. The reaction mixture was filtered through a plug of CELITE (rinsing with MeOH and DCM), the filtrate was concentrated under reduced pressure and dried in vacuo affording tert-butyl 4-(4-methyl-5-oxo-2,5-dihydrofuran-3-yl)-5-oxo-1,4,9-triazaspiro[5.5]undecane-9-carboxylate which was used without further purification. (M+H)+ 366

Step D: tert-butyl 1-methyl-4-(4-methyl-5-oxo-2,5-dihydrofuran-3-yl)-5-oxo-1,4,9-triazaspiro[5.5]undecane-9-carboxylate trifluoroacetate A solution of tert-butyl 4-(4-methyl-5-oxo-2,5-dihydrofuran-3-yl)-5-oxo-1,4,9-triazaspiro[5.5]undecane-9-carboxylate (271 mg, 0.742 mmol) in THF (10 mL) was treated with 37% aq. formaldehyde (2.87 mL, 38.6 mmol) and sodium triacetoxyborohydride (472 mg, 2.23 mmol). The reaction mixture stirred for 1 h at ambient temperature when an additional 3.0 eq of sodium triacetoxyborohydride (472 mg, 2.23 mmol) was added and the reaction mixture was stirred for an additional 1 hour. The reaction mixture was treated with saturated aq. NaHCO3 and partitioned with EtOAc. The organic layer was separated, dried (Na2SO4), filtered and concentrated under reduced pressure. The residue was purified by prep. HPLC with gradient elution 10-100% CH3CN/H2O+v 0.1% TFA. The desired fractions were combined, concentrated and lyophilized affording tert-butyl 1-methyl-4-(4-methyl-5-oxo-2,5-dihydrofuran-3-yl)-5-oxo-1,4,9-triazaspiro[5.5]undecane-9-carboxylate trifluoroacetate. (M+H)+=380

Step E: 1-methyl-4-(4-methyl-5-oxo-2,5-dihydrofuran-3-yl)-1,4,9-triazaspiro[5.5]undecan-5-one A solution of tert-butyl 1-methyl-4-(4-methyl-5-oxo-2,5-dihydrofuran-3-yl)-5-oxo-1,4,9-triazaspiro[5.5]undecane-9-carboxylate trifluoroacetate (240 mg, 0.486 mmol) in dioxane (4 mL)/MeOH (2 mL) was treated with a 4M/Dioxane solution of HCl (4 mL, 16.00 mmol). The reaction mixture was stirred at room temperature for approximately 1 hour and then concentrated in vacuo. The crude residue was partitioned between EtOAc and saturated aqueous sodium bicarbonate. The combined organic layers were dried (Na2SO4), filtered, concentrated in vacuo to afford 1-methyl-4-(4-methyl-5-oxo-2,5-dihydrofuran-3-yl)-1,4,9-triazaspiro[5.5]undecan-5-one which was used without further purification. (M+H)+ 280 stirred at rt for 16 h. The reaction mixture was quenched by the addition of the saturated aqueous NH4Cl and evaporated to afford the crude product. The crude product was purified by column chromatography on silica gel eluted with (PE/EA 50:1→30:1→15:1) to give the title compound.

Step B: 1-tert-butyl 4-methyl 4-(2-oxoethoxy)piperidine-1,4-dicarboxylate

To a solution of 1-tert-butyl 4-methyl 4-(allyloxy)piperidine-1,4-dicarboxylate (1.2 g, 4 mmol) in MeOH (30 mL) was added osmium tetroxide (30 uL, 0.006 mmol, 0.81 g/mL H2O) and sodium periodate (16 ml, 16 mmol, 1M). The mixture was allowed to stir at rt for 16 hours. The mixture was quenched with Na2S2O3 (50 mg), extracted with ethyl acetate (20 mL×3), dried over Na2SO4 and concentrated to afford the crude product, which was further purified by column chromatography on silica gel eluted with (PE/EA 20:1→10:1→5:1→1:1) to give the title compound.

Step C: 1-tert-butyl 4-methyl 4-(2-(dibenzylamino)ethoxy)piperidine-1,4-dicarboxylate To a stirred solution of 1-tert-butyl 4-methyl 4-(2-oxoethoxy)piperidine-1,4-dicarboxylate (0.3 g, 1 mmol) in DCE (5 mL) was added dibenzyl amine (0.3 g, 1.5 mmol), the resulted mixture was stirred at room temperature for 1 h. Then sodium triacetoxyborohydride (0.42 g, 2 mmol) was added to the reaction mixture, the reaction mixture was stirred for further 4 h at room temperature. The mixture was quenched with water (5 mL), extracted with DCM (5 mL×3), the combined organic portions were concentrated and purified by column chromatography gel eluted with (PE/EA 5:1→2:1→1:1) to give the title compound.

Step D: tert-butyl 5-oxo-1-oxa-4,9-diazaspiro[5.5]undecane-9-carboxylate

A mixture of 1-tert-butyl 4-methyl 4-(2-(dibenzylamino)ethoxy)piperidine-1,4-dicarboxylate (290 mg, 0.6 mmol) and 10% palladium hydroxide on carbon (20%, w/w, 30 mg) in MeOH (10 mL) was hydrogenated under 40 psi of Hydrogen at 30° C. overnight. Then the mixture was cooled to room temperature and the catalyst was filtered off. The filtrate was concentrated in vacuo to give the title compound.

INTERMEDIATE 23

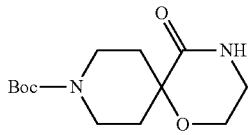

tert-butyl 5-oxo-1-oxa-4,9-diazaspiro[5.5]undecane-9-carboxylate

Step A: 1-tert-butyl 4-methyl 4-(allyloxy)piperidine-1,4-dicarboxylate

NaH (0.92 g, 15.4 mol, 60% dispersion in mineral oil) was added the five portions to a stirred solution of compound 1-tert-butyl 4-methyl 4-hydroxypiperidine-1,4-dicarboxylate (2 g, 7.7 mmol) being cooled to 0° C. in DMF (20 mL). After the mixture was stirred at 0° C., the 3-allyl bromide (1.2 g, 10 mmol) was added, dropwise. The mixture was

INTERMEDIATE 24

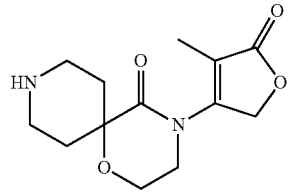

4-(4-methyl-5-oxo-2,5-dihydrofuran-3-yl)-1-oxa-4,9-diazaspiro[5.5]undecan-5-one

Step A: tert-butyl 4-(4-methyl-5-oxo-2,5-dihydrofuran-3-yl)-5-oxo-1-oxa-4,9-diazaspiro[5.5]undecane-9-carboxylate A mixture of tert-butyl 5-oxo-1-oxa-4,9-diazaspiro[5.5]undecane-9-carboxylate (Int. 23, 0.92 g, 3.40 mmol), 4-methyl-5-oxo-2,5-dihydrofuran-3-yl trifluoromethanesulfonate (Int. 4, 1.01 g, 4.08 mmol), Xantphos (0.197 g, 0.340 mmol), PdOAc$_2$ (0.038 g, 0.170 mmol), water (0.184 mL, 10.21 mmol), and K$_2$CO$_3$ (0.941 g, 6.81 mmol) in toluene (30 mL) was flushed with N$_2$ and heated at 65° C. for overnight. After filtration through CELITE followed by washing with DCM, the filtrate was concentrated and the residue was purified on Biotage (MPLC) using 40-100% EtOAc/hexane eluent gradient over 30 min to give the target compound.

Step B: 4-(4-methyl-5-oxo-2,5-dihydrofuran-3-yl)-1-oxa-4,9-diazaspiro[5.5]undecan-5-one To a solution of tert-butyl 4-(4-methyl-5-oxo-2,5-dihydrofuran-3-yl)-5-oxo-1-oxa-4,9-diazaspiro[5.5]undecane-9-carboxylate (1.17 g, 3.19 mmol) in DCM (5 mL) was added TFA (4.92 mL, 63.9 mmol) at rt and the resulting solution was stirred at rt for 1 h. After removing the volatile components, the residue was dissolved in DCM (100 mL), and 1N NaOH (200 mL), the alkaline phase was extracted with DCM three times. The combined DCM phases were dried over Na$_2$SO$_4$ then concentrated to give the target product as free base. LC-MS (ESI, m/z): 267 [M+1]$^+$.

INTERMEDIATE 25

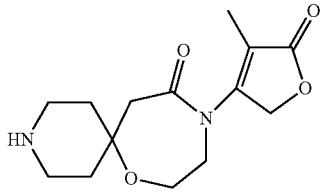

10-(4-methyl-5-oxo-2,5-dihydrofuran-3-yl)-7-oxa-3,10-diazaspiro[5.6]dodecan-11-one Step A: tert-butyl 4-oxo-1-oxa-9-azaspiro[5.5]undec-2-ene-9-carboxylate To the solution of tert-butyl 4-oxopiperidine-1-carboxylate (6.15 g, 30.9 mmol) in 2-butanol (15 ml) was added (E)-3-((tert-butyldimethylsilyl)oxy)-N,N-dimethylbuta-1,3-dien-1-amine (4.0 ml, 15.44 mmol) slowly at rt. The reaction mixture was stirred until diene was fully consumed. The solvent was removed in vacuo and the residue was redissolved in 120 mL diethyl ether. The pale yellow solution was cooled to −78° C. and acetyl chloride (1.318 ml, 18.53 mmol) in 30 mL diethyl ether was added slowly. The mixture was stirred at −78° C. for ca. 10 min and quenched with 150 mL saturated sodium bicarbonate solution. The organic layer was separated, and the aqueous phase was extracted twice with diethyl ether. The combined organic phase was dried over sodium sulfate, filtered and concentrated. The yellow residue was purified by silica gel chromatography using ethyl acetate/hexane to give tert-butyl 4-oxo-1-oxa-9-azaspiro[5.5]undec-2-ene-9-carboxylate, LC/MS: (M+23)$^+$: 290.10.

Step B: tert-butyl 4-oxo-1-oxa-9-azaspiro[5.5]undecane-9-carboxylate

To the solution of tert-butyl 4-oxo-1-oxa-9-azaspiro[5.5]undec-2-ene-9-carboxylate (4.13 g, 15.45 mmol) in methanol (100 ml) was added palladium on carbon (10%, 1.644 g, 1.545 mmol) and the resulting mixture was hydrogenated via hydrogen balloon at rt for 4 h. After filtration under nitrogen, the filtrate was concentrated and the residue was purified on silica gel chromatography using ethyl acetate/hexane to give tert-butyl 4-oxo-1-oxa-9-azaspiro[5.5]undecane-9-carboxylate, LC/MS: (M-56+1): 214.08; (M-100+1): 170.10.

Step C: tert-butyl 11-oxo-7-oxa-3,10-diazaspiro[5.6]dodecane-3-carboxylate

The solution of tert-butyl 4-oxo-1-oxa-9-azaspiro[5.5]undecane-9-carboxylate (1.5 g, 5.57 mmol) and (aminooxy)sulfonic acid (1.890 g, 16.71 mmol) in Acetic Acid (50 ml) was heated at 130° C. for 3 h. After removing the volatile, the residue was dissolved in water (20 mL) and dioxane (20 mL). The solution was treated with sodium hydroxide (27.8 ml, 27.8 mmol) before addition of di-tert-butylcarbonate (1.277 mL, 5.50 mmol) in dioxane (10 mL) dropwise. The resulting solution was stirred at rt overnight before concentration on rotary evaporator. The mixture was extracted with methylene chloride (3×100 mL). The combined organic phase was dried over sodium sulfate, concentrated and the residue was purified by silica gel chromatography using ethyl acetate/hexane to give tert-butyl 11-oxo-7-oxa-3,10-diazaspiro[5.6]dodecane-3-carboxylate. LC/MS: (M+23)$^+$: 307.14.

Step D: tert-butyl 10-(4-methyl-5-oxo-2,5-dihydrofuran-3-yl)-11-oxo-7-oxa-3,10-diazaspiro[5.6]dodecane-3-carboxylate The mixture of tert-butyl 11-oxo-7-oxa-3,10-diazaspiro[5.6]dodecane-3-carboxylate (100 mg, 0.352 mmol), 4-methyl-5-oxo-2,5-dihydrofuran-3-yl trifluoromethanesulfonate (Int. 4, 104 mg, 0.422 mmol), Xanthphos (20.35 mg, 0.035 mmol), palladium acetate (3.95 mg, 0.018 mmol), water (19.01 µL, 1.055 mmol), and potassium carbonate (97 mg, 0.703 mmol) in toluene (5 ml)) was heated at 65° C. overnight. After filtration through CELITE, the filtrate was concentrated and the residue was purified on TLC using ethyl acetate/hexane as developing solvents to give tert-butyl 10-(4-methyl-5-oxo-2,5-dihydrofuran-3-yl)-11-oxo-7-oxa-3,10-diazaspiro[5.6]dodecane-3-carboxylate. LC/MS: (M+1)$^+$: 381.13.

Step E: 10-(4-methyl-5-oxo-2,5-dihydrofuran-3-yl)-7-oxa-3,10-diazaspiro[5.6]dodecan-11-one To the solution of tert-butyl 10-(4-methyl-5-oxo-2,5-dihydrofuran-3-yl)-11-oxo-7-oxa-3,10-diazaspiro[5.6]dodecane-3-carboxylate 63 (41 mg, 0.108 mmol) in methylene chloride (1 ml) was added trifluoroacetic acid (1.661 ml, 21.55 mmol) and the resulting solution was stirred at rt for 1 h before concentration on rotary evaporator. The residue was dissolved in methanol and loaded onto ion exchange column, after washing with methanol, the column was eluted with 2N ammonia in methanol to give 10-(4-methyl-5-oxo-2,5-dihydrofuran-3-yl)-7-oxa-3,10-diazaspiro[5.6]dodecan-11-one. LC/MS: (M+1)$^+$: 281.15.

INTERMEDIATE 26

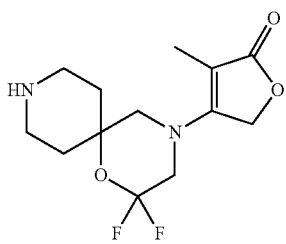

4-(2,2-difluoro-1-oxa-4,9-diazaspiro[5.5]undecan-4-yl)-3-methylfuran-2(5H)-one

Step A: tert-butyl 1-oxa-6-azaspiro[2.5]octane-6-carboxylate

Sodium hydride (7.90 g, 0.33 mol, 60% dispersion in mineral oil) was washed with petroleum ether and then suspended in DMSO (100 mL). A mixture of trimethylsulfoxonium iodide (24.00 g, 0.11 mol) in DMSO (200 mL) was added dropwise to the above solution under $N_2$ during a period of 30 min. After stirred at 40° C. for 20 min, a solution of tert-butyl 4-oxopiperidine-1-carboxylate (20.00 g, 0.10 mol) in DMSO (100 mL) was added slowly. The mixture was stirred at room temperature for 18 h and then poured into ice water (100 mL), extracted with dichloromethane (200 mL×2). The combined organic layer was washed with water (200 mL×3), dried over anhydrous sodium sulfate and filtered. The filtrate was concentrated and re-dissolved in ether, filtered and concentrated, the residue was purified by flash chromatography (0-20% ethyl acetate in petroleum ether) to give the title compound. LC-MS (ESI, m/z): 214 [M+1]$^+$.

Step B: tert-butyl 4-(aminomethyl)-4-hydroxypiperidine-1-carboxylate hydrochloride A solution of tert-butyl 1-oxa-6-azaspiro[2.5]octane-6-carboxylate (10.00 g, 47.0 mol) in ammonia saturated methanol (100 mL) was stirred at room temperature for 8 h. The solvent was removed by evaporation and the residue was diluted with water and acidified with 1 M HCl to pH6 while large amount of solid was precipitated. The resulting residue was filtered and dried to afford the title compound. LC-MS (ESI, m/z): 231 [M+1]$^+$.

Step C: tert-butyl 4-((2-bromo-2,2-difluoroacetamido)methyl)-4-hydroxypiperidine-1-carboxylate To a solution of tert-butyl 4-(aminomethyl)-4-hydroxypiperidine-1-carboxylate hydrochloride (10.00 g, 37.6 mmol) in DMF (80 mL) was added ethyl 2-bromo-2,2-difluoroacetate (8.00 g, 39.5 mmol). The mixture was stirred at room temperature for 16 h. The mixture was diluted with water and extracted with ethyl acetate several time. The combined organic layer was washed with water, brine and dried over anhydrous sodium sulfate, filtered and concentrated, the residue was purified by flash chromatography (0-20% ethyl acetate in petroleum ether) to afford the title compound. LC-MS (ESI, m/z): 387 [M+1]$^+$.

Step D: tert-butyl 2,2-difluoro-3-oxo-1-oxa-4,9-diazaspiro[5.5]undecane-9-carboxylate To a solution of tert-butyl 4-((2-bromo-2,2-difluoroacetamido)methyl)-4-hydroxypiperidine-1-carboxylate (5.00 g, 12.9 mmol) in THF (100 mL) was added a solution of potassium tert-butoxide in THF (1 M in THF, 25 mL, 25 mmol) dropwise over a period of 30 min at room temperature under nitrogen atmosphere. The mixture was heated to 70° C. for 10 min. After cooling to room temperature, water (100 mL) was added, the organic layer was separated and the aqueous layer was extracted with ethyl acetate twice. The combined organic layer was washed with brine, dried over anhydrous sodium sulfate, filtered and concentrated. The residue was purified by flash chromatography (0-25% ethyl acetate in petroleum ether) to give the title compound. LC-MS (ESI, m/z): 307 [M+1]$^+$.

Step E: tert-butyl 2,2-difluoro-1-oxa-4,9-diazaspiro[5.5]undecane-9-carboxylate

To a solution of tert-butyl 2, 2-difluoro-3-oxo-1-oxa-4,9-diazaspiro[5.5]undecane-9-carboxylate (2.00 g, 6.53 mmol) in THF (50 mL) was added borane methyl sulfide complex (1 M in THF, 19.5 mL, 19.5 mmol) dropwise over a period of 10 minutes at room temperature under nitrogen atmosphere. After addition, the mixture was heated to 55° C. for 25 min and then cooled to room temperature. The mixture was quenched by addition of methanol (10 mL). N1,N2-dimethylethane-1, 2-diamine (2.40 g, 27.3 mmol) was then added and the reaction was heated at 70° C. for 40 min. The solvent was removed under reduced pressure and the residue was purified by flash chromatography (0-20% ethyl acetate in petroleum ether) to give the title compound. LC-MS (ESI, m/z): 293 [M+1]$^+$.

Step F: tert-butyl 2,2-difluoro-4-(4-methyl-5-oxo-2,5-dihydrofuran-3-yl)-1-oxa-4,9-diazaspiro[5.5]undecane-9-carboxylate To a solution of tert-butyl 2, 2-difluoro-1-oxa-4, 9-diazaspiro[5.5]undecane-9-carboxylate (160 mg, 0.55 mmol) and N, N-diisopropylethylamine (200 μL, 1.1 mmol) in toluene (10 mL) was added 4-methyl-5-oxo-2,5-dihydrofuran-3-yl trifluoromethanesulfonate (Int. 4, 130 mg, 0.55 mmol). The reaction mixture was heated to 100° C. and stirred for 2 h. The solvent was removed by evaporation and the residue was purified by flash chromatography (0-50% ethyl acetate in petroleum ether) to give the title compound. LC-MS (ESI, m/z): 389 [M+1]$^+$.

Step G: 4-(2,2-difluoro-1-oxa-4,9-diazaspiro[5.5]undecan-4-yl)-3-methylfuran-2(5H)-one tert-butyl 2,2-difluoro-4-(4-methyl-5-oxo-2,5-dihydrofuran-3-yl)-1-oxa-4,9-diazaspiro[5.5]undecane-9-carboxylate was dissolved in DCM and treated with TFA until the Boc group had been removed. The volatiles were removed to provide the title compound. LC-MS (ESI, m/z): 289 [M+1]$^+$.

INTERMEDIATE 27

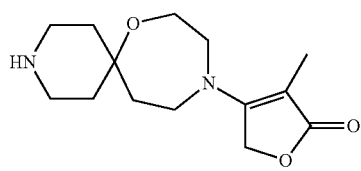

3-methyl-4-(7-oxa-3,10-diazaspiro[5.6]dodecan-10-yl)furan-2(5H)-one

Step A: tert-butyl 4-(2-(2-chloroacetamido)ethyl)-4-hydroxypiperidine-1-carboxylate To the solution of tert-butyl 4-(2-aminoethyl)-4-hydroxypiperidine-1-carboxylate (250 mg, 1.023 mmol) and potassium carbonate (424 mg, 3.07 mmol) in ethyl acetate (10 ml) and water (10.00 ml) was added chloroacetic acid (0.109 ml, 1.637 mmol) dropwise at 0° C. while vigorously stirring. The mixture was then stirred at 0° C. for 45 min before extracted with ethyl acetate (3×50 mL). The combined organic phase dried over sodium sulfate, concentrated and the residue was purified on silica gel using ethyl acetate/hexane to give tert-butyl 4-(2-(2-chloroacetamido) ethyl)-4-hydroxypiperidine-1-carboxylate. LC/MS: (M+23)⁺: 343.10 (100%); 344.97 (30%).

Step B: tert-butyl 9-oxo-7-oxa-3,10-diazaspiro[5.6] dodecane-3-carboxylate

To the reflux solution of potassium tert-butoxide (3.68 ml, 3.68 mmol) in tetrahydrofuran (70 mL) was added tert-butyl 4-(2-(2-chloroacetamido)ethyl)-4-hydroxypiperidine-1-carboxylate (358 mg, 1.116 mmol) in tetrahydrofuran (20 mL) over 6 h. At the end of addition the mixture was heated at reflux for a further 15 min and then cooled to rt. The mixture was partitioned between ethyl acetate and brine. The organic layer was dried over sodium sulfate, concentrated to give tert-butyl 9-oxo-7-oxa-3,10-diazaspiro[5.6]dodecane-3-carboxylate. LC/MS: (M+23)⁺: 307.14

Step C: tert-butyl 7-oxa-3,10-diazaspiro[5.6]dodecane-3-carboxylate

To the solution of tert-butyl 9-oxo-7-oxa-3,10-diazaspiro[5.6]dodecane-3-carboxylate (0.221 g, 0.777 mmol) in tetrahydrofuran (20 mL) was added borane-methyl sulfide complex (1.554 ml, 3.11 mmol) at rt and the resulting solution was stirred at rt for 5 h, then heated at 70° C. for 0.5 h. After cooling to rt, the reaction was quenched by methanol. After concentration the residue was treated with methanol (30 mL) and the resulting solution was heated at reflux for 5 h. After removing the volatile the residue was dissolved in methylene chloride (50 mL) and dried over sodium sulfate, concentrated to give tert-butyl 7-oxa-3,10-diazaspiro[5.6]dodecane-3-carboxylate. LC/MS: (M+1)⁺: 271.12.

Step D: tert-butyl 10-(4-methyl-5-oxo-2,5-dihydrofuran-3-yl)-7-oxa-3,10-diazaspiro[5.6]dodecane-3-carboxylate To the solution of tert-butyl 7-oxa-3,10-diazaspiro[5.6]dodecane-3-carboxylate (210 mg, 0.777 mmol) and 4-methyl-5-oxo-2,5-dihydrofuran-3-yl trifluoromethanesulfonate (Int. 4, 191 mg, 0.777 mmol) in tetrahydrofuran (6 mL) was added diisopropylethylamine (0.271 mL, 1.554 mmol) and the resulting solution was heated at 76° C. overnight. After concentration the residue was purified on TLC using ethyl acetate as developing solvent to give tert-butyl 10-(4-methyl-5-oxo-2,5-dihydrofuran-3-yl)-7-oxa-3,10-diazaspiro[5.6]dodecane-3-carboxylate, LC/MS: (M+23)⁺: 389.11.

Step E: 3-methyl-4-(7-oxa-3,10-diazaspiro[5.6]dodecan-10-yl)furan-2(5H)-one

To the solution of tert-butyl 10-(4-methyl-5-oxo-2,5-dihydrofuran-3-yl)-7-oxa-3,10-diazaspiro[5.6]dodecane-3-carboxylate (108 mg, 0.295 mmol) in methylene chloride (2 mL) was added trifluoroacetic acid (2.044 mL, 26.5 mmol) at rt for 2 h. After removing the volatile, the residue was basified on ion exchange column to give 3-methyl-4-(7-oxa-3,10-diazaspiro[5.6]dodecan-10-yl)furan-2(5H)-one. LC/MS: (M+1)⁺: 267.13.

INTERMEDIATE 28

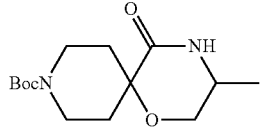

tert-butyl 3-methyl-5-oxo-1-oxa-4,9-diazaspiro[5.5] undecane-9-carboxylate

Step A: methyl 1-benzyl-4-hydroxypiperidine-4-carboxylate

The compound 1-benzyl-4-hydroxypiperidine-4-carbonitrile (21.6 g, 0.10 mol) was added to a mixture of conc.HCl and MeOH (1:1, 300 mL), the resulting mixture was heated at 90° C. for 16 h. The mixture was cooled, adjusted to pH 9 with solid Na₂CO₃, extracted with ethyl acetate (100 mL*3). The combined organic layer was concentrated to afford the title compound.

Step B: 1-tert-butyl 4-methyl 4-hydroxypiperidine-1,4-dicarboxylate

A mixture of compound methyl 1-benzyl-4-hydroxypiperidine-4-carboxylate (20.00 g, 80 mmol), Boc₂O (11.26 g, 88 mmol) and Pd/C (1.0 g, 10%/w) in methanol (200 mL) was stirred under 30 Psi at 30° C. for 18 h. The mixture was filtered through a CELITE pad, and the filtrate was concentrated to give the title compound.

Step C: 1-tert-butyl 4-methyl 4-((2-methylallyl)oxy) piperidine-1,4-dicarboxylate NaH (4.00 g, 0.10 mol, 60% dispersion in mineral oil) was added in portions to a stirred solution of compound 1-tert-butyl 4-methyl 4-hydroxypiperidine-1,4-dicarboxylate (15.0 g, 50 mmol) in DMF (150 mL) cooled at 0° C. After the mixture was stirred at 0° C. for 30 min, 3-bromo-2-methylpropene (10.10 g, 75 mmol) was added dropwise. The mixture was stirred at r.t. for 16 h. The reaction mixture was quenched by the addition of the saturated aqueous NH₄Cl and evaporated, the crude product was purified by column chromatography on silica gel eluted with PE/EtOAc from 50:1 to 15:1 to give the title compound.

Step D: 1-tert-butyl 4-methyl 4-(2-oxopropoxy)piperidine-1,4-dicarboxylate

To a solution of 1-tert-butyl 4-methyl 4-((2-methylallyl) oxy)piperidine-1,4-dicarboxylate (8.00 g, 25.5 mmol) in MeOH (300 mL) was added osmium tetroxide (0.010 ml, 0.026 mmol, 0.81 g/ml in H₂O) and sodium periodate (101 ml, 101 mmol, 1.0 M). The mixture was stirred at r.t. for 16 hours. The mixture was quenched with Na₂S₂O₃ (0.10 g), extracted with ethyl acetate (100 mL*3), dried over Na₂SO₄, filtered and concentrated, the residue was purified by column chromatography on silica gel eluted with PE/EtOAc from 20:1 to 1:1 to give the title compound.

Step E: 3-methyl-5-oxo-1-oxa-4,9-diaza-spiro[5.5]undecane-9-carboxylic acid tert-butyl ester To a solution of 1-tert-butyl 4-methyl 4-(2-oxopropoxy)piperidine-1,4-dicarboxylate (5.00 g, 15.8 mmol) in MeOH (30 mL) was added MgSO$_4$ (3.80 g, 31.6 mmol), NH$_4$OAc (2.43 g, 31.6 mmol) and NaBH$_3$CN (2.00 g, 31.6 mmol). The mixture was heated at 80° C. overnight. The mixture was concentrated, and poured into H$_2$O (40 mL), extracted with EtOAc (15 mL*4), dried over Na$_2$SO$_4$, filtered and concentrated, the residue was purified by column chromatography on silica gel eluted with PE/EtOAc from 5:1 to 1:1 to give the title compound. $^1$H-NMR (400 MHz, MeOD) δ ppm 3.87-3.95 (m, 3H), 3.63 (s, 1H), 3.50 (m, 1H), 3.08 (brs, 2H), 1.75-1.99 (m, 4H), 1.48 (s, 9H), 1.20 (m, 3H). LC-MS (ESI, m/z): 285 [M+1]$^+$.

INTERMEDIATE 29A and 29B

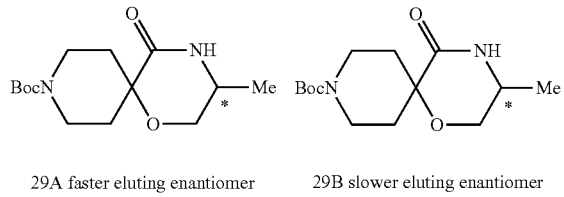

29A faster eluting enantiomer    29B slower eluting enantiomer (S)-tert-butyl 3-methyl-5-oxo-1-oxa-4,9-diazaspiro[5.5]undecane-9-carboxylate AND (R)-tert-butyl 3-methyl-5-oxo-1-oxa-4,9-diazaspiro[5.5]undecane-9-carboxylate tert-butyl 3-methyl-5-oxo-1-oxa-4,9-diazaspiro[5.5]undecane-9-carboxylate was separated to two pure enantiomers by chiral SFC [eluting with 40% MeOH (0.05% DEA)/CO$_2$ on CHIRALCEL OD column]. The absolute stereochemistry of the faster and slower eluting isomers was not unambiguously determined; however, both isomers were useful for making potent ROMK inhibitors.

INTERMEDIATE 30

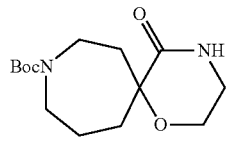

tert-butyl 5-oxo-1-oxa-4,9-diazaspiro[5.6]dodecane-9-carboxylate

Step A: 1-benzylazepan-4-one

To a solution of tert-butyl 4-oxoazepane-1-carboxylate (21.30 g, 0.10 mol) in DCM (20 mL) was added dropwise 20 mL of trifluoroacetic acid at room temperature, and then stirred for 5 h. The solution was concentrated and dissolved in 30 mL of DMF, K$_2$CO$_3$ (34.50 g, 0.25 mol) was added, followed by addition of benzyl bromide (18.80 g, 0.11 mol). The resulting mixture was stirred at 50° C. for 5 h. The mixture was cooled, the inorganic salt was filtered and the solvent was evaporated under reduced pressure. The crude product was purified by column chromatography on silica gel eluted with PE/EA from 50:1 to 15:1 to give the title compound.

Step B: 1-benzyl-4-hydroxyazepane-4-carbonitrile

To a mixture of tetrabutylammonium cyanide (1.34 g, 5.0 mmol) and trimethylsilyl cyanide (6.00 g, 60 mmol) in 100 mL of DCM was added 1-benzylazepan-4-one (10.00 g, 50 mmol) at 0-5° C. Then the mixture was stirred for 2 h, and the product was purified by column chromatography on silica gel eluted with PE/EA from 100:1 to 30:1 to give the title compound.

Step C: methyl 1-benzyl-4-hydroxyazepane-4-carboxylate

The compound 1-benzyl-4-((trimethylsilyl)oxy)azepane-4-carbonitrile (9.06 g, 30 mmol) was added to a solution of conc.HCl/MeOH (1:1, 10 mL), and the mixture was heated at 90° C. for 16 h. The resulting mixture was cooled, adjusted to pH 9 with solid Na$_2$CO$_3$, removed the excess MeOH, extracted with ethyl acetate (10 mL*3). The combined organic layer was concentrated to afford the title compound.

Step D: 1-tert-butyl 4-methyl 4-hydroxyazepane-1,4-dicarboxylate

A mixture of compound methyl 1-benzyl-4-hydroxyazepane-4-carboxylate (5.26 g, 20 mmol), Boc$_2$O (2.82 g, 22 mmol) and Pd/C (0.25 g, 10%/w) in methanol (50 mL) was stirred under 30 Psi of H$_2$ at 30° C. for 18 h. The mixture was filtered through a CELITE pad, and the filtrate was concentrated to give the title compound.

Step D: 1-tert-butyl 4-methyl 4-(allyloxy)azepane-1,4-dicarboxylate

NaH (0.92 g, 15.4 mol, 60% dispersion in mineral oil) was added in five portions to a stirred solution of compound 1-tert-butyl 4-methyl 4-hydroxyazepane-1,4-dicarboxylate (2.10 g, 7.7 mmol) at 0° C. in DMF (20 mL). After the mixture was stirred at 0° C. for 30 min, 3-bromo-propene (1.20 g, 10 mmol) was added dropwise. The mixture was stirred at r.t. for 16 h. The reaction mixture was quenched by the addition of the saturated aqueous NH$_4$Cl and evaporated, the crude product was purified by column chromatography on silica gel eluted with PE/EtOAc from 50:1 to 15:1 to give the title compound.

Step E: 1-tert-butyl 4-methyl 4-(2-oxoethoxy)azepane-1,4-dicarboxylate

To a solution of 1-tert-butyl 4-methyl 4-(allyloxy)azepane-1,4-dicarboxylate (1.21 g, 4 mmol) in MeOH (30 mL) was added osmium tetroxide (30 uL, 0.006 mmol, 0.81 g/mL in water) and sodium periodate (16 mL, 16 mmol, 1 M). The mixture was stirred at r.t. for 16 hours. The mixture was quenched with Na$_2$S$_2$O$_3$ (50 mg), extracted with ethyl acetate (20 mL*3), dried over Na$_2$SO$_4$ and concentrated, the crude product was purified by column chromatography on silica gel eluted with PE/EtOAc from 20:1 to 1:1 to give the title compound.

Step F: 1-tert-butyl 4-methyl 4-(2-(dibenzylamino)ethoxy)azepane-1,4-dicarboxylate To a stirred solution of 1-tert-butyl 4-methyl 4-(2-oxoethoxy)azepane-1,4-dicarboxylate (315 mg, 1.0 mmol) in DCE (5 mL) was added dibenzyl amine (300 mg, 1.5 mmol), the resulted mixture was stirred at room temperature for 1 h. Then sodium triacetoxyborohydride (420 mg, 2 mmol) was added, the reaction mixture was stirred at room temperature for further 4 h. The mixture was quenched with water (5 mL), extracted with DCM (5 mL*3), the combined organic portions were concentrated and purified by column chromatography gel eluted with PE/EAtOc from 5:1 to 1:1 to give the title compound.

Step G: tert-butyl 5-oxo-1-oxa-4,9-diazaspiro[5.6]dodecane-9-carboxylate

A mixture of 1-tert-butyl 4-methyl 4-(2-(dibenzylamino)ethoxy)azepane-1,4-dicarboxylate (300 mg, 0.6 mmol) and 10% palladium hydroxide on carbon (20%, w/w, 30 mg) in MeOH (10 mL) was hydrogenated under 40 Psi of Hydrogen at 30° C. overnight. Then the mixture was cooled to room temperature and the catalyst was filtered off. The filtrate was concentrated to give the title compound. LC-MS (ESI, m/z): 285 [M+1]$^+$.

INTERMEDIATE 31

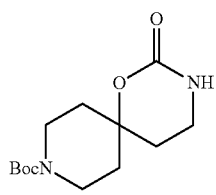

tert-butyl 2-oxo-1-oxa-3,9-diazaspiro[5.5]undecane-9-carboxylate

Step A: tert-Butyl 4-(cyanomethyl)-4-hydroxypiperidine-1-carboxylate

To acetonitrile (0.786 mL, 15.06 mmol) in anhydrous THF (50 mL) was added LDA (6.02 mL, 12.05 mmol) at −78° C. The mixture was stirred for 10 min, then to this mixture was added a solution of tert-butyl 4-oxopiperidine-1-carboxylate (2 g, 10.04 mmol) in THF (10 mL) via syringe. The mixture was stirred at −78° C. for 1 h and TLC indicated that the reaction was completed. Water (300 mL) was added and the mixture was extracted with ethyl acetate (2×300 mL). The combined organic layers were washed with brine (1×300 mL), dried (sodium sulfate), filtered and the solvent was evaporated under reduced pressure to give crude product. The crude product was purified by ISCO (80 g silica gel column, 0-100% EtOAc/Hexane gradient). Removing the solvents gave tert-butyl 4-(cyanomethyl)-4-hydroxypiperidine-1-carboxylate.

Step B: tert-Butyl 4-(2-aminoethyl)-4-hydroxypiperidine-1-carboxylate tert-Butyl 4-(cyanomethyl)-4-hydroxypiperidine-1-carboxylate (1.6 g, 6.66 mmol) was dissolved in MeOH (100 mL) and was treated with H$_2$ (45 psi) on Parr shaker overnight in the presence of Raney Nickel (6.41 µl, 0.666 mmol). Then the catalyst was filtered out on CELITE pad and the filtering cake was washed with a small amount of MeOH. Removal of MeOH gave the crude tert-butyl 4-(2-aminoethyl)-4-hydroxypiperidine-1-carboxylate. LC-MS 267 (M+23).

Step C: tert-Butyl 2-oxo-1-oxa-3,9-diazaspiro[5.5]undecane-9-carboxylate

To the solution of tert-butyl 4-(2-aminoethyl)-4-hydroxypiperidine-1-carboxylate (1.18 g, 4.83 mmol) in THF (40 mL) was added CDI (1.566 g, 9.66 mmol). The mixture was stirred at rt for 72 hours. The reaction was concentrated in vacuo and the residue partitioned between 0.5 M HCl and EtOAc. The aqueous phase was extracted two times with EtOAc and combined extracts washed sequentially with 0.5M HCl, saturated NaHCO$_3$, water and brine, dried (Na$_2$SO$_4$), filtered and concentrated. Then it was loaded on ISCO 40 g silica gel column, and eluted with 0-10% MeOH/DCM gradient. Removing solvents gave tert-butyl 2-oxo-1-oxa-3,9-diazaspiro[5.5]undecane-9-carboxylate. LC-MS 293 (M+23)

INTERMEDIATE 32

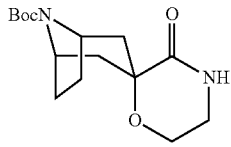 [SMILES: CC(C)(C)OC(=O)N1C2CCC1CC1(C2)OCCNC1=O]

(1R,2'r,5S)-tert-butyl 3'-oxo-8-azaspiro[bicyclo[3.2.1]octane-3,2'-morpholine]-8-carboxylate Step A: (1R,3r,5S)-tert-butyl 3-hydroxy-3-vinyl-8-azabicyclo[3.2.1]octane-8-carboxylate To a solution of (1R,5S)-tert-butyl 3-oxo-8-azabicyclo[3.2.1]octane-8-carboxylate (5 g, 22.19 mmol) in Et$_2$O (150 ml) was added vinylmagnesium bromide (47.6 ml, 33.3 mmol) at rt. The suspension was stirred overnight at rt, quenched with saturated NH$_4$Cl aqueous. The organic layer was separated and the aqueous was extracted with ether. The combined ether layers were dried (MgSO$_4$) and solvent was removed. The residue was purified by column chromotography (120 g silical gel, hexane: EtOAc gradient 0-60% then 60% to give an oil. LC-MS: 276.14 [M+23]$^+$, and 198.14 [M+1-56]$^+$.

Step B: (1R,3r,5S)-tert-butyl 3-(2-(dibenzylamino)ethoxy)-3-vinyl-8-azabicyclo[3.2.1]octane-8-carboxylate To a solution of (1R,3r,5S)-tert-butyl 3-hydroxy-3-vinyl-8-azabicyclo[3.2.1]octane-8-carboxylate (5 g, 19.74 mmol) in THF (100 ml) were added N,N-dibenzyl-2-chloroethanamine (7.69 g, 29.6 mmol) and solid sodium hydride (2.368 g, 59.2 mmol) at rt. The mixture was stirred at rt for 15 min., and tetrabutylammonium iodide (0.729 g, 1.974 mmol) was added. The resultant mixture was stirred at rt for 30 min., heated at 80° C. for 48 hr, cooled to rt, and diluted with water (100 ml) and ether (100 ml). The organic layer was separated, washed with brine, dried over MgSO$_4$ and concentrated. The oily crude compound was purified by column (120 g silica gel, 0-20% ethyl acetate in hexane). LCMS: 477.27 [M+1]$^+$.

Step C: (1R,3r,5S)-tert-butyl 3-(2-(dibenzylamino)ethoxy)-3-formyl-8-azabicyclo[3.2.1]octane-8-carboxylate To a solution of (1R,3r,5S)-tert-butyl 3-(2-(dibenzylamino)ethoxy)-3-vinyl-8-azabicyclo[3.2.1]octane-8-carboxylate (0.5 g, 1.049 mmol) in AcOH (30.00 ml) and Water (8 ml)) were added sodium periodate (0.897 g, 4.20 mmol) and osmium tetraoxide (0.013 g, 0.052 mmol). The suspension was stirred for 24 hr at rt, and concentrated. The residue was dissolved in water (50 ml) and EtOAc (50 ml). The organic layer was separated, and the aqueous was extracted with EtOAc (50 ml). The combined organic layers were washed with brine, dried over $MgSO_4$, and concentrated. The residue was purified by column (0-30% EtOAc in hexane) LCMS: 479.29 $[M+1]^+$.

Step D: (1R,3r,5S)-8-(tert-butoxycarbonyl)-3-(2-(dibenzylamino)ethoxy)-8-azabicyclo[3.2.1]-octane-3-carboxylic acid To a solution of (1R,3r,5S)-tert-butyl 3-(2-(dibenzylamino)ethoxy)-3-formyl-8-azabicyclo[3.2.1]octane-8-carboxylate (0.35 g, 0.731 mmol) in t-BuOH/$H_2O$ (2:1) were added sodium phosphate, monobasic, monohydrate (0.303 g, 2.194 mmol) and 2-methyl-2-butene (2 ml, 0.731 mmol) at rt. The mixture was cooled to 0° C., and sodium chlorite (0.198 g, 2.194 mmol) was added portionwise. The resultant mixture was stirred at rt for 1 hr, acidified with 1N HCl, and extracted with DCM-2-propanol (3:1). The combined organic layers were dried over $Na_2SO_4$ and concentrated. LCMS: 495.27 $[M+1]^+$ to give the title compound which was directly used in the next step.

Step E: (1R,2'r,5S)-tert-butyl 3'-oxo-8-azaspiro[bicyclo[3.2.1]octane-3,2'-morpholine]-8-carboxylate A mixture of (1R,3r,5S)-8-(tert-butoxycarbonyl)-3-(2-(dibenzylamino)ethoxy)-8-azabicyclo[3.2.1]octane-3-carboxylic acid (0.33 g, 0.667 mmol), ammonium formate (0.421 g, 6.67 mmol) and palladium on carbon (0.071 g, 0.067 mmol) in EtOH (30 ml) was heated at 80° C. for 0.5 hr, cooled to rt, and filtered through a filter CELITE pad. The filtrate was concentrated. The residue was heated at 90° C. overnight in benzene with a Dean-Stark to remove generated water. LCMS: 297.15 $[M+1]^+$. The benzene was removed, and the residue was dissolved in DCM. The organic layer was washed with brine, dried (MgSO4) and concentrated. The residue was purified by preparative TLC (10% methanol in DCM) to give the title compound.

TABLE 3: amines prepared in an analogous fashion to the method described for Intermediates 4-(4-methyl-5-oxo-2,5-dihydrofuran-3-yl)-1-oxa-4,9-diazaspiro[5.5]undecan-5-one (Int. 24) or 3-(5-oxo-2,5-dihydrofuran-3-yl)-1-oxa-3,8-diazaspiro[4.5]decan-2-one (20), starting either from commercially available 4-bromofuran-2(5H)-one or from 4-methyl-5-oxo-2,5-dihydrofuran-3-yl trifluoromethanesulfonate (Intermediate 4) and the listed amines which were prepared as described above or were commercially available.

TABLE 3

| Int. No. | Starting material | Product Intermediate | LC-MS $[M + 1]^+$ |
|---|---|---|---|
| 33 | BocN-piperidine-spiro-morpholinone | HN-piperidine-spiro-morpholinone-furanone | 253 |
| 34A | BocN-piperidine-spiro-morpholinone-Me (5A faster eluting enantiomer) | HN-piperidine-spiro-morpholinone-furanone-Me (from faster eluting enantiomer 5A) | 267 |
| 34B | BocN-piperidine-spiro-morpholinone-Me (5B slower eluting enantiomer) | HN-piperidine-spiro-morpholinone-furanone-Me (from slower eluting enantiomer 5B) | 267 |

TABLE 3-continued

| Int. No. | Starting material | Product Intermediate | LC-MS [M + 1]+ |
|---|---|---|---|
| 35A | 5A faster eluting enantiomer | from faster eluting enantiomer 5A | 281 |
| 35B | 5B slower eluting enantiomer | from slower eluting enantiomer 5B | 281 |
| 36 | | | 281 |
| 37 | | | 279 |
| 38 | | | 293 |
| 39 | | | 253 |

INTERMEDIATE 40

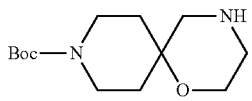

tert-Butyl 1-oxa-4,9-diazaspiro[5.5]undecane-9-carboxylate

Step A: tert-Butyl 4-oxopiperidine-1-carboxylate

To a solution of piperidin-4-one (1.0 mol, 100.0 g) and NaHCO$_3$ (1.6 mmol, 100 g) in H$_2$O (1000 mL) was added (BOC)$_2$O (1.2 mol, 191.6 g). The reaction was stirred at 50° C. overnight. The residue was extracted with EtOAc (3×400 mL) and the combined organic layers were washed with brine, dried over Na$_2$SO$_4$, filtered and concentrated to give tert-butyl 4-oxopiperidine-1-carboxylate. $^1$H NMR (300 MHz, CDCl$_3$) δ: 1.49 (s, 9H), 2.43 (t, J=6.0 Hz, J$_2$=6.0 Hz, 4H), 3.71 (t, J, =6.0 Hz, J$_2$=6.0 Hz, 4H).

Step B: tert-Butyl 4-hydroxy-4-(nitromethyl)piperidine-1-carboxylate

To a mixture of tert-butyl 4-oxopiperidine-1-carboxylate (0.1 mol) and nitro-methane (0.1 mol) in methanol (200 mL) was added sodium methanolate (0.11 mol) at rt and the reaction was stirred for 1 h at room temperature. The solvent was evaporated. The residue was taken up into water, neutralized with acetic acid, extracted twice with EtOAc. The separated organic layer was washed with water, dried, filtered and evaporated to get tert-butyl 4-hydroxy-4-(nitromethyl)piperidine-1-carboxylate. $^1$H NMR (300 MHz, CDCl$_3$) δ: 1.46 (s, 9H), 1.61 (t, J=5.4 Hz, J$_2$=5.4 Hz, 4H), 2.92 (s, 1H), 3.19 (t, J=12.0 Hz, J$_2$=12.0 Hz, 2H), 3.94 (t, J$_1$=6.9 Hz, J$_2$=6.9 Hz, 2H), 4.43 (s, 2H).

Step C: tert-Butyl 4-(aminomethyl)-4-hydroxypiperidine-1-carboxylate

The mixture of tert-butyl 4-hydroxy-4-(nitromethyl)piperidine-1-carboxylate (15.0 g, 0.058 mol) and acetic acid (12 mL) in methanol (180 mL) was hydrogenated at rt with palladium-on-carbon (10%, 1.5 g) as a catalyst. After uptake of hydrogen, the catalyst was filtered off, and the filtrate was evaporated. The residue was taken up into ice water, alkalized with potassium hydroxide, extracted twice with EtOAc, dried over Na$_2$SO$_4$, filtered and concentrated to give tert-butyl 4-(aminomethyl)-4-hydroxypiperidine-1-carboxylate.

Step D: tert-Butyl 4-((2-chloroacetamido)methyl)-4-hydroxypiperidine-1-carboxylate The mixture of tert-butyl 4-(aminomethyl)-4-hydroxypiperidine-1-carboxylate (10.0 g, 45 mmol), chloroacetyl chloride (6 mL, 64 mmol) and K$_2$CO$_3$ (14.0 g, 95 mmol) in EtOAc/H$_2$O (100 mL/100 mL) was stirred for 1 h at 0° C. The crude mixture was extracted with EtOAc (2×300 mL). The combined organics were dried over Na$_2$SO$_4$, filtered and concentrated in vacuo to give tert-butyl 4-((2-chloroacetamido)methyl)-4-hydroxypiperidine-1-carboxylate. $^1$H NMR (300 MHz, CDCl$_3$) δ: 1.45 (s, 9H), 1.53 (d, 4H), 2.59 (s, 1H), 3.21 (s, 2H), 3.35 (s, 2H), 3.78 (d, J=18.0 Hz, 2H), 4.13 (s, 2H), 6.99 (s, 1H).

Step E: tert-Butyl 3-oxo-1-oxa-4,9-diazaspiro[5.5]undecane-9-carboxylate

To a mixture of potassium tert-butoxide (31.8 g, 283 mmol) and tert-butanol (500 mL) was added tert-butyl 4-((2-chloroacetamido)methyl)-4-hydroxypiperidine-1-carboxylate (41.9 g, 141 mmol) in THF (300 mL) over 40 minutes and the resulting mixture was continued to stir for 1 h at room temperature before it was concentrated. The residue was diluted with EtOAc and water, the organic layer was separated, washed with brine, and concentrated to provide tert-butyl 3-oxo-1-oxa-4,9-diazaspiro[5.5]undecane-9-carboxylate. $^1$H NMR (300 MHz, CDCl$_3$) δ: 1.41 (s, 9H), 1.52 (s, 2H), 1.90 (d, J=12.0 Hz, 2H), 2.59 (s, 1H), 3.12 (m, 2H), 3.25 (s, 2H), 3.84 (d, J=6.4 Hz, 2H), 4.17 (s, 2H), 6.12 (s, 1H)

Step F: tert-Butyl 1-oxa-4,9-diazaspiro[5.5]undecane-9-carboxylate

To a solution of tert-butyl 3-oxo-1-oxa-4,9-diazaspiro[5.5]undecane-9-carboxylate (16.0 g, 60 mmol) in THF (70 mL) was added tetrahydrofuran-borane (250 mL, 250 mmol) at room temperature. The reaction mixture was refluxed for 2 h and the solvent was removed under the reduced pressure. To the resulting mixture was added MeOH and N$_1$,N$_1$,N$_2$,N$_2$-tetramethylethane-1,2-diamine and the reaction was stirred at 78° C. overnight. The reaction was concentrated and the residue was diluted with EtOAc and water. The organic layer was separated, washed with brine, and concentrated in vacuo to give tert-butyl 1-oxa-4,9-diazaspiro[5.5]undecane-9-carboxylate. $^1$H NMR (300 MHz, CDCl$_3$) δ: 1.45 (s, 9H), 1.61 (s, 2H), 1.93 (d, J=12.0 Hz, 2H), 2.67 (s, 2H), 2.83 (m, 2H), 3.16 (t, J$_1$=9.0 Hz, J$_2$=12.0 Hz, 2H), 3.65 (m, 4H).

INTERMEDIATE 41

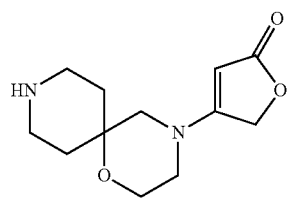

4-(1-oxa-4,9-diazaspiro[5.5]undecan-4-yl)furan-2(5H)-one

Step A: tert-butyl 4-(5-oxo-2,5-dihydrofuran-3-yl)-1-oxa-4,9-diazaspiro[5.5]undecane-9-carboxylate tert-Butyl 1-oxa-4,9-diazaspiro[5.5]undecane-9-carboxylate (500 mg, 1.951 mmol) and commercially available 4-bromofuran-2(5H)-one (318 mg, 1.95 mmol) were mixed in THF (10 mL). DIEA (0.852 mL, 4.88 mmol) was added. The reaction was stirred at 80° C. for 1 hour. Then the solvent was removed under reduced pressure and residue was dissolved in 50 mL of EtOAc and was washed with 30 mL of H$_2$O, 20 mL of brine, dried over Na$_2$SO$_4$. Concentration gave the crude product that was purified by MPLC (125 g silica gel column, eluting with 5% MeOH/EtOAc) to afford the title compound.

Step B: 4-(1-oxa-4,9-diazaspiro[5.5]undecan-4-yl) furan-2(5H)-one tert-butyl 4-(5-oxo-2,5-dihydrofuran-3-yl)-1-oxa-4,9-diazaspiro[5.5]undecane-9-carboxylate (617 mg, 1.823 mmol) was dissolved in DCM (2 mL) at rt and was treated with TFA (1 mL, 13 mmol) at rt for 2 hours. Then solvent was removed and the residue was dissolved in small amount of EtOAc and evaporated. This last step was repeated 3 times and the product was further dried by storing under high vacuum. LC/MS (M+H)+ 239

INTERMEDIATE 42

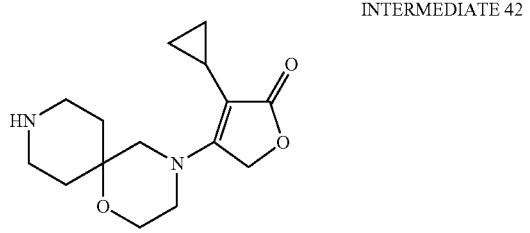 [SMILES: O=C1OCC(N2CCOC3(CCNCC3)C2)=C1C1CC1]

3-cyclopropyl-4-(1-oxa-4,9-diazaspiro[5.5]undecan-4-yl)furan-2(5H)-one

Step A: tert-Butyl 4-(4-bromo-5-oxo-2,5-dihydrofuran-3-yl)-1-oxa-4,9-diazaspiro[5.5]undecane-9-carboxylate tert-Butyl 1-oxa-4,9-diazaspiro[5.5]undecane-9-carboxylate (200 mg, 0.780 mmol) was mixed with DIEA (150 µl, 0.859 mmol) in THF (4 mL). 3,4-Dibromofuran-2(5H)-one (200 mg, 0.827 mmol) was added. The reaction mixture was stirred at 40° C. overnight. The solvent was then removed on rotavapor and the residue was purified by ISCO (0-10% MeOH/DCM, gradient, 40 g silica gel column). Removing solvents gave tert-butyl 4-(4-bromo-5-oxo-2,5-dihydrofuran-3-yl)-1-oxa-4,9-diazaspiro[5.5]undecane-9-carboxylate.

Step B: tert-Butyl 4-(4-cyclopropyl-5-oxo-2,5-dihydrofuran-3-yl)-1-oxa-4,9-diazaspiro[5.5]undecane-9-carboxylate tert-Butyl 4-(4-bromo-5-oxo-2,5-dihydrofuran-3-yl)-1-oxa-4,9-diazaspiro[5.5]undecane-9-carboxylate (315 mg, 0.755 mmol) was dissolved in toluene (5 mL). Cyclopropanylboronic acid (78 mg, 0.906 mmol) and K₃PO₄.3H₂O (663 mg, 2.491 mmol) were added. After degassing with bubbling N₂ for 10 minutes, Pd(Ph₃P)₄ (43.6 mg, 0.038 mmol) was added. The mixture was allowed to stir at 100° C. for 4 hours. After cooling down to rt, the solvent was removed on rotavapor and the residue was dissolved in EtOAc (50 mL) and washed with water (30 mL) and brine (30 mL), then dried over Na₂SO₄. Removing solvent gave the crude product that was purified by ISCO (0-100% EtOAc/Hexane gradient). Concentration gave tert-butyl 4-(4-cyclopropyl-5-oxo-2,5-dihydrofuran-3-yl)-1-oxa-4,9-diazaspiro[5.5]undecane-9-carboxylate. LC-MS 379 (M+1).

Step C: 3-Cyclopropyl-4-(1-oxa-4,9-diazaspiro[5.5]undecan-4-yl)furan-2(5H)-one tert-Butyl 4-(4-cyclopropyl-5-oxo-2,5-dihydrofuran-3-yl)-1-oxa-4,9-diazaspiro[5.5]undecane-9-carboxylate (144 mg, 0.380 mmol) was dissolved in DCM (1 mL) and treated with TFA (0.5 mL). The mixture was stirred at rt for 2 hours and then the solvent was removed. The residue was co-evaporated with DCM (3λ) to take out all the TFA. LC-MS 279 (M+1).

INTERMEDIATE 43

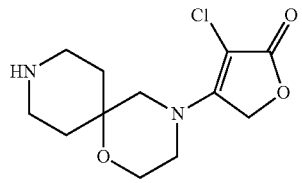

3-chloro-4-(1-oxa-4,9-diazaspiro[5.5]undecan-4-yl) furan-2(5H)-one 4-(4-chloro-5-oxo-2,5-dihydrofuran-3-yl)-1-oxa-4,9-diazaspiro[5.5]undecane-9-carboxylate tert-Butyl 1-oxa-4,9-diazaspiro[5.5]undecane-9-carboxylate (200 mg, 0.780 mmol) and 3,4-dichlorofuran-2(5H)-one (119 mg, 0.780 mmol) were mixed in THF (4 mL). DIEA (0.164 mL, 0.936 mmol) was added. The mixture was stirred at rt for 72 hours. The solvent was then removed on rotavapor and the residue was purified by ISCO (0-10% MeOH/DCM). Removing solvents gave tert-butyl 4-(4-chloro-5-oxo-2,5-dihydrofuran-3-yl)-1-oxa-4,9-diazaspiro[5.5]undecane-9-carboxylate. LC-MS 317 (M-56+1).

Step B: 3-Chloro-4-(1-oxa-4,9-diazaspiro[5.5]undecan-4-yl)furan-2(5H)-one

3-Chloro-4-(1-oxa-4,9-diazaspiro[5.5]undecan-4-yl) furan-2(5H)-one was prepared in a similar fashion to the synthesis of 3-cyclopropyl-4-(1-oxa-4,9-diazaspiro[5.5]undecan-4-yl)furan 2(5H)-one from tert-butyl 4-(4-chloro-5-oxo-2,5-dihydrofuran-3-yl)-1-oxa-4,9-diazaspiro[5.5]undecane-9-carboxylate. LC-MS 273 (M+1).

INTERMEDIATE 44

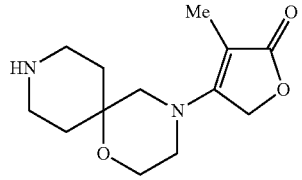

3-methyl-4-(1-oxa-4,9-diazaspiro[5.5]undecan-4-yl) furan-2(5H)-one

Step A: tert-butyl 4-(4-methyl-5-oxo-2,5-dihydrofuran-3-yl)-1-oxa-4,9-diazaspiro[5.5]undecane-9-carboxylate 4-Hydroxy-3-methylfuran-2(5H)-one (Intermediate 4, Step B, 205 mg, 1.80 mmol) and tert-Butyl 1-oxa-4,9-diazaspiro[5.5]undecane-9-carboxylate (461 mg, 1.80 mmol) were mixed with acetic ACID (0.103 mL, 1.80 mmol) in 2-Propanol (5 mL). The mixture was heated up to 108° C. and stir overnight. On the next day the solvent was removed and the residue was purified by MPLC (40 g silica gel column) and was eluted by 0-100% EtOAc/hexane gradient. Removing solvent gave the title product.

Step B: 3-methyl-4-(1-oxa-4,9-diazaspiro[5.5]undecan-4-yl)furan-2(5H)-one tert-Butyl 4-(4-methyl-5-oxo-2,5-dihydrofuran-3-yl)-1-oxa-4,9-diazaspiro[5.5]undecane-9-carboxylate (630 mg, 1.79 mmol) was dissolved in DCM (4 mL) and was treated with TFA (2 mL, 26 mmol) at rt for 2 hours. Then solvent was removed. The residue was dissolved in small amount of DCM and evaporated to dryness (repeat 3 times). Then it was dried under high vacuum for 2 hours. Crude product was used directly in the next step. LC/MS (M+H)$^+$ 253

Example 1

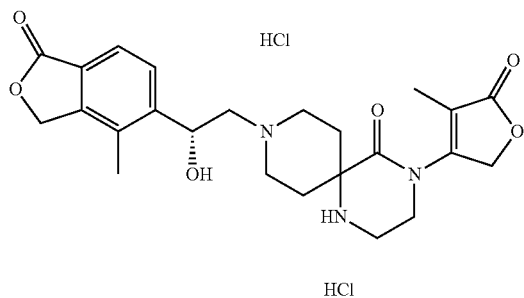 [SMILES: CC1=C(N2CCNC3(CCN(C[C@H](O)c4ccc5c(c4C)COC5=O)CC3)C2=O)COC1=O ; Cl ; Cl]

9-[(2R)-2-hydroxy-2-(4-methyl-1-oxo-1,3-dihydro-2-benzofuran-5-yl)ethyl]-4-(4-methyl-5-oxo-2,5-dihydrofuran-3-yl)-1,4,9-triazaspiro[5.5]undecan-5-one dihydrochloride Step A: benzyl 9-[(2R)-2-hydroxy-2-(4-methyl-1-oxo-1,3-dihydro-2-benzofuran-5-yl)ethyl]-4-(4-methyl-5-oxo-2,5-dihydrofuran-3-yl)-5-oxo-1,4,9-triazaspiro[5.5]undecane-1-carboxylate An EtOH solution (5 mL) of benzyl 4-(4-methyl-5-oxo-2,5-dihydrofuran-3-yl)-5-oxo-1,4,9-triazaspiro[5.5]undecane-1-carboxylate (Int. 21, 280 mg, 0.701 mmol) was treated with 4-methyl-5-[(2R)-oxiran-2-yl]-2-benzofuran-1(3H)-one (Int. 3B, 200 mg, 1.05 mmol) and stirred at 80° C. for 20 hours. The reaction mixture was cooled to ambient temperature, concentrated in vacuo and the crude residue purified via MPLC (0-5% MeOH/DCM gradient) and then purified again via MPLC (0-100% EtOAc/Hex gradient). The double purification afforded benzyl 9-[(2R)-2-hydroxy-2-(4-methyl-1-oxo-1,3-dihydro-2-benzofuran-5-yl)ethyl]-4-(4-methyl-5-oxo-2,5-dihydrofuran-3-yl)-5-oxo-1,4,9-triazaspiro[5.5]undecane-1-carboxylate and benzyl 9-[2-hydroxy-1-(4-methyl-1-oxo-1,3-dihydro-2-benzofuran-5-yl)ethyl]-4-(4-methyl-5-oxo-2,5-dihydrofuran-3-yl)-5-oxo-1,4,9-triazaspiro[5.5]undecane-1-carboxylate as a mixture of epoxide opening regioisomers. (M+H)$^+$ 590

Step B: 9-[(2R)-2-hydroxy-2-(4-methyl-1-oxo-1,3-dihydro-2-benzofuran-5-yl)ethyl]-4-(4-methyl-5-oxo-2,5-dihydrofuran-3-yl)-1,4,9-triazaspiro[5.5]undecan-5-one dihydrochloride A regioisomeric solution of benzyl 9-[(2R)-2-hydroxy-2-(4-methyl-1-oxo-1,3-dihydro-2-benzofuran-5-yl)ethyl]-4-(4-methyl-5-oxo-2,5-dihydrofuran-3-yl)-5-oxo-1,4,9-triazaspiro[5.5]undecane-1-carboxylate and benzyl 9-[2-hydroxy-1-(4-methyl-1-oxo-1,3-dihydro-2-benzofuran-5-yl)ethyl]-4-(4-methyl-5-oxo-2,5-dihydrofuran-3-yl)-5-oxo-1,4,9-triazaspiro[5.5]undecane-1-carboxylate (250.9 mg, 0.426 mmol) in DCM (20 mL) was treated with palladium on carbon (63 mg, 0.592 mmol) followed by MeOH (4 mL). The atmosphere in the reaction vessel was evacuated and purged with H$_2$ (3 cycles) and the reaction mixture was stirred under a balloon of H$_2$ over 15 h. The reaction mixture was filtered through a plug of CELITE (rinsing with MeOH and DCM) and concentrated in vacuo. The regioisomers were separated by SFC on a CHIRALCEL OD column eluting with 30% MeOH containing 0.2% DEA. The desired fractions were combined, concentrated in vacuo, dissolved in DCM and treated with excess 1N HCl in ether solution. The resulting suspension was concentrated in vacuo to afford the title compound. (M+H)$^+$ 456.

The following compounds were prepared in an analogous fashion as described for 9-[(2R)-2-hydroxy-2-(4-methyl-1-oxo-1,3-dihydro-2-benzofuran-5-yl)ethyl]-4-(4-methyl-5-oxo-2,5-dihydrofuran-3-yl)-1,4,9-triazaspiro[5.5]undecan-5-one dihydrochloride (Example 1), immediately above, using the epoxide intermediates indicated and benzyl 4-(4-methyl-5-oxo-2,5-dihydrofuran-3-yl)-5-oxo-1,4,9-triazaspiro[5.5]undecane-1-carboxylate (Int. 21).

TABLE 4

| Int. # | Epoxide Intermediate | Structure | LC-MS (ESI, m/z) | IUPAC name |
|---|---|---|---|---|
| 2A | 8A | 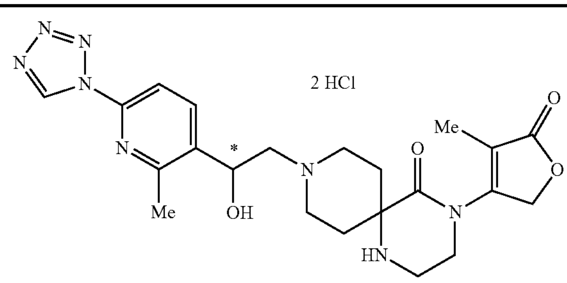 | 469 | 9-(2-hydroxy-2-(2-methyl-6-(1H-tetrazol-1-yl)pyridin-3-yl)ethyl)-4-(4-methyl-5-oxo-2,5-dihydrofuran-3-yl)-1,4,9-triazaspiro[5.5]undecan-5-one (single enantiomer, absolute stereochemistry not established) |

TABLE 4-continued

| Int. # | Epoxide Intermediate | Structure | LC-MS (ESI, m/z) | IUPAC name |
|---|---|---|---|---|
| 2B | 8B | 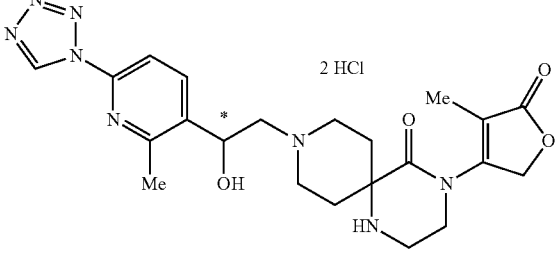 | 469 | 9-(2-hydroxy-2-(2-methyl-6-(1H-tetrazol-1-yl)pyridin-3-yl)ethyl)-4-(4-methyl-5-oxo-2,5-dihydrofuran-3-yl)-1,4,9-triazaspiro[5.5]undecan-5-one (single enantiomer, absolute stereochemistry not established, but opposite to 2A) |
| 3A | 6A | 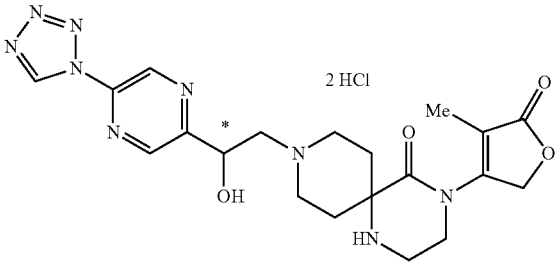 [SMILES: CC1=C(N2CCNC3(CCN(CC(O)c4cnc(-n5cnnn5)cn4)CC3)C2=O)COC1=O] | 456 | 9-(2-(5-(1H-tetrazol-1-yl)pyrazin-2-yl)-2-hydroxyethyl)-4-(4-methyl-5-oxo-2,5-dihydrofuran-3-yl)-1,4,9-triazaspiro[5.5]undecan-5-one (single enantiomer, absolute stereochemistry not established) |
| 3B | 6B | 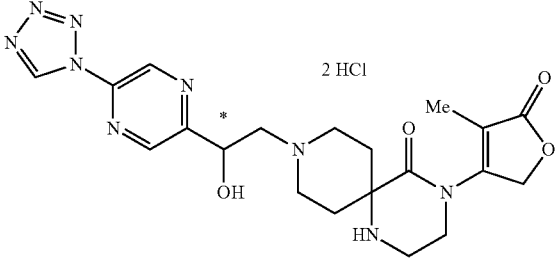 [SMILES: CC1=C(N2CCNC3(CCN(CC(O)c4cnc(-n5cnnn5)cn4)CC3)C2=O)COC1=O] | 456 | 9-(2-(5-(1H-tetrazol-1-yl)pyrazin-2-yl)-2-hydroxyethyl)-4-(4-methyl-5-oxo-2,5-dihydrofuran-3-yl)-1,4,9-triazaspiro[5.5]undecan-5-one (single enantiomer, absolute stereochemistry not established, but opposite to 3A) |
| 4A | 5A | 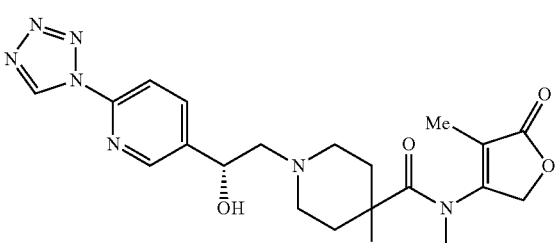 | 455 | (R)-9-(2-(6-(1H-tetrazol-1-yl)pyridin-3-yl)-2-hydroxyethyl)-4-(4-methyl-5-oxo-2,5-dihydrofuran-3-yl)-1,4,9-triazaspiro[5.5]undecan-5-one |
| 4B | 5B | 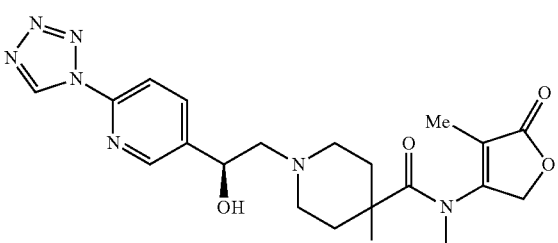 | 455 | (S)-9-(2-(6-(1H-tetrazol-1-yl)pyridin-3-yl)-2-hydroxyethyl)-4-(4-methyl-5-oxo-2,5-dihydrofuran-3-yl)-1,4,9-triazaspiro[5.5]undecan-5-one |

TABLE 4-continued

| Int. # | Epoxide Intermediate | Structure | LC-MS (ESI, m/z) | IUPAC name |
|---|---|---|---|---|
| 5A | 11A | 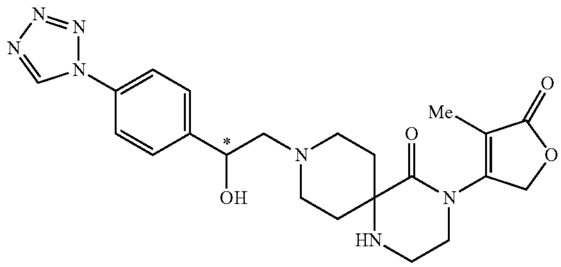 [SMILES: CC1=C(N2CCNC3(CCN(CC(O)c4ccc(-n5cnnn5)cc4)CC3)C2=O)COC1=O] | 454 | 9-(2-(4-(1H-tetrazol-1-yl)phenyl)-2-hydroxyethyl)-4-(4-methyl-5-oxo-2,5-dihydrofuran-3-yl)-1,4,9-triazaspiro[5.5]undecan-5-one (single enantiomer, absolute stereochemistry not established) |
| 5B | 11B | 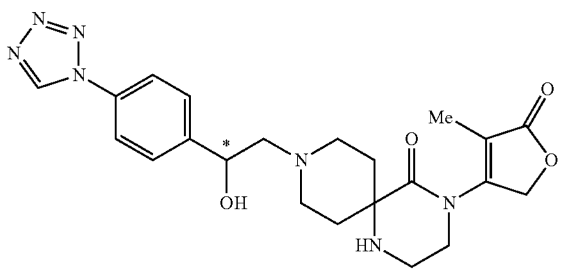 [SMILES: CC1=C(N2CCNC3(CCN(CC(O)c4ccc(-n5cnnn5)cc4)CC3)C2=O)COC1=O] | 454 | 9-(2-(4-(1H-tetrazol-1-yl)phenyl)-2-hydroxyethyl)-4-(4-methyl-5-oxo-2,5-dihydrofuran-3-yl)-1,4,9-triazaspiro[5.5]undecan-5-one (single enantiomer, absolute stereochemistry not established, but opposite to 5A) |

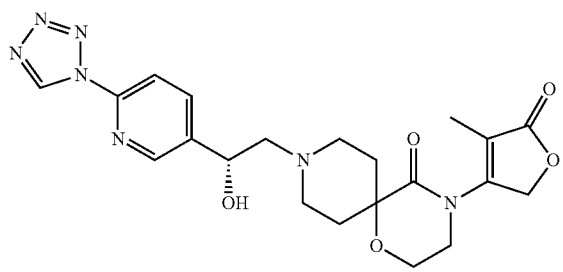

(R)-9-(2-(6-(1H-tetrazol-1-yl)pyridin-3-yl)-2-hydroxyethyl)-4-(4-methyl-5-oxo-2,5-dihydrofuran-3-yl)-1-oxa-4,9-diazaspiro[5.5]undecan-5-one A solution of 4-(4-methyl-5-oxo-2,5-dihydrofuran-3-yl)-1-oxa-4,9-diazaspiro[5.5]undecan-5-one (Int. 24, 620 mg, 2.33 mmol) and (R)-5-(oxiran-2-yl)-2-(1H-tetrazol-1-yl)pyridine (Int. 5A, 529 mg, 2.79 mmol) in ethanol (20 mL) was heated at 95° C. overnight. After removing the volatile materials, the residue was purified by preparative TLC using 10% MeOH/DCM. The resulting material was further purified by trituration using 20 mL methanol, and the solid collected by filtration to give the title compound. LC/MS: (M+1)⁺: 456.

The Examples in the table below were prepared in an analogous fashion as that described for (R)-9-(2-(6-(1H-tetrazol-1-yl)pyridin-3-yl)-2-hydroxyethyl)-4-(4-methyl-5-oxo-2,5-dihydrofuran-3-yl)-1-oxa-4,9-diazaspiro[5.5]undecan-5-one from the amine and epoxide Intermediates indicated, which were all prepared as described above.

TABLE 5

| # | Intermediates | Structure | LC-MS M + 1 | IUPAC name |
|---|---|---|---|---|
| 6B | 5B, 24 | 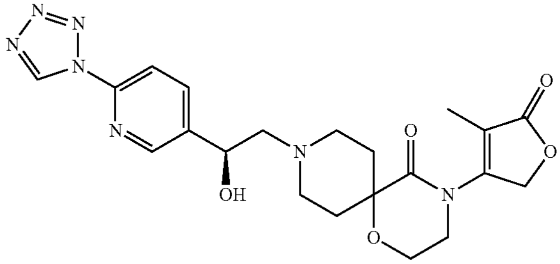 [SMILES: CC1=C(N2CCOC3(CCN(C[C@H](O)c4ccc(-n5cnnn5)nc4)CC3)C2=O)COC1=O] | 456 | (S)-9-(2-(6-(1H-tetrazol-1-yl)pyridin-3-yl)-2-hydroxyethyl)-4-(4-methyl-5-oxo-2,5-dihydrofuran-3-yl)-1-oxa-4,9-diazaspiro[5.5]undecan-5-one |

TABLE 5-continued

| # | Intermediates | Structure | LC-MS M + 1 | IUPAC name |
|---|---|---|---|---|
| 7A | 5A, 26 | 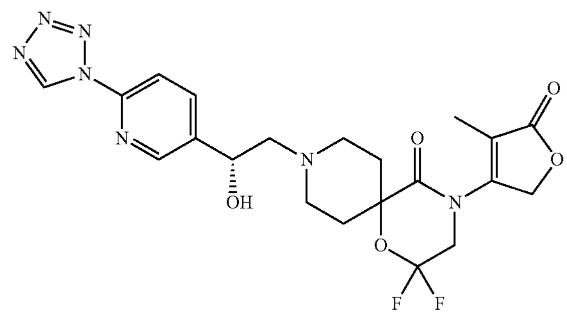 [SMILES: CC1=C(N2CC(F)(F)OC3(CCN(C[C@H](O)c4ccc(-n5cnnn5)nc4)CC3)C2=O)COC1=O] | 478 | (R)-4-(9-(2-(6-(1H-tetrazol-1-yl)pyridin-3-yl)-2-hydroxyethyl)-2,2-difluoro-1-oxa-4,9-diazaspiro[5.5]undecan-4-yl)-3-methylfuran-2(5H)-one |
| 7B | 5B, 26 | 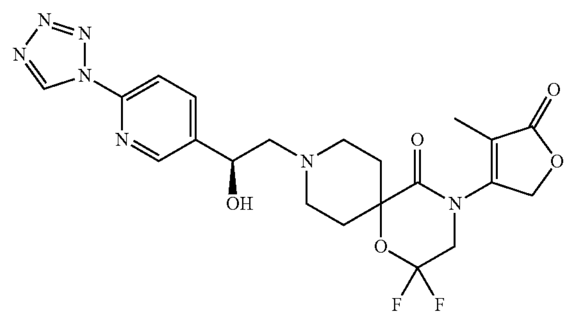 [SMILES: CC1=C(N2CC(F)(F)OC3(CCN(C[C@@H](O)c4ccc(-n5cnnn5)nc4)CC3)C2=O)COC1=O] | 478 | (S)-4-(9-(2-(6-(1H-tetrazol-1-yl)pyridin-3-yl)-2-hydroxyethyl)-2,2-difluoro-1-oxa-4,9-diazaspiro[5.5]undecan-4-yl)-3-methylfuran-2(5H)-one |
| 8A | 3B, 24 | 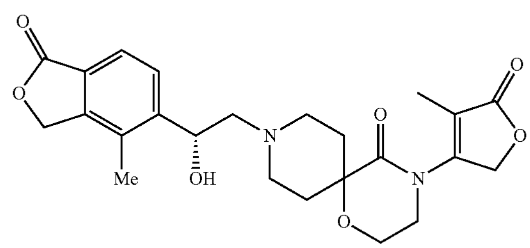 [SMILES: CC1=C(N2CCOC3(CCN(C[C@H](O)c4ccc5c(c4C)COC5=O)CC3)C2=O)COC1=O] | 457 | (R)-9-(2-hydroxy-2-(4-methyl-1-oxo-1,3-dihydroisobenzofuran-5-yl)ethyl)-4-(4-methyl-5-oxo-2,5-dihydrofuran-3-yl)-1-oxa-4,9-diazaspiro[5.5]undecan-5-one |
| 8B | 3A, 24 | 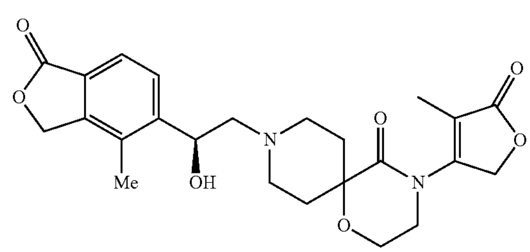 [SMILES: CC1=C(N2CCOC3(CCN(C[C@@H](O)c4ccc5c(c4C)COC5=O)CC3)C2=O)COC1=O] | 457 | (S)-9-(2-hydroxy-2-(4-methyl-1-oxo-1,3-dihydroisobenzofuran-5-yl)ethyl)-4-(4-methyl-5-oxo-2,5-dihydrofuran-3-yl)-1-oxa-4,9-diazaspiro[5.5]undecan-5-one |
| 9A | 11A, 24 | 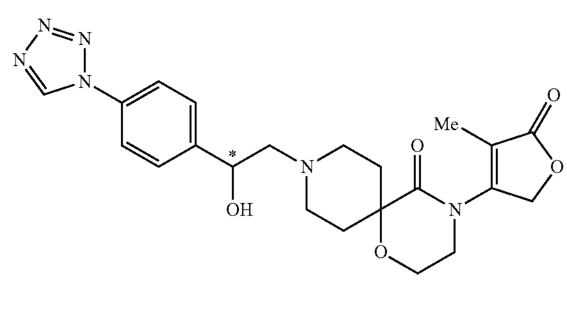 [SMILES: CC1=C(N2CCOC3(CCN(CC(O)c4ccc(-n5cnnn5)cc4)CC3)C2=O)COC1=O] | 455 | 9-(2-(4-(1H-tetrazol-1-yl)phenyl)-2-hydroxyethyl)-4-(4-methyl-5-oxo-2,5-dihydrofuran-3-yl)-1-oxa-4,9-diazaspiro[5.5]undecan-5-one (single enantiomer, absolute stereochemistry not established) |

TABLE 5-continued

| # | Intermediates | Structure | LC-MS M + 1 | IUPAC name |
|---|---|---|---|---|
| 9B | 11B, 24 | 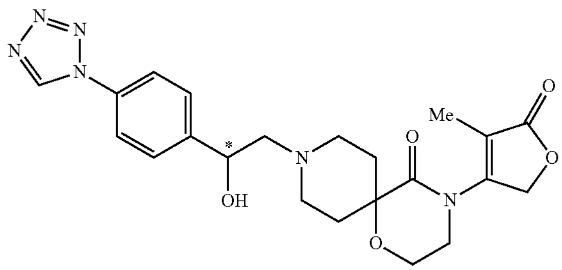 | 455 | 9-(2-(4-(1H-tetrazol-1-yl)phenyl)-2-hydroxyethyl)-4-(4-methyl-5-oxo-2,5-dihydrofuran-3-yl)-1-oxa-4,9-diazaspiro[5.5]undecan-5-one (single enantiomer, absolute stereochemistry not established, but opposite to 9A) |
| 10A | 5B, 35A | 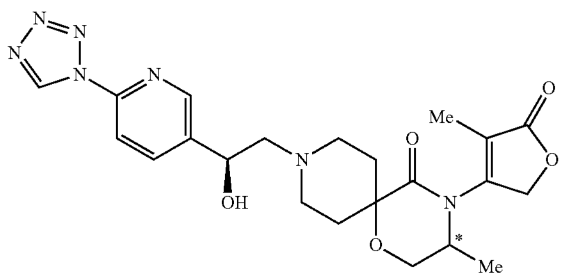 [SMILES: CC1=C(N2C(=O)C3(CCN(C[C@@H](O)c4ccc(-n5cnnn5)nc4)CC3)OCC2C)COC1=O] | 470 | 9-((S)-2-(6-(1H-tetrazol-1-yl)pyridin-3-yl)-2-hydroxyethyl)-3-methyl-4-(4-methyl-5-oxo-2,5-dihydrofuran-3-yl)-1-oxa-4,9-diazaspiro[5.5]undecan-5-one (single isomer, absolute stereochemistry not established on morpholinone) |
| 10B | 5A, 35B | 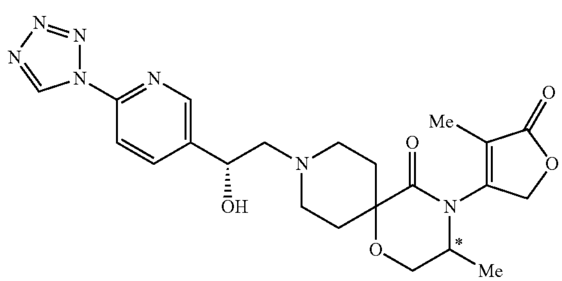 [SMILES: CC1=C(N2C(=O)C3(CCN(C[C@H](O)c4ccc(-n5cnnn5)nc4)CC3)OCC2C)COC1=O] | 470 | 9-((R)-2-(6-(1H-tetrazol-1-yl)pyridin-3-yl)-2-hydroxyethyl)-3-methyl-4-(4-methyl-5-oxo-2,5-dihydrofuran-3-yl)-1-oxa-4,9-diazaspiro[5.5]undecan-5-one (single isomer, absolute stereochemistry not established on morpholinone) |
| 10C | 5B, 35B | 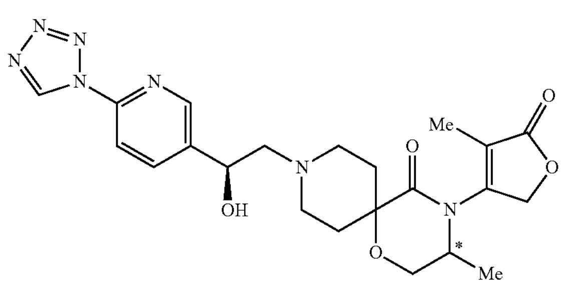 [SMILES: CC1=C(N2C(=O)C3(CCN(C[C@@H](O)c4ccc(-n5cnnn5)nc4)CC3)OCC2C)COC1=O] | 470 | 9-((S)-2-(6-(1H-tetrazol-1-yl)pyridin-3-yl)-2-hydroxyethyl)-3-methyl-4-(4-methyl-5-oxo-2,5-dihydrofuran-3-yl)-1-oxa-4,9-diazaspiro[5.5]undecan-5-one (single isomer, absolute stereochemistry not established on morpholinone, but opposite to Example 10A) |
| 11 | 3B, 35A | 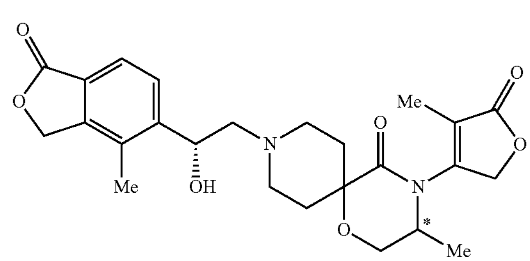 [SMILES: CC1=C(N2C(=O)C3(CCN(C[C@H](O)c4ccc5c(c4C)COC5=O)CC3)OCC2C)COC1=O] | 471 | 9-((R)-2-hydroxy-2-(4-methyl-1-oxo-1,3-dihydroisobenzofuran-5-yl)ethyl)-3-methyl-4-(4-methyl-5-oxo-2,5-dihydrofuran-3-yl)-1-oxa-4,9-diazaspiro[5.5]undecan-5-one (single diastereomer, absolute stereochemistry not established on morpholinone) |

TABLE 5-continued

| # | Intermediates | Structure | LC-MS M + 1 | IUPAC name |
|---|---|---|---|---|
| 12 | 5A, 40 | 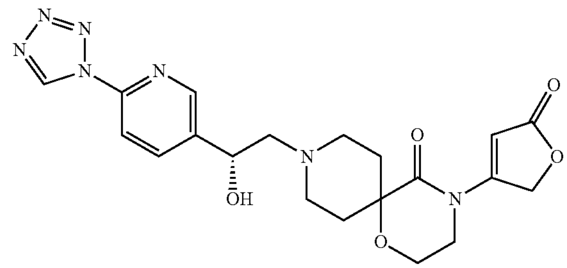 [SMILES: O=C1C=C(N2CCOC3(CCN(C[C@H](O)c4ccc(-n5cnnn5)nc4)CC3)C2=O)CO1] | 442 | (R)-9-(2-(6-(1H-tetrazol-1-yl)pyridin-3-yl)-2-hydroxyethyl)-4-(5-oxo-2,5-dihydrofuran-3-yl)-1-oxa-4,9-diazaspiro[5.5]undecan-5-one |
| 13A | 5B, 34B | 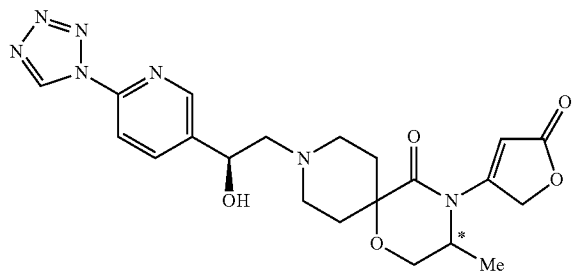 [SMILES: CC1COC2(CCN(C[C@@H](O)c3ccc(-n4cnnn4)nc3)CC2)C(=O)N1C1=CC(=O)OC1] | 456 | 9-((S)-2-(6-(1H-tetrazol-1-yl)pyridin-3-yl)-2-hydroxyethyl)-3-methyl-4-(5-oxo-2,5-dihydrofuran-3-yl)-1-oxa-4,9-diazaspiro[5.5]undecan-5-one (single diastereomer, absolute stereochemistry not established on morpholinone) |
| 13B | 5A, 34A | 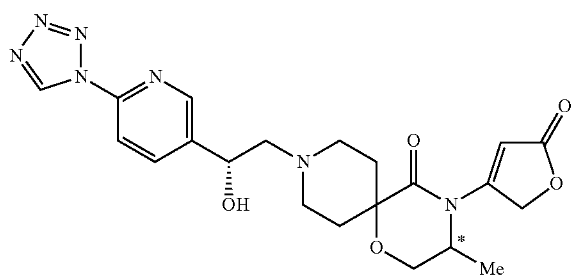 [SMILES: CC1COC2(CCN(C[C@H](O)c3ccc(-n4cnnn4)nc3)CC2)C(=O)N1C1=CC(=O)OC1] | 456 | 9-((R)-2-(6-(1H-tetrazol-1-yl)pyridin-3-yl)-2-hydroxyethyl)-3-methyl-4-(5-oxo-2,5-dihydrofuran-3-yl)-1-oxa-4,9-diazaspiro[5.5]undecan-5-one (single diastereomer, absolute stereochemistry not established on morpholinone) |
| 14 | 3B, 34A | 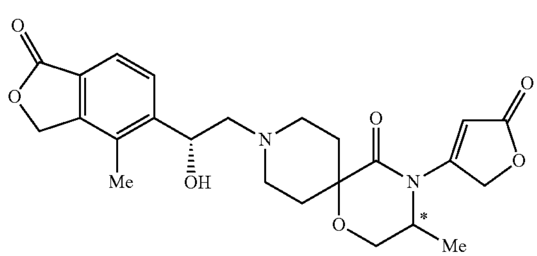 [SMILES: Cc1c([C@@H](O)CN2CCC3(CC2)OCC(C)N(C2=CC(=O)OC2)C3=O)ccc2c1COC2=O] | 457 | 9-((R)-2-hydroxy-2-(4-methyl-1-oxo-1,3-dihydroisobenzofuran-5-yl)ethyl)-3-methyl-4-(5-oxo-2,5-dihydrofuran-3-yl)-1-oxa-4,9-diazaspiro[5.5]undecan-5-one (single diastereomer, absolute stereochemistry not established on morpholinone) |
| 15 | 5B, 36 | 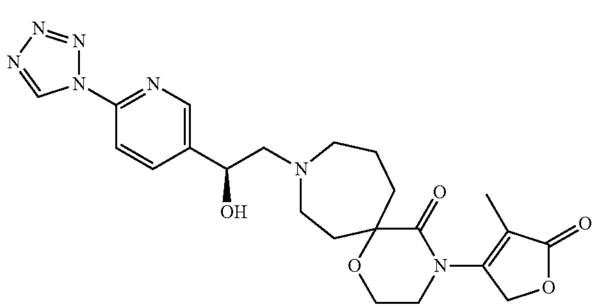 [SMILES: CC1=C(N2CCOC3(CCCN(C[C@@H](O)c4ccc(-n5cnnn5)nc4)CC3)C2=O)COC1=O] | 470 | 9-((S)-2-(6-(1H-tetrazol-1-yl)pyridin-3-yl)-2-hydroxyethyl)-4-(4-methyl-5-oxo-2,5-dihydrofuran-3-yl)-1-oxa-4,9-diazaspiro[5.6]dodecan-5-one |

TABLE 5-continued

| # | Intermediates | Structure | LC-MS M + 1 | IUPAC name |
|---|---|---|---|---|
| 16 | 3B, 20 | 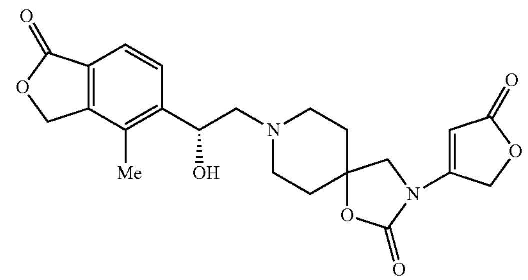 [SMILES: Cc1c([C@@H](O)CN2CCC3(CC2)CN(C2=CC(=O)OC2)C(=O)O3)ccc2c1COC2=O] | 429 | (R)-8-(2-hydroxy-2-(4-methyl-1-oxo-1,3-dihydroisobenzofuran-5-yl)ethyl)-3-(5-oxo-2,5-dihydrofuran-3-yl)-1-oxa-3,8-diazaspiro[4.5]decan-2-one |
| 17 | 8B, 20 | 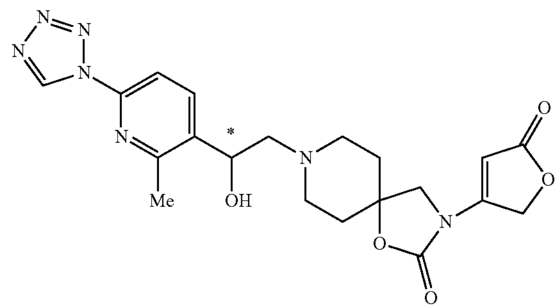 [SMILES: Cc1nc(-n2cnnn2)ccc1C(O)CN1CCC2(CC1)CN(C1=CC(=O)OC1)C(=O)O2] | 442 | 8-(2-hydroxy-2-(2-methyl-6-(1H-tetrazol-1-yl)pyridin-3-yl)ethyl)-3-(5-oxo-2,5-dihydrofuran-3-yl)-1-oxa-3,8-diazaspiro[4.5]decan-2-one (single diastereomer, absolute stereochemistry not established) |
| 18A | 6A, 24 | 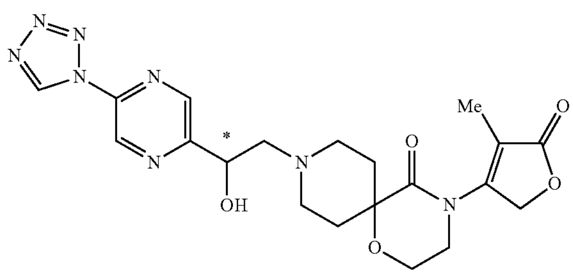 [SMILES: CC1=C(N2CCOC3(CCN(CC(O)c4cnc(-n5cnnn5)cn4)CC3)C2=O)COC1=O] | 457 | 9-(2-(5-(1H-tetrazol-1-yl)pyrazin-2-yl)-2-hydroxyethyl)-4-(4-methyl-5-oxo-2,5-dihydrofuran-3-yl)-1-oxa-4,9-diazaspiro[5.5]undecan-5-one (single diastereomer, absolute stereochemistry not established) |
| 18B | 6B, 24 | 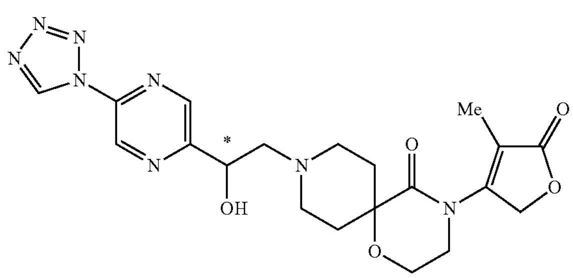 [SMILES: CC1=C(N2CCOC3(CCN(CC(O)c4cnc(-n5cnnn5)cn4)CC3)C2=O)COC1=O] | 457 | 9-(2-(5-(1H-tetrazol-1-yl)pyrazin-2-yl)-2-hydroxyethyl)-4-(4-methyl-5-oxo-2,5-dihydrofuran-3-yl)-1-oxa-4,9-diazaspiro[5.5]undecan-5-one (single diastereomer, absolute stereochemistry not established, but opposite from 18 A) |
| 19A | 5A, 41 | 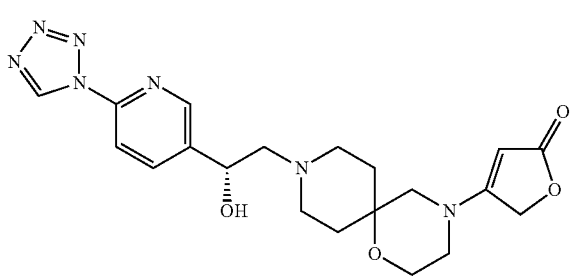 [SMILES: O=C1C=C(N2CCOC3(CCN(C[C@H](O)c4ccc(-n5cnnn5)nc4)CC3)C2)CO1] | 428 | (R)-4-(9-(2-(6-(1H-tetrazol-1-yl)pyridin-3-yl)-2-hydroxyethyl)-1-oxa-4,9-diazaspiro[5.5]undecan-4-yl)furan-2(5H)-one |

TABLE 5-continued

| # | Intermediates | Structure | LC-MS M + 1 | IUPAC name |
|---|---|---|---|---|
| 19B | 5B, 41 | 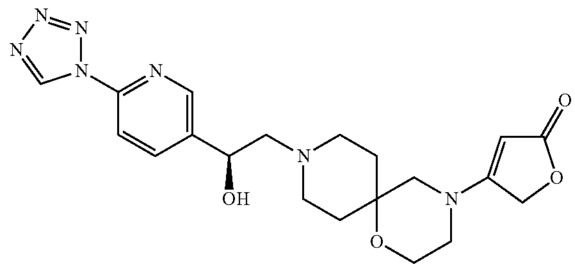 [SMILES: O=C1C=C(N2CCOC3(CCN(C[C@@H](O)c4ccc(-n5cnnn5)nc4)CC3)C2)CO1] | 428 | (S)-4-(9-(2-(6-(1H-tetrazol-1-yl)pyridin-3-yl)-2-hydroxyethyl)-1-oxa-4,9-diazaspiro[5.5]undecan-4-yl)furan-2(5H)-one |
| 20A | 8A, 41 | 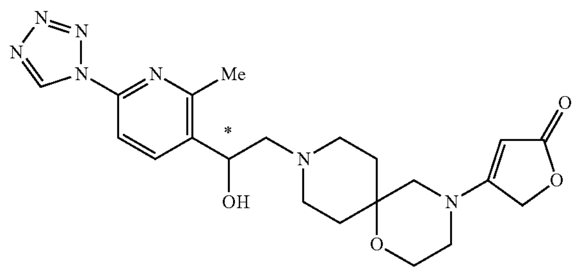 [SMILES: Cc1nc(-n2cnnn2)ccc1C(O)CN1CCC2(CC1)CN(C1=CC(=O)OC1)CCO2] | 442 | 4-(9-(2-hydroxy-2-(2-methyl-6-(1H-tetrazol-1-yl)pyridin-3-yl)ethyl)-1-oxa-4,9-diazaspiro[5.5]undecan-4-yl)furan-2(5H)-one (single diastereomer, absolute stereochemistry not established) |
| 20B | 8B, 41 | 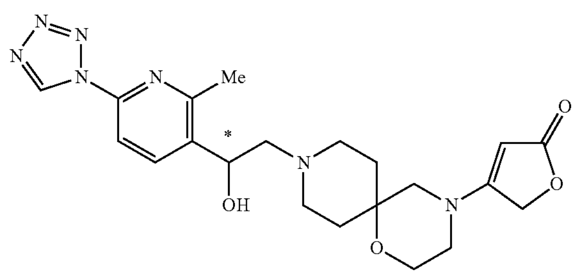 [SMILES: Cc1nc(-n2cnnn2)ccc1C(O)CN1CCC2(CC1)CN(C1=CC(=O)OC1)CCO2] | 442 | 4-(9-(2-hydroxy-2-(2-methyl-6-(1H-tetrazol-1-yl)pyridin-3-yl)ethyl)-1-oxa-4,9-diazaspiro[5.5]undecan-4-yl)furan-2(5H)-one (single diastereomer, absolute stereochemistry not established, but opposite from 20 A) |
| 21 | 3B, 44 | 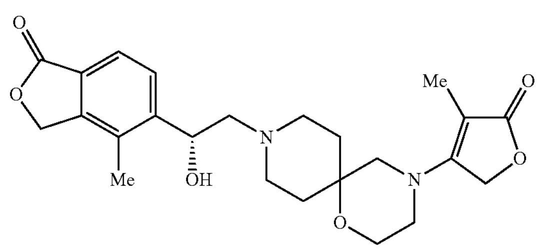 [SMILES: CC1=C(N2CCOC3(CCN(C[C@H](O)c4ccc5c(c4C)COC5=O)CC3)C2)COC1=O] | 443 | (R)-5-(1-hydroxy-2-(4-(4-methyl-5-oxo-2,5-dihydrofuran-3-yl)-1-oxa-4,9-diazaspiro[5.5]undecan-9-yl)ethyl)-4-methylisobenzofuran-1(3H)-one |
| 22A | 8A, 44 | 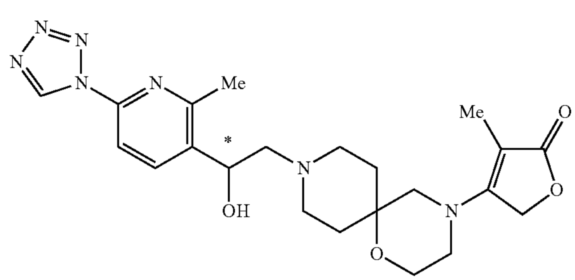 [SMILES: CC1=C(N2CCOC3(CCN(CC(O)c4ccc(-n5cnnn5)nc4C)CC3)C2)COC1=O] | 456 | 4-(9-(2-hydroxy-2-(2-methyl-6-(1H-tetrazol-1-yl)pyridin-3-yl)ethyl)-1-oxa-4,9-diazaspiro[5.5]undecan-4-yl)-3-methylfuran-2(5H)-one (single diastereomer, absolute stereochemistry not established) |

TABLE 5-continued

| # | Intermediates | Structure | LC-MS M + 1 | IUPAC name |
|---|---|---|---|---|
| 22B | 8B, 44 | 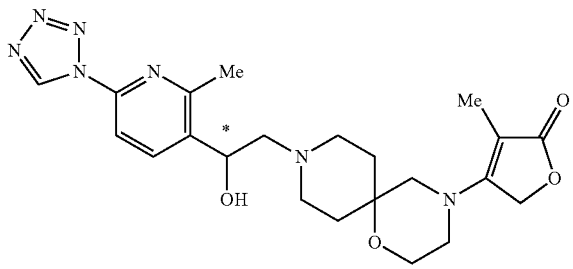 [SMILES: CC1=C(N2CCOC3(CCN(CC(O)c4ccc(-n5cnnn5)nc4C)CC3)C2)COC1=O] | 456 | 4-(9-(2-hydroxy-2-(2-methyl-6-(1H-tetrazol-1-yl)pyridin-3-yl)ethyl)-1-oxa-4,9-diazaspiro[5.5]undecan-4-yl)-3-methylfuran-2(5H)-one (single diastereomer, absolute stereochemistry not established, but opposite from 22 A) |
| 23 | 3B, 43 | 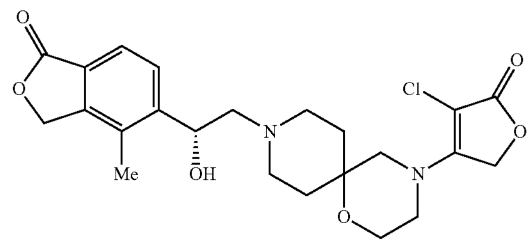 [SMILES: Cc1c([C@@H](O)CN2CCC3(CC2)CN(C2=C(Cl)C(=O)OC2)CCO3)ccc2c1COC2=O] | 463 | (R)-5-(2-(4-(4-chloro-5-oxo-2,5-dihydrofuran-3-yl)-1-oxa-4,9-diazaspiro[5.5]undecan-9-yl)-1-hydroxyethyl)-4-methylisobenzofuran-1(3H)-one |
| 24A | 5A, 43 | 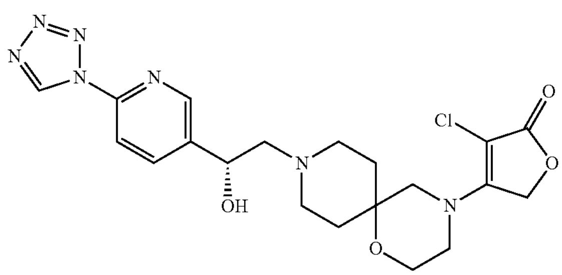 [SMILES: O=C1OCC(N2CCOC3(CCN(C[C@H](O)c4ccc(-n5cnnn5)nc4)CC3)C2)=C1Cl] | 462 | (R)-4-(9-(2-(6-(1H-tetrazol-1-yl)pyridin-3-yl)-2-hydroxyethyl)-1-oxa-4,9-diazaspiro[5.5]undecan-4-yl)furan-2(5H)-one |
| 24B | 5B, 43 | 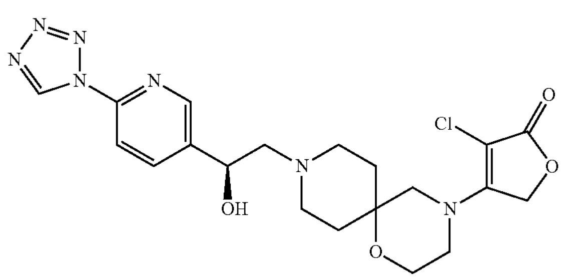 [SMILES: O=C1OCC(N2CCOC3(CCN(C[C@@H](O)c4ccc(-n5cnnn5)nc4)CC3)C2)=C1Cl] | 462 | (S)-4-(9-(2-(6-(1H-tetrazol-1-yl)pyridin-3-yl)-2-hydroxyethyl)-1-oxa-4,9-diazaspiro[5.5]undecan-4-yl)-3-chlorofuran-2(5H)-one |
| 25A | 8A, 43 | 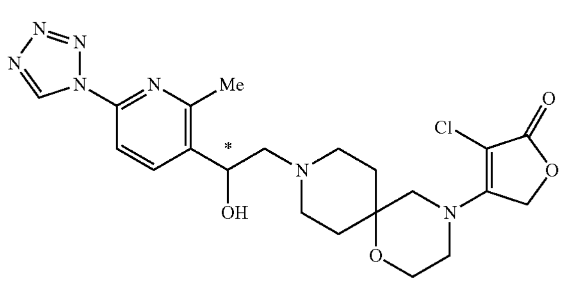 [SMILES: Cc1nc(-n2cnnn2)ccc1C(O)CN1CCC2(CC1)CN(C1=C(Cl)C(=O)OC1)CCO2] | 476 | 3-chloro-4-(9-(2-hydroxy-2-(2-methyl-6-(1H-tetrazol-1-yl)pyridin-3-yl)ethyl)-1-oxa-4,9-diazaspiro[5.5]undecan-4-yl)furan-2(5H)-one (single diastereomer, absolute stereochemistry not established) |

TABLE 5-continued

| # | Intermediates | Structure | LC-MS M + 1 | IUPAC name |
|---|---|---|---|---|
| 25B | 8B, 43 | 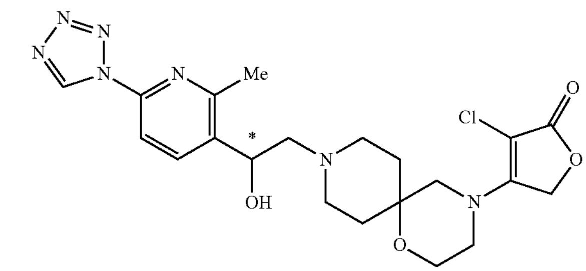 [SMILES: Cc1nc(-n2cnnn2)ccc1C(O)CN1CCC2(CC1)CN(C1=C(Cl)C(=O)OC1)CCO2] | 476 | 3-chloro-4-(9-(2-hydroxy-2-(2-methyl-6-(1H-tetrazol-1-yl)pyridin-3-yl)ethyl)-1-oxa-4,9-diazaspiro[5.5]undecan-4-yl)furan-2(5H)-one (single diastereomer, absolute stereochemistry not established, but opposite from 25 A) |
| 26A | 5A, 39 | 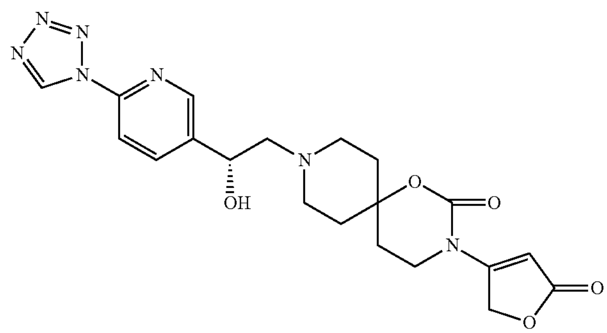 [SMILES: O=C1C=C(N2CCC3(CCN(C[C@H](O)c4ccc(-n5cnnn5)nc4)CC3)OC2=O)CO1] | 442 | (R)-9-(2-(6-(1H-tetrazol-1-yl)pyridin-3-yl)-2-hydroxyethyl)-3-(5-oxo-2,5-dihydrofuran-3-yl)-1-oxa-3,9-diazaspiro[5.5]undecan-2-one |
| 27 | 8A, 39 | 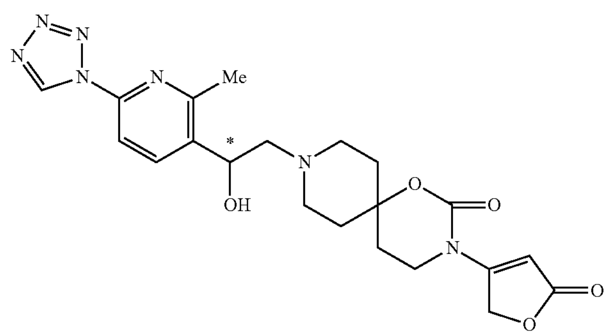 [SMILES: Cc1nc(-n2cnnn2)ccc1C(O)CN1CCC2(CC1)CCN(C1=CC(=O)OC1)C(=O)O2] | 456 | 9-(2-hydroxy-2-(2-methyl-6-(1H-tetrazol-1-yl)pyridin-3-yl)ethyl)-3-(5-oxo-2,5-dihydrofuran-3-yl)-1-oxa-3,9-diazaspiro[5.5]undecan-2-one (single diastereomer, absolute stereochemistry not established) |
| 28A | 5A, 42 | 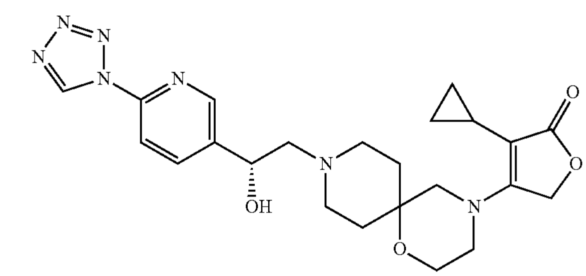 [SMILES: O=C1OCC(N2CCOC3(CCN(C[C@H](O)c4ccc(-n5cnnn5)nc4)CC3)C2)=C1C1CC1] | 468 | (S)-4-(9-(2-(6-(1H-tetrazol-1-yl)pyridin-3-yl)-2-hydroxyethyl)-1-oxa-4,9-diazaspiro[5.5]undcean-4-yl)-3-cyclopropylfuran-2(5H)-one |
| 28B | 5B, 42 | 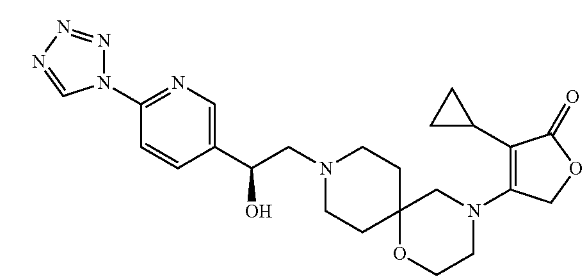 [SMILES: O=C1OCC(N2CCOC3(CCN(C[C@@H](O)c4ccc(-n5cnnn5)nc4)CC3)C2)=C1C1CC1] | 468 | (S)-4-(9-(2-(6-(1H-tetrazol-1-yl)pyridin-3-yl)-2-hydroxyethyl)-1-oxa-4,9-diazaspiro[5.5]undecan-4-yl)-3-cyclopropylfuran-2(5H)-one |

TABLE 5-continued

| # | Intermediates | Structure | LC-MS M + 1 | IUPAC name |
|---|---|---|---|---|
| 29A | 8A, 42 | 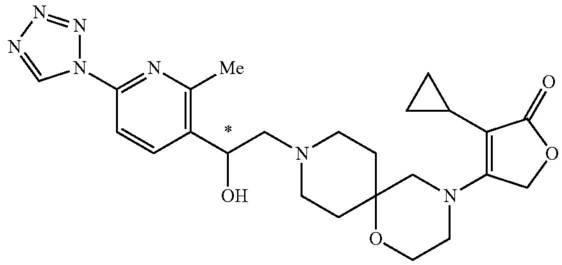 [SMILES: Cc1nc(-n2cnnn2)ccc1C(O)CN1CCC2(CC1)CN(C1=C(C3CC3)C(=O)OC1)CCO2] | 482 | 3-cyclopropyl-4-(9-(2-hydroxy-2-(2-methyl-6-(1H-tetrazol-1-yl)pyridin-3-yl)ethyl)-1-oxa-4,9-diazaspiro[5.5]undecan-4-yl)furan-2(5H)-one (single diastereomer, absolute stereochemistry not established, but opposite from 29B) |
| 29B | 8B, 42 | 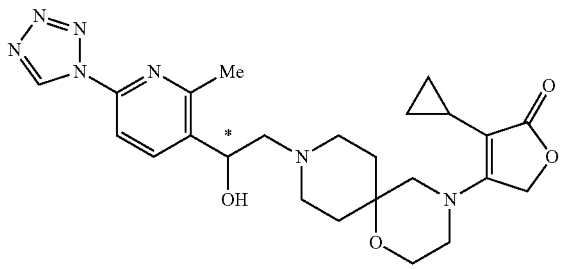 [SMILES: Cc1nc(-n2cnnn2)ccc1C(O)CN1CCC2(CC1)CN(C1=C(C3CC3)C(=O)OC1)CCO2] | 482 | 3-cyclopropyl-4-(9-(2-hydroxy-2-(2-methyl-6-(1H-tetrazol-1-yl)pyridin-3-yl)ethyl)-1-oxa-4,9-diazaspiro[5.5]undecan-4-yl)furan-2(5H)-one (single diastereomer, absolute stereochemistry not established, but opposite from 29A) |
| 30A | 12A, 41 | 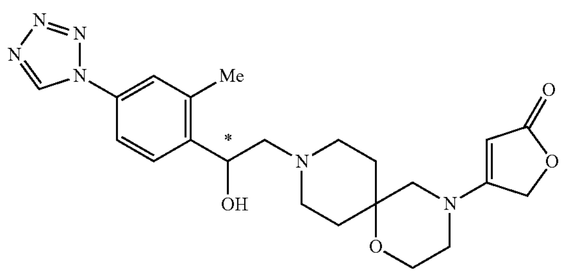 [SMILES: Cc1cc(-n2cnnn2)ccc1C(O)CN1CCC2(CC1)CN(C1=CC(=O)OC1)CCO2] | 441 | 4-(9-(2-hydroxy-2-(2-methyl-4-(1H-tetrazol-1-yl)phenyl)ethyl)-1-oxa-4,9-diazaspiro[5.5]undecan-4-yl)furan-2(5H)-one (single diastereomer, absolute stereochemistry not established, but opposite from 30B) |
| 30B | 12B, 41 | 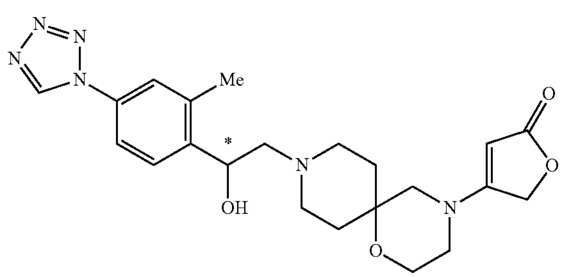 [SMILES: Cc1cc(-n2cnnn2)ccc1C(O)CN1CCC2(CC1)CN(C1=CC(=O)OC1)CCO2] | 441 | 4-(9-(2-hydroxy-2-(2-methyl-4-(1H-tetrazol-1-yl)phenyl)ethyl)-1-oxa-4,9-diazaspiro[5.5]undecan-4-yl)furan-2(5H)-one (single diastereomer, absolute stereochemistry not established, but opposite from 30A) |
| 31A | 12A, 44 | 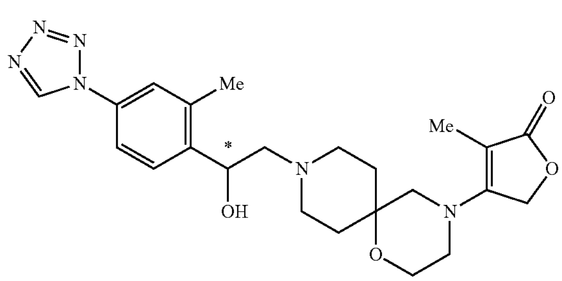 [SMILES: CC1=C(N2CCOC3(CCN(CC(O)c4ccc(-n5cnnn5)cc4C)CC3)C2)COC1=O] | 455 | 4-(9-(2-hydroxy-2-(2-methyl-4-(1H-tetrazol-1-yl)phenyl)ethyl)-1-oxa-4,9-diazaspiro[5.5]undecan-4-yl)-3-methylfuran-2(5H)-one (single diastereomer, absolute stereochemistry not established, but opposite from 31B) |

TABLE 5-continued

| # | Intermediates | Structure | LC-MS M + 1 | IUPAC name |
|---|---|---|---|---|
| 31B | 12B, 44 | 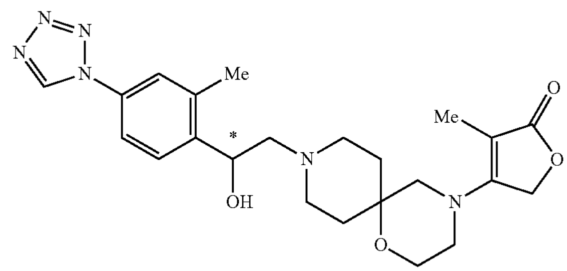 [SMILES: CC1=C(N2CCOC3(CCN(CC(O)c4ccc(-n5cnnn5)cc4C)CC3)C2)COC1=O] | 455 | 4-(9-(2-hydroxy-2-(2-methyl-4-(1H-tetrazol-1-yl)phenyl)ethyl)-1-oxa-4,9-diazaspiro[5.5]undecan-4-yl)-3-methylfuran-2(5H)-one (single diastereomer, absolute stereochemistry not established, but opposite from 31A) |
| 32A | 14A, 44 | 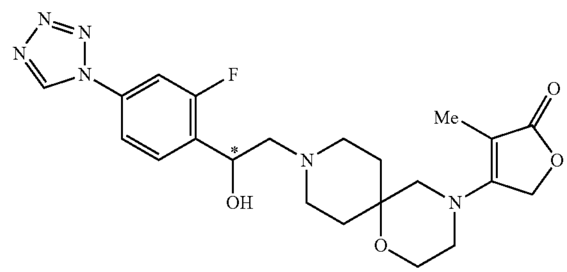 [SMILES: CC1=C(N2CCOC3(CCN(CC(O)c4ccc(-n5cnnn5)cc4F)CC3)C2)COC1=O] | 459 | 4-(9-(2-(2-fluoro-4-(1H-tetrazol-1-yl)phenyl)-2-hydroxyethyl)-1-oxa-4,9-diazaspiro[5.5]undecan-4-yl)-3-methylfuran-2(5H)-one (single diastereomer, absolute stereochemistry not established, but opposite from 32B) |
| 32B | 14B, 44 | 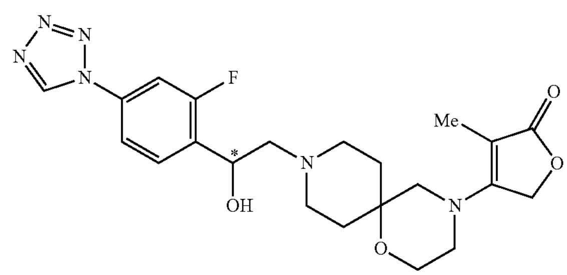 [SMILES: CC1=C(N2CCOC3(CCN(CC(O)c4ccc(-n5cnnn5)cc4F)CC3)C2)COC1=O] | 459 | 4-(9-(2-(2-fluoro-4-(1H-tetrazol-1-yl)phenyl)-2-hydroxyethyl)-1-oxa-4,9-diazaspiro[5.5]undecan-4-yl)-3-methylfuran-2(5H)-one (single diastereomer, absolute stereochemistry not established, but opposite from 32A) |
| 33A | 13A, 44 | 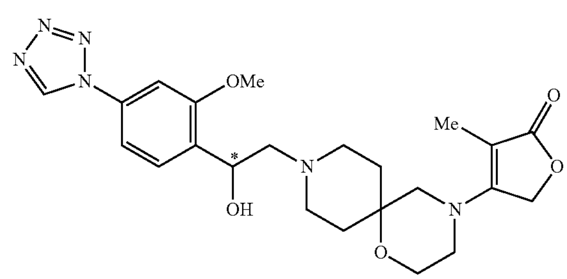 [SMILES: COc1cc(-n2cnnn2)ccc1C(O)CN1CCC2(CC1)CN(C1=C(C)C(=O)OC1)CCO2] | 471 | 4-(9-(2-hydroxy-2-(2-methoxy-4-(1H-tetrazol-1-yl)phenyl)ethyl)-1-oxa-4,9-diazaspiro[5.5]undecan-4-yl)-3-methylfuran-2(5H)-one (single diastereomer, absolute stereochemistry not established, but opposite from 33B) |
| 33B | 13B, 44 | 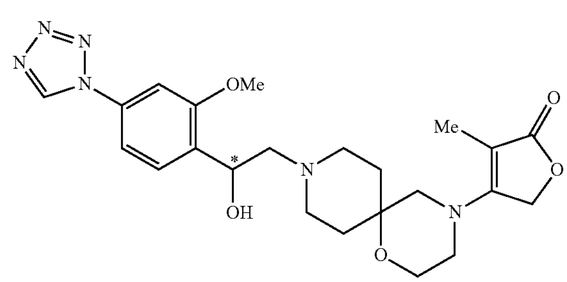 [SMILES: COc1cc(-n2cnnn2)ccc1C(O)CN1CCC2(CC1)CN(C1=C(C)C(=O)OC1)CCO2] | 471 | 4-(9-(2-hydroxy-2-(2-methoxy-4-(1H-tetrazol-1-yl)phenyl)ethyl)-1-oxa-4,9-diazaspiro[5.5]undecan-4-yl)-3-methylfuran-2(5H)-one (single diastereomer, absolute stereochemistry not established, but opposite from 33A) |

TABLE 5-continued

| # | Intermediates | Structure | LC-MS M + 1 | IUPAC name |
|---|---|---|---|---|
| 34 | 3B, 22 | 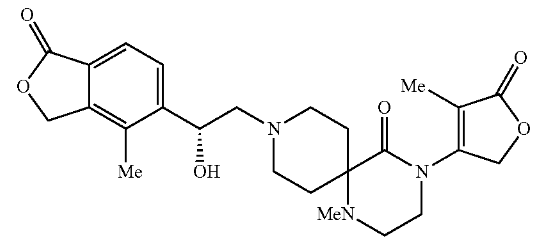 [SMILES: CC1=C(N2CCN(C)C3(CCN(C[C@H](O)c4ccc5c(c4C)COC5=O)CC3)C2=O)COC1=O] | 470 | (R)-9-(2-hydroxy-2-(4-methyl-1-oxo-1,3-dihydroisobenzofuran-5-yl)ethyl)-1-methyl-4-(4-methyl-5-oxo-2,5-dihydrofuran-3-yl)-1,4,9-triazaspiro[5.5]undecan-5-one |
| 35A | 8A, 22 | 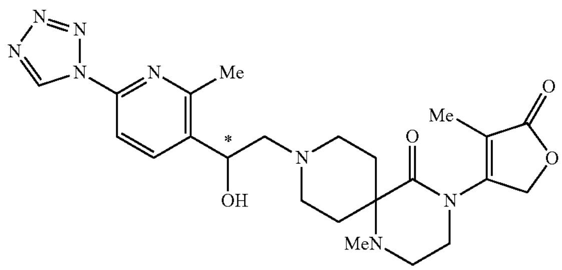 [SMILES: CC1=C(N2CCN(C)C3(CCN(CC(O)c4ccc(-n5cnnn5)nc4C)CC3)C2=O)COC1=O] | 483 | 9-(2-hydroxy-2-(2-methyl-6-(1H-tetrazol-1-yl)pyridin-3-yl)ethyl)-1-methyl-4-(4-methyl-5-oxo-2,5-dihydrofuran-3-yl)-1,4,9-triazaspiro[5.5]undecan-5-one (single diastereomer, absolute stereochemistry not established, but opposite from 35B) |
| 35B | 8B, 22 | 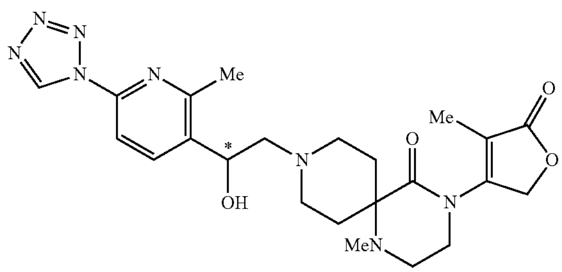 [SMILES: CC1=C(N2CCN(C)C3(CCN(CC(O)c4ccc(-n5cnnn5)nc4C)CC3)C2=O)COC1=O] | 483 | 9-(2-hydroxy-2-(2-methyl-6-(1H-tetrazol-1-yl)pyridin-3-yl)ethyl)-1-methyl-4-(4-methyl-5-oxo-2,5-dihydrofuran-3-yl)-1,4,9-triazaspiro[5.5]undecan-5-one (single diastereomer, absolute stereochemistry not established, but opposite from 35A) |
| 36 | 3B, 37 | 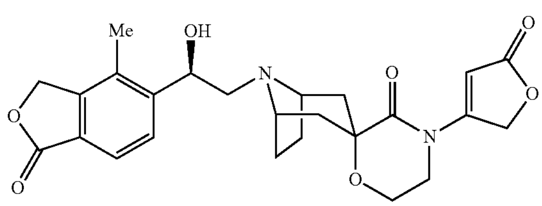 [SMILES: Cc1c([C@@H](O)CN2C3CCC2CC2(C3)OCCN(C3=CC(=O)OC3)C2=O)ccc2c1COC2=O] | 469 | (1R,2'R,5S)-8-((R)-2-hydroxy-2-(4-methyl-1-oxo-1,3-dihydroisobenzofuran-5-yl)ethyl)-4'-(5-oxo-2,5-dihydrofuran-3-yl)-8-azaspiro[bicyclo[3.2.1]octane-3,2'-morpholin]-3'-one |
| 37 | 3B, 25 | 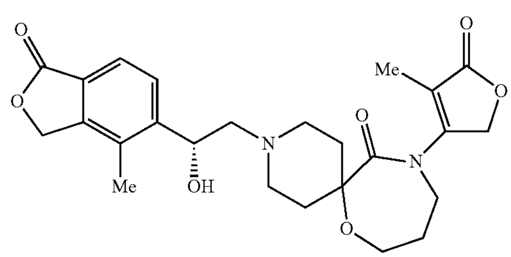 [SMILES: CC1=C(N2CCCOC3(CCN(C[C@H](O)c4ccc5c(c4C)COC5=O)CC3)C2=O)COC1=O] | 471 | (R)-3-(2-hydroxy-2-(4-methyl-1-oxo-1,3-dihydroisobenzofuran-5-yl)ethyl)-11-(4-methyl-5-oxo-2,5-dihydrofuran-3-yl)-7-oxa-3,11-diazaspiro[5.6]dodecan-12-one |
| 38 | 8A, 25 | 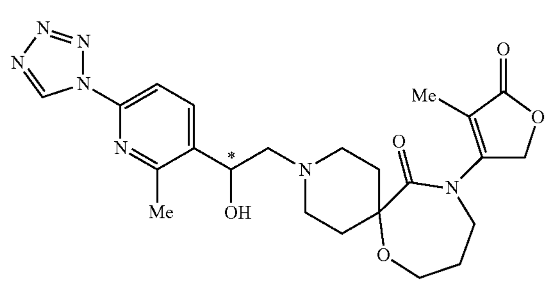 [SMILES: CC1=C(N2CCCOC3(CCN(CC(O)c4ccc(-n5cnnn5)nc4C)CC3)C2=O)COC1=O] | 484 | 3-(2-hydroxy-2-(2-methyl-6-(1H-tetrazol-1-yl)pyridin-3-yl)ethyl)-11-(4-methyl-5-oxo-2,5-dihydrofuran-3-yl)-7-oxa-3,11-diazaspiro[5.6]dodecan-12-one (single diastereomer, absolute stereochemistry not established) |

TABLE 5-continued

| # | Intermediates | Structure | LC-MS M + 1 | IUPAC name |
|---|---|---|---|---|
| 39 | 8A, 24 | 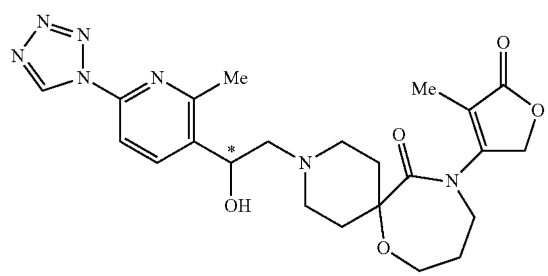 [SMILES: CC1=C(N2CCCOC3(CCN(CC(O)c4ccc(-n5cnnn5)nc4C)CC3)C2=O)COC1=O] | 470 | 9-(2-hydroxy-2-(2-methyl-6-(1H-tetrazol-1-yl)pyridin-3-yl)ethyl)-4-(4-methyl-5-oxo-2,5-dihydrofuran-3-yl)-1-oxa-4,9-diazaspiro[5.5]undecan-5-one |
| 40 | 6A, 27 | 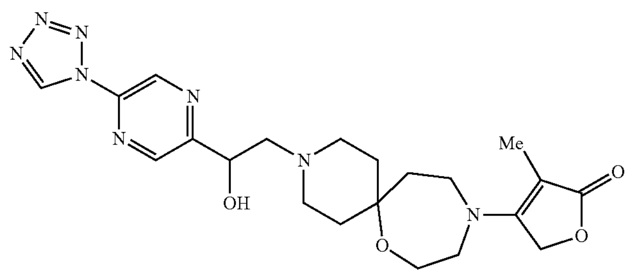 [SMILES: CC1=C(N2CCOC3(CCN(CC(O)c4cnc(-n5cnnn5)cn4)CC3)CC2)COC1=O] | 457 | 4-(3-(2-(5-(1H-tetrazol-1-yl)pyrazin-2-yl)-2-hydroxyethyl)-7-oxa-3,10-diazaspiro[5.6]dodecan-10-yl)-3-methylfuran-2(5H)-one (single diastereomer, absolute stereochemistry not established) |
| 41 | 3B, 27 | 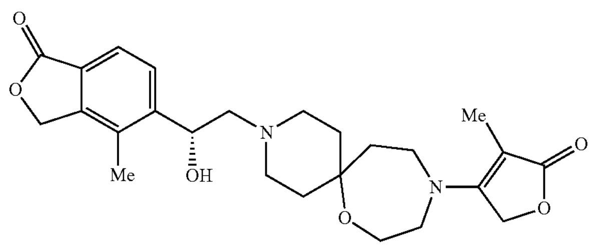 [SMILES: CC1=C(N2CCOC3(CCN(C[C@H](O)c4ccc5c(c4C)COC5=O)CC3)CC2)COC1=O] | 457 | (R)-5-(1-hydroxy-2-(10-(4-methyl-5-oxo-2,5-dihydrofuran-3-yl)-7-oxa-3,10-diazaspiro[5.6]dodecan-3-yl)ethyl)-4-methylisobenzofuran-1(3H)-one (single diastereomer, absolute stereochemistry not established) |
| 42 | 3B, 38 | 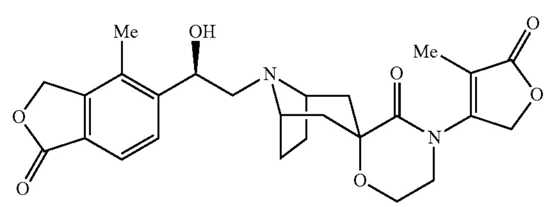 [SMILES: CC1=C(N2CCOC3(CC4CCC(C3)N4C[C@H](O)c3ccc4c(c3C)COC4=O)C2=O)COC1=O] | 483 | (1R,2'R,5S)-8-((R)-2-hydroxy-2-(4-methyl-1-oxo-1,3-dihydroisobenzofuran-5-yl)ethyl)-4'-(4-methyl-5-oxo-2,5-dihydrofuran-3-yl)-8-azaspiro[bicyclo[3.2.1]octane-3,2'-morpholin]-3'-one |
| 43 | 7A, 24 | 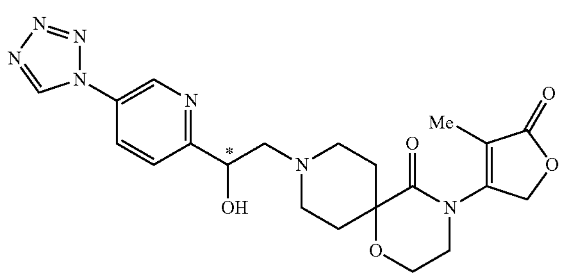 [SMILES: CC1=C(N2CCOC3(CCN(CC(O)c4ccc(-n5cnnn5)cn4)CC3)C2=O)COC1=O] | 456 | 9-(2-(5-(1H-tetrazol-1-yl)pyridin-2-yl)-2-hydroxyethyl)-4-(4-methyl-5-oxo-2,5-dihydrofuran-3-yl)-1-oxa-4,9-diazaspiro[5.5]undecan-5-one (single diastereomer, absolute stereochemistry not established) |
| 44 | 6A, 38 | 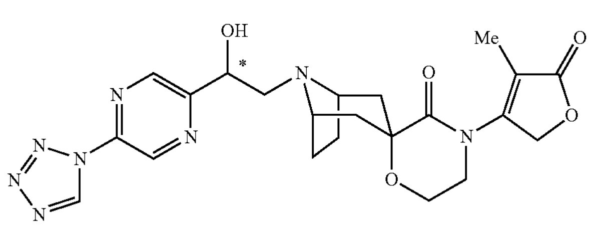 [SMILES: CC1=C(N2CCOC3(CC4CCC(C3)N4CC(O)c3cnc(-n4cnnn4)cn3)C2=O)COC1=O] | 483 | (1R,2'r,5S)-8-(2-(5-(1H-tetrazol-1-yl)pyrazin-2-yl)-2-hydroxyethyl)-4'-(4-methyl-5-oxo-2,5-dihydrofuran-3-yl)-8-azaspiro[bicyclo[3.2.1]octane-3,2'-morpholin]-3'-one (single diastereomer, absolute stereochemistry at hydroxyl center not established) |

TABLE 5-continued

| # | Intermediates | Structure | LC-MS M + 1 | IUPAC name |
|---|---|---|---|---|
| 45A | 9A, 24 | 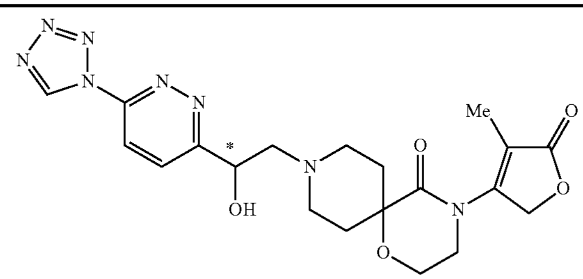 | 457 | 9-(2-(6-(1H-tetrazol-1-yl)pyridazin-3-yl)-2-hydroxyethyl)-4-(4-methyl-5-oxo-2,5-dihydrofuran-3-yl)-1-oxa-4,9-diazaspiro[5.5]undecan-5-one (single diastereomer, absolute stereochemistry not established, but opposite from 45B) |
| 45B | 9B, 24 | 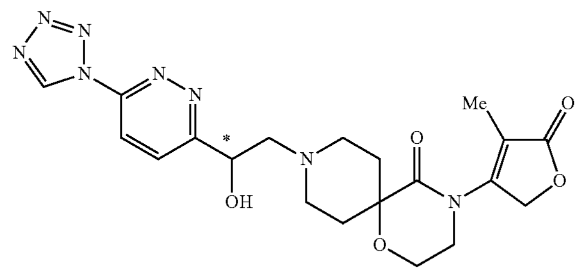 [SMILES: CC1=C(N2CCOC3(CCN(CC(O)c4ccc(-n5cnnn5)nn4)CC3)C2=O)COC1=O] | 457 | 9-(2-(6-(1H-tetrazol-1-yl)pyridazin-3-yl)-2-hydroxyethyl)-4-(4-methyl-5-oxo-2,5-dihydrofuran-3-yl)-1-oxa-4,9-diazaspiro[5.5]undecan-5-one (single diastereomer, absolute stereochemistry not established, but opposite from 45A) |
| 46A | 10A, 24 | 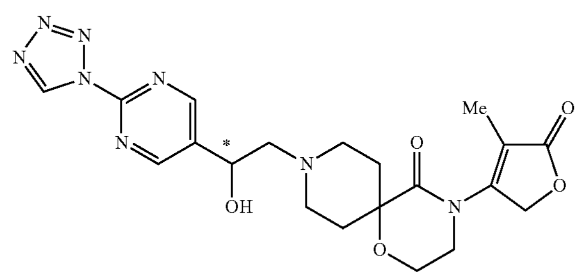 [SMILES: CC1=C(N2CCOC3(CCN(CC(O)c4cnc(-n5cnnn5)nc4)CC3)C2=O)COC1=O] | 457 | 9-(2-(2-(1H-tetrazol-1-yl)pyrimidin-5-yl)-2-hydroxyethyl)-4-(4-methyl-5-oxo-2,5-dihydrofuran-3-yl)-1-oxa-4,9-diazaspiro[5.5]undecan-5-one (single diastereomer, absolute stereochemistry not established, but opposite from 46B) |
| 46B | 10B, 24 | 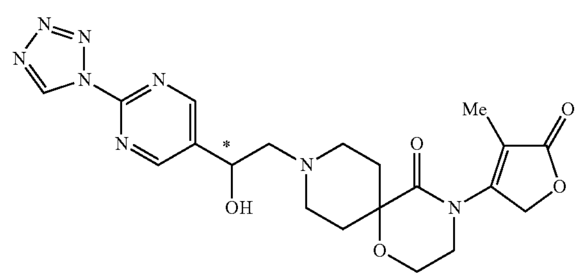 [SMILES: CC1=C(N2CCOC3(CCN(CC(O)c4cnc(-n5cnnn5)nc4)CC3)C2=O)COC1=O] | 457 | 9-(2-(2-(1H-tetrazol-1-yl)pyrimidin-5-yl)-2-hydroxyethyl)-4-(4-methyl-5-oxo-2,5-dihydrofuran-3-yl)-1-oxa-4,9-diazaspiro[5.5]undecan-5-one (single diastereomer, absolute stereochemistry not established, but opposite from 46A) |
| 47 | 5A, 38 | 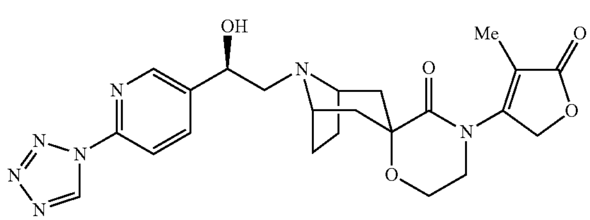 [SMILES: CC1=C(N2CCOC3(CC4CCC(C3)N4C[C@H](O)c3ccc(-n4cnnn4)nc3)C2=O)COC1=O] | 482 | (1R,2'R,5S)-8-((R)-2-(6-(1H-tetrazol-1-yl)pyridin-3-yl)-2-hydroxyethyl)-4'-(4-methyl-5-oxo-2,5-dihydrofuran-3-yl)-8-azaspiro[bicyclo[3.2.1]octane-3,2'-morpholin]-3'-one |
| 48A | 6A, 44 | 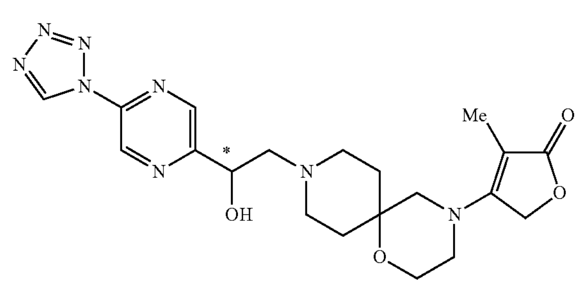 [SMILES: CC1=C(N2CCOC3(CCN(CC(O)c4cnc(-n5cnnn5)cn4)CC3)C2)COC1=O] | 443 | 4-(9-(2-(5-(1H-tetrazol-1-yl)pyrazin-2-yl)-2-hydroxyethyl)-1-oxa-4,9-diazaspiro[5.5]undecan-4-yl)-3-methylfuran-2(5H)-one (single diastereomer, absolute stereochemistry not established) |

TABLE 5-continued

| # | Intermediates | Structure | LC-MS M + 1 | IUPAC name |
|---|---|---|---|---|
| 48B | 6B, 44 | 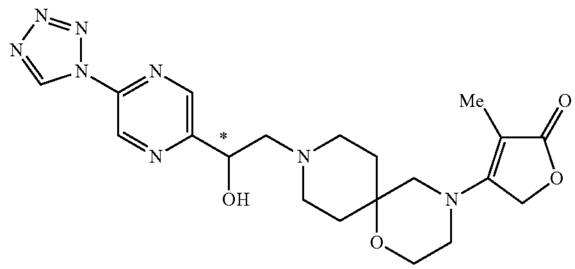 [SMILES: CC1=C(N2CCOC3(CCN(CC(O)c4cnc(-n5cnnn5)cn4)CC3)C2)COC1=O] | 443 | 4-(9-(2-(5-(1H-tetrazol-1-yl)pyrazin-2-yl)-2-hydroxyethyl)-1-oxa-4,9-diazaspiro[5.5]undecan-4-yl)-3-methylfuran-2(5H)-one (single diastereomer, absolute stereochemistry not established, but opposite from 48 A) |

Example 49 (Typical Example for Reductive Amination)

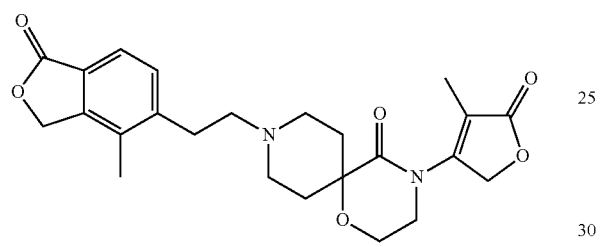

9-(2-(4-methyl-1-oxo-1,3-dihydroisobenzofuran-5-yl)ethyl)-4-(4-methyl-5-oxo-2,5-dihydrofuran-3-yl)-1-oxa-4,9-diazaspiro[5.5]undecan-5-one A mixture of (4-Methyl-1-oxo-1,3-dihydro-2-benzofuran-5-yl)acetaldehyde (Int. 2, 100 mg, crude), 4-(4-methyl-5-oxo-2,5-dihydrofuran-3-yl)-1-oxa-4,9-diazaspiro[5.5]undecan-5-one (Int. 24, 154 mg, 0.58 mmol), and NaBH(OAc)$_3$ (167 mg, 0.79 mmol) in THF (5 mL) was stirred at 50° C. for 3 hours. The mixture was concentrated and the residue was purified by HPLC to give the title compound. LC-MS (ESI, m/z): 441 [M+1]$^+$.

The following compound was prepared in an analagous fashion to that described for 9-(2-(4-methyl-1-oxo-1,3-dihydroisobenzofuran-5-yl)ethyl)-4-(4-methyl-5-oxo-2,5-dihydrofuran-3-yl)-1-oxa-4,9-diazaspiro[5.5]undecan-5-one (immediately above, Example 49) using an aldehyde and amine prepared as described previously.

TABLE 6

| Ex. | Intermediates | Example structure | LC/MS [M + 1]$^+$ | Example Name |
|---|---|---|---|---|
| 50 | 18, 44 | | 426 | 9-(2-(4-methyl-1-oxo-1,3-dihydroisobenzofuran-5-yl)ethyl)-4-(4-methyl-5-oxo-2,5-dihydrofuran-3-yl)-1-oxa-4,9-diazaspiro[5.5]undecan-5-one |

Example 51 Typical Example for Hydroamination

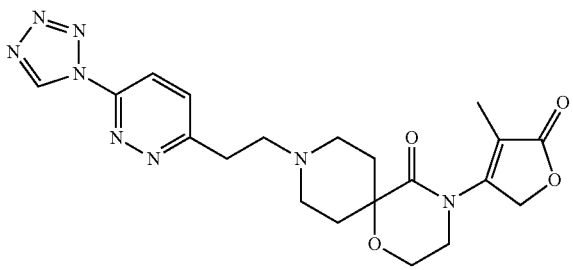 [SMILES: CC1=C(N2CCOC3(CCN(CCc4ccc(-n5cnnn5)nn4)CC3)C2=O)COC1=O]

9-(2-(6-(1H-tetrazol-1-yl)pyridazin-3-yl)ethyl)-4-(4-methyl-5-oxo-2,5-dihydrofuran-3-yl)-1-oxa-4,9-diazaspiro[5.5]undecan-5-one A mixture of 4-(4-methyl-5-oxo-2,5-dihydrofuran-3-yl)-1-oxa-4,9-diazaspiro[5.5]undecan-5-one (Int. 24, 60 mg, 0.22 mmol), 3-(1H-tetrazol-1-yl)-6-vinylpyridazine (Int. 16, 156 mg, 0.88 mmol), DPEPhos (10 mg) and Rh(COD)BF$_4$ (10 mg) in toluene (1 mL) was stirred at 70° C. for 24 h under N$_2$ in a sealed tube. The mixture was then purified via HPLC to afford the title compound. $^1$H-NMR (400 MHz, MeOD) δ ppm 10.15 (s, 1H), 8.38 (d, J=9.4 Hz, 1H), 8.05 (d, J=9.4 Hz, 1H), 5.15 (s, 2H), 3.35-4.15 (m, 12H), 2.30-2.50 (m, 4H), 1.93 (s, 3H). LC-MS (ESI, m/z): 441 [M+1]$^+$.

The following compounds were prepared in an analagous fashion to that described for 9-(2-(6-(1H-tetrazol-1-yl)pyridazin-3-yl)ethyl)-4-(4-methyl-5-oxo-2,5-dihydrofuran-3-yl)-1-oxa-4,9-diazaspiro[5.5]undecan-5-one (immediately above, Example 51) using styrenes and amines prepared as described previously.

TABLE 7

| Ex. | Intermediates | Example structure | LC/MS [M + 1]$^+$ | Example IUPAC Name |
|---|---|---|---|---|
| 52 | 15, 24 | | 441 | 9-(2-(5-(1H-tetrazol-1-yl)pyrazin-2-yl)ethyl)-4-(4-methyl-5-oxo-2,5-dihydrofuran-3-yl)-1-oxa-4,9-diazaspiro[5.5]undecan-5-one |
| 53 | 17, 24 | | 440 | 9-(2-(6-(1H-tetrazol-1-yl)pyridin-3-yl)ethyl)-4-(4-methyl-5-oxo-2,5-dihydrofuran-3-yl)-1-oxa-4,9-diazaspiro[5.5]undecan-5-one |
| 54 | 16, 37 | | 453 | (1R,2'r,5S)-8-(2-(6-(1H-tetrazol-1-yl)pyridazin-3-yl)ethyl)-4'-(5-oxo-2,5-dihydrofuran-3-yl)-8-azaspiro[bicyclo[3.2.1]octane-3,2'-morpholin]-3'-one |

Example 55 Typical Example for Fluorination

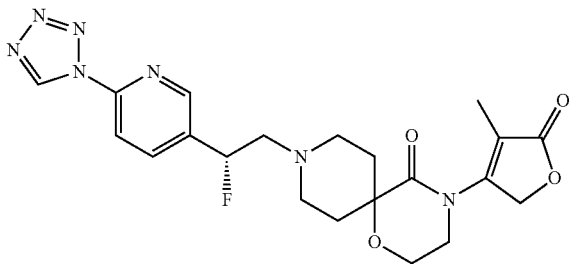 [SMILES: CC1=C(N2CCOC3(CCN(C[C@H](F)c4ccc(-n5cnnn5)nc4)CC3)C2=O)COC1=O]

(R)-9-(2-(6-(1H-tetrazol-1-yl)pyridin-3-yl)-2-fluoro-ethyl)-4-(4-methyl-5-oxo-2,5-dihydrofuran-3-yl)-1-oxa-4,9-diazaspiro[5.5]undecan-5-one To a solution of (S)-9-(2-(6-(1H-tetrazol-1-yl)pyridin-3-yl)-2-hydroxyethyl)-4-(4-methyl-5-oxo-2,5-dihydrofuran-3-yl)-1-oxa-4,9-diazaspiro[5.5]undecan-5-one (Int. 6B, 100 mg, 0.22 mmol) in 5 mL of DCM was added Et$_3$N.3HF (10 drops) and DAST (5 drops) at −78° C. under N$_2$ atmosphere. The mixture was stirred overnight while the temperature rose to room temperature, then quenched with NaHCO$_3$. The organic layer was separated and the aqueous was extracted with DCM. The combined organic layers were dried over anhydrous Na$_2$SO$_4$, filtered and concentrated. The residue was then purified by pre-HPLC to afford the title compound. LC-MS (ESI, m/z): 458 [M+1]$^+$.

The following compounds were prepared in an analagous fashion to that described for (R)-9-(2-(6-(1H-tetrazol-1-yl)pyridin-3-yl)-2-fluoroethyl)-4-(4-methyl-5-oxo-2,5-dihydrofuran-3-yl)-1-oxa-4,9-diazaspiro[5.5]undecan-5-one (immediately above, Example 55).

TABLE 8

| Ex. | Starting material | Example structure | LC/MS [M + 1]$^+$ | Example IUPAC Name |
|---|---|---|---|---|
| 56 | Example 6A | | 458 | (S)-9-(2-(6-(1H-tetrazol-1-yl)pyridin-3-yl)-2-fluoroethyl)-4-(4-methyl-5-oxo-2,5-dihydrofuran-3-yl)-1-oxa-4,9-diazaspiro[5.5]undecan-5-one |
| 57 | Example 8B | | 459 | (R)-9-(2-fluoro-2-(4-methyl-1-oxo-1,3-dihydroisobenzofuran-5-yl)ethyl)-4-(4-methyl-5-oxo-2,5-dihydrofuran-3-yl)-1-oxa-4,9-diazaspiro[5.5]undecan-5-one |
| 58 | Example 8A | | 459 | (S)-9-(2-fluoro-2-(4-methyl-1-oxo-1,3-dihydroisobenzofuran-5-yl)ethyl)-4-(4-methyl-5-oxo-2,5-dihydrofuran-3-yl)-1-oxa-4,9-diazaspiro[5.5]undecan-5-one |

Example 59

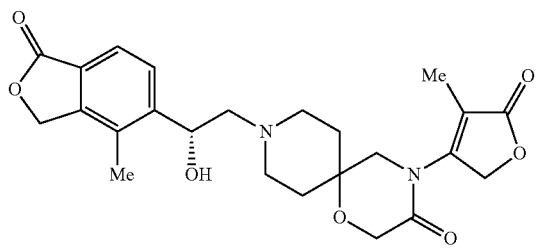 [SMILES: CC1=C(N2CC3(CCN(C[C@H](O)c4ccc5c(c4C)COC5=O)CC3)OCC2=O)COC1=O]

(R)-9-(2-hydroxy-2-(4-methyl-1-oxo-1,3-dihydroisobenzofuran-5-yl)ethyl)-4-(4-methyl-5-oxo-2,5-dihydrofuran-3-yl)-1-oxa-4,9-diazaspiro[5.5]undecan-3-one

Step A: tert-butyl 3-oxo-1-oxa-4,9-diazaspiro[5.5]undecane-9-carboxylate

Chloroacetyl chloride (696 μL, 8.68 mmol) was added dropwise to a solution of commercially available tert-butyl 4-(aminomethyl)-4-hydroxypiperidine-1-carboxylate (2000 mg, 8.68 mmol) and triethylamine (1331 μL, 9.55 mmol) in DCM. After 4 h at rt, the reaction mixture was quenched with water. The aqueous layer was extracted with EtOAc. The organic layer was dried over $Na_2SO_4$, filtered and then evaporated under reduced pressure. The crude material was then dissolved in THF (90 mL) and potassium tert-butoxide (1M, 19.1 mL, 19.1 mmol) was added dropwise at 0° C. The reaction mixture was stirred at rt overnight. The reaction mixture was neutralized by addition of a solution of $NH_4Cl$. The aqueous layer was extracted with EtOAc. The organic layer was then dried, filtered, and evaporated under reduced pressure. The residue was purified by flash chromatography on silica gel to give the title compound.

Step B: 1-oxa-4,9-diazaspiro[5.5]undecan-3-one

To tert-butyl 3-oxo-1-oxa-4,9-diazaspiro[5.5]undecane-9-carboxylate (120 mg, 0.444 mmol) in DCM (2220 μL) was added TFA (684 μL, 8.88 mmol) at 0° C. The reaction mixture was stirred at rt for 1 h. The reaction mixture was concentrated, and azeotroped with DCM/MeOH/toluene to remove as much TFA as possible. Then a 2 g BOND ELUT SCX Ion exchange column was first rinsed with MeOH, the sample loaded with MeOH, washed with MeOH dropwise to remove TFA, and finally, the column was rinsed with 2N NH3/MeOH to get product as free amine after concentration of the eluent.

Step C: (R)-9-(2-hydroxy-2-(4-methyl-1-oxo-1,3-dihydroisobenzofuran-5-yl)ethyl)-1-oxa-4,9-diazaspiro[5.5]undecan-3-one To 1-oxa-4,9-diazaspiro[5.5]undecan-3-one (59.7 mg, 0.351 mmol) in EtOH (1402 μl) was added 4-methyl-5-[(2R)-oxiran-2-yl]-2-benzofuran-1(3H)-one (Int. 3B, 80 mg, 0.421 mmol). The reaction mixture was heated at 90° C. overnight. The reaction mixture was concentrated, and purified by preparative TLC using 4 1000 μM plates (15% MeOH/EA) to give the title compound.

Step D: (R)-9-(2-hydroxy-2-(4-methyl-1-oxo-1,3-dihydroisobenzofuran-5-yl)ethyl)-4-(4-methyl-5-oxo-2,5-dihydrofuran-3-yl)-1-oxa-4,9-diazaspiro[5.5]undecan-3-one To a microwave vial was charged (R)-9-(2-hydroxy-2-(4-methyl-1-oxo-1,3-dihydroisobenzofuran-5-yl)ethyl)-1-oxa-4,9-diazaspiro[5.5]undecan-3-one (30 mg, 0.083 mmol), 4-methyl-5-oxo-2,5-dihydrofuran-3-yl trifluoromethanesulfonate (Int. 4, 24.59 mg, 0.100 mmol), Pd2(dba)3 (3.81 mg, 4.16 μmol), Xantphos (7.22 mg, 0.012 mmol), and $Cs_2CO_3$ (54.2 mg, 0.166 mmol). The vial was sealed, degassed, and filled with new anhydrous dioxane (416 μl). The reaction mixture was heated at 100° C. overnight. The reaction mixture was diluted with EtOAc and DCM, then filtered through CELITE. The crude product was purified by ISCO MPLC (0-10% MeOH/DCM). The product was further purified by preparative TLC (silica, 2000 μM) to afford the title compound. LC/MS: $(M+1)^+$: 457.

Example 60

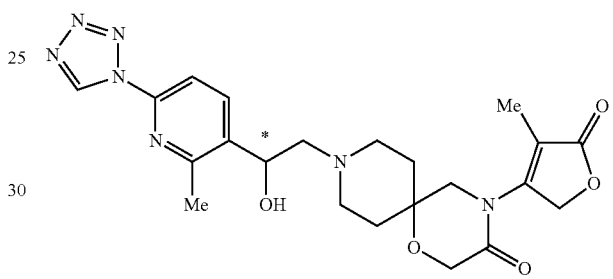

9-(2-hydroxy-2-(2-methyl-6-(1H-tetrazol-1-yl)pyridin-3-yl)ethyl)-4-(4-methyl-5-oxo-2,5-dihydrofuran-3-yl)-1-oxa-4,9-diazaspiro[5.5]undecan-3-one The title compound was prepared in an analagous fashion to that described for (R)-9-(2-hydroxy-2-(4-methyl-1-oxo-1,3-dihydroisobenzofuran-5-yl)ethyl)-4-(4-methyl-5-oxo-2,5-dihydrofuran-3-yl)-1-oxa-4,9-diazaspiro[5.5]undecan-3-one (Example 59, immediately above) except in Step C the faster eluting single enantiomer of 2-methyl-3-(oxiran-2-yl)-6-(1H-tetrazol-1-yl)pyridine (Int. 8A) was used as the epoxide reagent. Thus the product is a single enantiomer. LC/MS: $(M+1)^+$: 470.

The following Thallium Flux Assay and/or the Electrophysiology Assays were performed on each of the final product compounds in the Examples unless otherwise noted.

Thallium Flux Assay

A Thallium Flux Assay was performed on the compounds of the Examples. This assay has been described previously; see, e.g., PCT Published Application WO 2013/062900.

Data collected for compounds in the Examples of the present invention using the Thallium Flux Assay are shown in Table 9 below. All of the tested final product compounds in the Examples (diastereomeric mixtures and individual diastereomers) had $IC_{50}$ potencies less than 1 μM in the Thallium Flux Assay.

Electrophysiology Assay

Blocking of Kir1.1 (ROMK1) currents was examined by whole cell voltage clamp (Hamill et. al. Pfluegers Archives 391:85-100 (1981)) using the IonWorks Quattro automated electrophysiology platform (Molecular Devices, Sunnyvale, Calif.). Chinese hamster ovary cells stably expressing Kir1.1 channels were maintained in T-75 flasks in cell culture media in a humidified 10% $CO_2$ incubator at 37° C. Prior to an experiment, Kir1.1 expression was induced by overnight incubation with 1 mM sodium butyrate. On the day of the experiment, cells were dissociated with 2.5 mL of Versene (Invitrogen 15040-066), a non-enzymatic cell dissociation reagent, for approximately 6 min at 37° C. and suspended in 10 mL of bath solution containing (in mM): 150 NaCl, 10 KCl, 2.7 $CaCl_2$, 0.5 $MgCl_2$, and 5 HEPES, at pH 7.4. After centrifugation, the cell pellet was resuspended in approximately 4.0 mL of bath solution and placed in the IonWorks instrument. The intracellular solution consisted of (in mM): 80 K gluconate, 40 KCl, 20 KF, 3.2 $MgCl_2$, 3 EGTA, and 5 Hepes, at pH 7.4. Electrical access to the cytoplasm was achieved by perforation in 0.13 mg/mL amphotericin B for 4 min. Amphotericin B (Sigma A-4888) was prepared as a 40 mg/mL solution in DMSO.

Voltage protocols and current recordings were performed using the IonWorks HT software/hardware system. Currents were sampled at 1 kHz. There was no correction for liquid junction potentials. The test pulse, consisting of a 100 ms (millisecond) step to 0 mV (millivolts) from a holding potential of −70 mV, followed by a 100 ms voltage ramp from −70 mV to +70 mV, was applied before and after a 6 min compound incubation period. Test compounds were prepared by diluting DMSO stock solutions into the bath solution at 3× the final concentration and placed in the instrument in 96-well polypropylene plates. Current amplitudes were measured using the IonWorks software. To assess compound potency, the fractional block during the voltage step to 0 mV was calculated in Microsoft Excel (Microsoft, Redmond, Calif.), and dose-response curves were fitted with Igor Pro 4.0 (WaveMetrics, Lake Oswego, Oreg.). Although not required, a control compound is typically included to support that the assay is giving consistent results compared to previous measurements. The control can be any compound of Formula I of the present invention, preferably with an $IC_{50}$ potency of less than 1 μM in this assay. Alternatively, the control could be another compound (outside the scope of Formula I) that has an $IC_{50}$ potency in this assay of less than 1 μM.

Data collected for compounds in the Examples of the present invention using the Thallium Flux Assay and the Electrophysiology Assay are shown in Table 9 below. All of the tested final product compounds in the Examples (whether diastereomeric mixture or individual diastereomers) had $IC_{50}$ potencies less than 1 μM in one or both of the Thallium Flux Assay and the Electrophysiology Assay.

TABLE 9 in vitro potency

| EXAMPLE # | Thallium Flux $IC_{50}$ (μM) | Electrophysiology $IC_{50}$ (μM) |
|---|---|---|
| 1 | 0.06873 | |
| 2A | 0.0365 | 0.026 |
| 2B | 0.05619 | |
| 3A | 0.1137 | |
| 3B | 0.1419 | |
| 4A | 0.03817 | 0.046 |
| 4B | 0.06309 | |
| 5A | 0.04254 | |
| 5B | 0.03679 | |
| 6A | 0.01459 | 0.0066 |
| 6B | 0.01206 | 0.0038 |
| 7A | 0.4161 | |
| 7B | 0.6879 | |
| 8A | 0.01332 | 0.0064 |
| 8B | 0.08988 | |
| 9A | 0.01581 | 0.0048 |
| 9B | 0.01231 | |
| 10A | 0.1552 | |
| 10B | 0.3067 | |
| 10C | 0.3168 | |
| 11 | 0.267 | |
| 12 | 0.1612 | |
| 13A | 0.2299 | |
| 13B | 0.4151 | |
| 14 | 0.2639 | |
| 15 | 0.2796 | |
| 16 | 0.3154 | 0.32 |
| 17 | 0.4683 | |
| 18A | 0.0696 | 0.012 |
| 18B | 0.1105 | |
| 19A | 0.08057 | 0.056 |
| 19B | 0.2628 | 0.1 |
| 20A | 0.06146 | 0.037 |
| 20B | 0.2254 | 0.071 |
| 21 | 0.1708 | 0.077 |
| 22A | 0.03398 | 0.011 |
| 22B | 0.1169 | 0.029 |
| 23 | 0.0591 | |
| 24A | 0.01154 | |
| 24B | 0.03446 | |
| 25A | 0.005563 | 0.016 |
| 25B | 0.1056 | |
| 26A | 0.1711 | |
| 27 | 0.06548 | |
| 28A | 0.2241 | |
| 28B | 0.6296 | |
| 29A | 0.2963 | |
| 29B | 0.3197 | |
| 30A | 0.4769 | |
| 30B | 0.07429 | |
| 31A | 0.1259 | |
| 31B | 0.026 | |
| 32A | 0.03736 | |
| 32B | 0.1227 | |
| 33A | 0.03051 | |
| 33B | 0.09186 | |
| 34 | 0.04229 | 0.027 |
| 35A | 0.04178 | |
| 35B | 0.144 | |
| 36 | 0.02935 | 0.01335 |
| 37 | 0.2853 | |
| 38 | 0.5265 | |
| 39 | 0.01119 | 0.013 |
| 40 | 0.1179 | |
| 41 | 0.03221 | |
| 42 | 0.08741 | |
| 43 | 0.03721 | |
| 44 | 0.4781 | |
| 45A | 0.03728 | 0.015 |
| 45B | 0.04462 | 0.02 |
| 46A | 0.05602 | 0.051 |
| 46B | 0.05809 | |
| 47 | 0.009569 | |
| 48A | 0.4621 | |
| 48B | 0.245 | |
| 49 | 0.05245 | |
| 50 | 0.05757 | 0.016 |
| 51 | 0.02678 | 0.0073 |
| 52 | 0.03929 | |
| 53 | 0.0131 | |
| 54 | 0.003759 | |
| 55 | 0.05904 | |
| 56 | 0.04898 | |

TABLE 9-continued in vitro potency

| EXAMPLE # | Thallium Flux IC$_{50}$ (μM) | Electro-physiology IC$_{50}$ (μM) |
|---|---|---|
| 57 | 0.2176 | |
| 58 | 0.3055 | |
| 59 | 0.6969 | |
| 60 | 0.04837 | |

Spontaneously Hypertensive Rat (SHR) Assay

The spontaneously hypertensive rat (SHR) exhibits age-dependent hypertension that does not require administration of exogenous agents to elevate blood pressure nor does it require the use of a high salt diet to elevate blood pressure. Thus it resembles human essential hypertension and provides an opportunity to assess the dose-dependence of novel agents for their ability to lower blood pressure.

Experimental protocols for evaluating blood pressure lowering efficacy of compounds of the present invention in spontaneously hypertensive rats (SHR):

Spontaneously hypertensive rats (SHR, male, 6 months, Charles River) were implanted with a DSI TA 11PA-C40 telemetry device (Data Sciences, Inc., St. Paul, Minn.) under isoflurane or ketamine/metomidine anesthesia. The telemetry unit catheter was inserted into the descending aorta via the femoral artery and the telemetry device was implanted subcutaneously in the left flank area. Animals were allowed to recover from surgery for 14 days before the start of any studies. Blood pressure, heart rate, and activity signals from conscious, freely moving rats were recorded continuously for 30 seconds every 10 minutes. Hydrochlorothiazide (HCTZ) (25 mg/kg/day, oral) was included as a reference diuretic at a dose giving approximately maximal efficacy in SHR. The blood pressure lowering efficacy of compounds of the present invention compared to vehicle control was evaluated following a single oral gavage each day for a typical duration of three to fourteen days. Data were collected as hourly averages, and changes in blood pressure were calculated by subtracting vehicle control baseline data on an hourly basis. Example numbers 5, 7 and 37 were evaluated at oral doses. Once daily (QD) doses at one or more doses within the range of 0.3 to 10 mg/kg resulted in typical reductions in daily (24 h) mean systolic blood pressure ranging from 0.8 to 3.2 kiloPascals (kPa) at the doses used by the last day of the studies.

The Spontaneously Hypertensive Rat Assay is well known and often used in the art as an experimental model simulating human hypertension (see, e.g., Lerman, L. O., et al., *J Lab Clin Med*, 2005; 146:160-173).

While the invention has been described with reference to certain particular embodiments thereof, numerous alternative embodiments will be apparent to those skilled in the art from the teachings described herein. The scope of the claims should not be limited by the specific embodiments set forth in the examples, but should be given the broadest interpretation consistent with the description as a whole. Recitation or depiction of a specific compound in the claims (i.e., a species) without a specific stereoconfiguration designation, or with such a designation for less than all chiral centers, is intended to encompass the racemate, racemic mixtures, each individual enantiomer, a diastereoisomeric mixture and each individual diastereomer of the compound at the non-specified chiral centers where such forms are possible due to the presence of one or more asymmetric centers. All patents, patent applications and publications cited herein are incorporated by reference in their entirety.

What is claimed is:

1. A compound having structural Formula I:

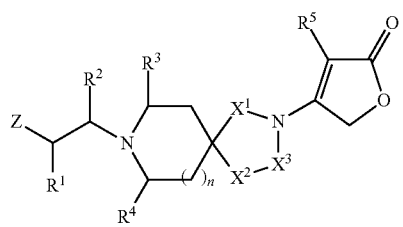

or a pharmaceutically acceptable salt thereof wherein:
$R^1$ is —H, —F, —OH, —C$_{1-3}$alkyl or —OC$_{1-3}$alkyl;
$R^2$ is —H, or C$_{1-4}$alkyl;
$R^3$ is —H, or —C$_{1-3}$alkyl optionally substituted with —OH, —OCH$_3$ or 1 to 3 of —F;
$R^4$ is —H, or —C$_{1-3}$alkyl optionally substituted with —OH, —OCH$_3$ or 1 to 3 of —F;
or $R^3$ and $R^4$ are joined together to form —CH$_2$—CH$_2$—;
n is 1 or 2;
$R^5$ is —H, halo, —C$_{3-6}$cycloalkyl or —C$_{1-3}$alkyl;
$X^1$ is —C(O)—, —CH$_2$—, —CR$^6$R$^7$C(O)—, —CH$_2$CR$^6$R$^7$—, or —CR$^6$R$^7$CH$_2$—;
$X^2$ is —O—, —OCH$_2$— or —N(R);
$X^3$ is —C(O)—, —CH$_2$—, —CR$^6$R$^7$C(O)—, —CH$_2$CR$^6$R$^7$—, or —CR$^6$R$^7$CH$_2$—;
wherein the ring bearing X1, X2 and X3 is a 5-7 membered ring which results in a (i) 11-13-membered spirocyclic core where n is 1, or a (ii) 12-14-membered spirocyclic core where n is 2;
each $R^6$ and $R^7$ is independently —H, halo, —OH, —OC$_{1-3}$alkyl, or —C$_{1-3}$alkyl optionally substituted with —OH, —OCH$_3$ or 1 to 3 of —F;
$R^8$ is —H or —C$_{1-3}$alkyl;
Z is

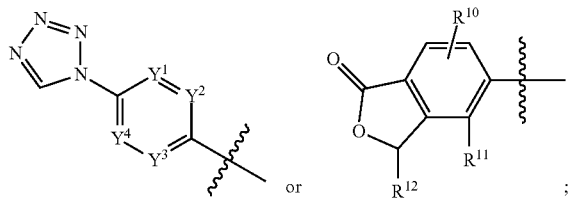

$Y^1$, $Y^2$, $Y^3$ and $Y^4$ are each independently selected from C(R$^9$) or N;
provided that at most two of $Y^1$, $Y^2$, $Y^3$ and $Y^4$ are N;
each $R^9$ is independently —H, halo, C$_{1-4}$alkyl optionally substituted with 1-3 of —F, or OC$_{1-4}$alkyl;
$R^{10}$ is —H, halo, or C$_{1-4}$alkyl optionally substituted with 1-3 of —F;
$R^{11}$ is —H, C$_{1-4}$alkyl optionally substituted with 1-3 of —F, or halo; and
$R^{12}$ is —H or C$_{1-4}$alkyl.

2. The compound of claim 1, or a pharmaceutically acceptable salt thereof, wherein R$^1$ is —H, —F or —OH.

3. The compound of claim 1, or a pharmaceutically acceptable salt thereof, wherein each of $R^3$ and $R^4$ are —H, or $R^3$ and $R^4$ are joined together to form —CH$_2$CH$_2$—.

4. The compound of any of claim 1, or a pharmaceutically acceptable salt thereof, wherein n is 1.

5. The compound of any of claim 1, or a pharmaceutically acceptable salt thereof, wherein $R^5$ is —H, —Cl, —CH$_3$ or cyclopropyl.

6. The compound of any of claim 1, or a pharmaceutically acceptable salt thereof, wherein $R^5$ is —H.

7. The compound of any of claim 1, or a pharmaceutically acceptable salt thereof, wherein $R^5$ is —CH$_3$.

8. The compound of any of claim 1, or a pharmaceutically acceptable salt thereof, wherein $X^1$ is —C(O)—, $X^2$ is —O— and $X^3$ is —CH$_2$CH$_2$—.

9. The compound of any of claim 1 wherein n is 1.

10. The compound of any of claim 1, or a pharmaceutically acceptable salt thereof, wherein $X^1$ is —CH$_2$—, $X^2$ is —O— and $X^3$ is —CH$_2$CH$_2$—.

11. The compound of claim 10 wherein n is 1.

12. The compound of any of claim 1 wherein Z is

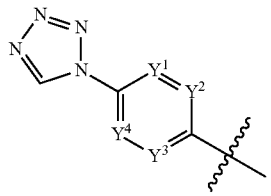

wherein each of the variables $Y^1$, $Y^2$, $Y^3$ and $Y^4$, are as defined in claim 1.

13. The compound of any of claim 1, or a pharmaceutically acceptable salt thereof, wherein Z is

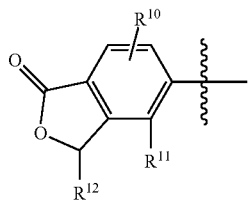

wherein each of the variables $R^{10}$, $R^{11}$ and $R^{12}$ are as defined in claim 1.

14. The compound of any of claim 1, or a pharmaceutically acceptable salt thereof, wherein Z is

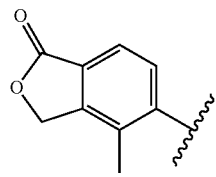

15. A compound which is:
9-[(2R)-2-hydroxy-2-(4-methyl-1-oxo-1,3-dihydro-2-benzofuran-5-yl)ethyl]-4-(4-methyl-5-oxo-2,5-dihydrofuran-3-yl)-1,4,9-triazaspiro[5.5]undecan-5-one dihydrochloride;

9-(2-hydroxy-2-(2-methyl-6-(1H-tetrazol-1-yl)pyridin-3-yl)ethyl)-4-(4-methyl-5-oxo-2,5-dihydrofuran-3-yl)-1,4,9-triazaspiro[5.5]undecan-5-one;

9-(2-(5-(1H-tetrazol-1-yl)pyrazin-2-yl)-2-hydroxyethyl)-4-(4-methyl-5-oxo-2,5-dihydrofuran-3-yl)-1,4,9-triazaspiro[5.5]undecan-5-one;

(R)-9-(2-(6-(1H-tetrazol-1-yl)pyridin-3-yl)-2-hydroxyethyl)-4-(4-methyl-5-oxo-2,5-dihydrofuran-3-yl)-1,4,9-triazaspiro[5.5]undecan-5-one;

(S)-9-(2-(6-(1H-tetrazol-1-yl)pyridin-3-yl)-2-hydroxyethyl)-4-(4-methyl-5-oxo-2,5-dihydrofuran-3-yl)-1,4,9-triazaspiro[5.5]undecan-5-one;

9-(2-(4-(1H-tetrazol-1-yl)phenyl)-2-hydroxyethyl)-4-(4-methyl-5-oxo-2,5-dihydrofuran-3-yl)-1,4,9-triazaspiro[5.5]undecan-5-one;

(R)-9-(2-(6-(1H-tetrazol-1-yl)pyridin-3-yl)-2-hydroxyethyl)-4-(4-methyl-5-oxo-2,5-dihydrofuran-3-yl)-1-oxa-4,9-diazaspiro[5.5]undecan-5-one;

(S)-9-(2-(6-(1H-tetrazol-1-yl)pyridin-3-yl)-2-hydroxyethyl)-4-(4-methyl-5-oxo-2,5-dihydrofuran-3-yl)-1-oxa-4,9-diazaspiro[5.5]undecan-5-one;

(R)-4-(9-(2-(6-(1H-tetrazol-1-yl)pyridin-3-yl)-2-hydroxyethyl)-2,2-difluoro-1-oxa-4,9-diazaspiro[5.5]undecan-4-yl)-3-methylfuran-2(5H)-one;

(S)-4-(9-(2-(6-(1H-tetrazol-1-yl)pyridin-3-yl)-2-hydroxyethyl)-2,2-difluoro-1-oxa-4,9-diazaspiro[5.5]undecan-4-yl)-3-methylfuran-2(5H)-one;

(R)-9-(2-hydroxy-2-(4-methyl-1-oxo-1,3-dihydroisobenzofuran-5-yl)ethyl)-4-(4-methyl-5-oxo-2,5-dihydrofuran-3-yl)-1-oxa-4,9-diazaspiro[5.5]undecan-5-one;

(S)-9-(2-hydroxy-2-(4-methyl-1-oxo-1,3-dihydroisobenzofuran-5-yl)ethyl)-4-(4-methyl-5-oxo-2,5-dihydrofuran-3-yl)-1-oxa-4,9-diazaspiro[5.5]undecan-5-one;

9-(2-(4-(1H-tetrazol-1-yl)phenyl)-2-hydroxyethyl)-4-(4-methyl-5-oxo-2,5-dihydrofuran-3-yl)-1-oxa-4,9-diazaspiro[5.5]undecan-5-one;

9-((S)-2-(6-(1H-tetrazol-1-yl)pyridin-3-yl)-2-hydroxyethyl)-3-methyl-4-(4-methyl-5-oxo-2,5-dihydrofuran-3-yl)-1-oxa-4,9-diazaspiro[5.5]undecan-5-one;

9-((R)-2-(6-(1H-tetrazol-1-yl)pyridin-3-yl)-2-hydroxyethyl)-3-methyl-4-(4-methyl-5-oxo-2,5-dihydrofuran-3-yl)-1-oxa-4,9-diazaspiro[5.5]undecan-5-one;

9-((R)-2-hydroxy-2-(4-methyl-1-oxo-1,3-dihydroisobenzofuran-5-yl)ethyl)-3-methyl-4-(4-methyl-5-oxo-2,5-dihydrofuran-3-yl)-1-oxa-4,9-diazaspiro[5.5]undecan-5-one;

(R)-9-(2-(6-(1H-tetrazol-1-yl)pyridin-3-yl)-2-hydroxyethyl)-4-(5-oxo-2,5-dihydrofuran-3-yl)-1-oxa-4,9-diazaspiro[5.5]undecan-5-one;

9-((S)-2-(6-(1H-tetrazol-1-yl)pyridin-3-yl)-2-hydroxyethyl)-3-methyl-4-(5-oxo-2,5-dihydrofuran-3-yl)-1-oxa-4,9-diazaspiro[5.5]undecan-5-one;

9-((R)-2-(6-(1H-tetrazol-1-yl)pyridin-3-yl)-2-hydroxyethyl)-3-methyl-4-(5-oxo-2,5-dihydrofuran-3-yl)-1-oxa-4,9-diazaspiro[5.5]undecan-5-one;

9-((R)-2-hydroxy-2-(4-methyl-1-oxo-1,3-dihydroisobenzofuran-5-yl)ethyl)-3-methyl-4-(5-oxo-2,5-dihydrofuran-3-yl)-1-oxa-4,9-diazaspiro[5.5]undecan-5-one;

9-((S)-2-(6-(1H-tetrazol-1-yl)pyridin-3-yl)-2-hydroxyethyl)-4-(4-methyl-5-oxo-2,5-dihydrofuran-3-yl)-1-oxa-4,9-diazaspiro[5.6]dodecan-5-one;

(R)-8-(2-hydroxy-2-(4-methyl-1-oxo-1,3-dihydroisobenzofuran-5-yl)ethyl)-3-(5-oxo-2,5-dihydrofuran-3-yl)-1-oxa-3,8-diazaspiro[4.5]decan-2-one;

8-(2-hydroxy-2-(2-methyl-6-(1H-tetrazol-1-yl)pyridin-3-yl)ethyl)-3-(5-oxo-2,5-dihydrofuran-3-yl)-1-oxa-3,8-diazaspiro[4.5]decan-2-one;

9-(2-(5-(1H-tetrazol-1-yl)pyrazin-2-yl)-2-hydroxyethyl)-4-(4-methyl-5-oxo-2,5-dihydrofuran-3-yl)-1-oxa-4,9-diazaspiro[5.5]undecan-5-one;

(R)-4-(9-(2-(6-(1H-tetrazol-1-yl)pyridin-3-yl)-2-hydroxyethyl)-1-oxa-4,9-diazaspiro[5.5]undecan-4-yl)furan-2(5H)-one;

(S)-4-(9-(2-(6-(1H-tetrazol-1-yl)pyridin-3-yl)-2-hydroxyethyl)-1-oxa-4,9-diazaspiro[5.5]undecan-4-yl)furan-2(5H)-one;

4-(9-(2-hydroxy-2-(2-methyl-6-(1H-tetrazol-1-yl)pyridin-3-yl)ethyl)-1-oxa-4,9-diazaspiro[5.5]undecan-4-yl)furan-2(5H)-one;

(R)-5-(1-hydroxy-2-(4-(4-methyl-5-oxo-2,5-dihydrofuran-3-yl)-1-oxa-4,9-diazaspiro[5.5]undecan-9-yl)ethyl)-4-methylisobenzofuran-1(3H)-one;

4-(9-(2-hydroxy-2-(2-methyl-6-(1H-tetrazol-1-yl)pyridin-3-yl)ethyl)-1-oxa-4,9-diazaspiro[5.5]undecan-4-yl)-3-methylfuran-2(5H)-one;

(R)-5-(2-(4-(4-chloro-5-oxo-2,5-dihydrofuran-3-yl)-1-oxa-4,9-diazaspiro[5.5]undecan-9-yl)-1-hydroxyethyl)-4-methylisobenzofuran-1(3H)-one;

(R)-4-(9-(2-(6-(1H-tetrazol-1-yl)pyridin-3-yl)-2-hydroxyethyl)-1-oxa-4,9-diazaspiro[5.5]undecan-4-yl)furan-2(5H)-one;

(S)-4-(9-(2-(6-(1H-tetrazol-1-yl)pyridin-3-yl)-2-hydroxyethyl)-1-oxa-4,9-diazaspiro[5.5]undecan-4-yl)-3-chlorofuran-2(5H)-one;

3-chloro-4-(9-(2-hydroxy-2-(2-methyl-6-(1H-tetrazol-1-yl)pyridin-3-yl)ethyl)-1-oxa-4,9-diazaspiro[5.5]undecan-4-yl)furan-2(5H)-one;

(R)-9-(2-(6-(1H-tetrazol-1-yl)pyridin-3-yl)-2-hydroxyethyl)-3-(5-oxo-2,5-dihydrofuran-3-yl)-1-oxa-3,9-diazaspiro[5.5]undecan-2-one;

9-(2-hydroxy-2-(2-methyl-6-(1H-tetrazol-1-yl)pyridin-3-yl)ethyl)-3-(5-oxo-2,5-dihydrofuran-3-yl)-1-oxa-3,9-diazaspiro[5.5]undecan-2-one;

(R)-4-(9-(2-(6-(1H-tetrazol-1-yl)pyridin-3-yl)-2-hydroxyethyl)-1-oxa-4,9-diazaspiro[5.5]undecan-4-yl)-3-cyclopropylfuran-2(5H)-one;

(S)-4-(9-(2-(6-(1H-tetrazol-1-yl)pyridin-3-yl)-2-hydroxyethyl)-1-oxa-4,9-diazaspiro[5.5]undecan-4-yl)-3-cyclopropylfuran-2(5H)-one;

3-cyclopropyl-4-(9-(2-hydroxy-2-(2-methyl-6-(1H-tetrazol-1-yl)pyridin-3-yl)ethyl)-1-oxa-4,9-diazaspiro[5.5]undecan-4-yl)furan-2(5H)-one;

4-(9-(2-hydroxy-2-(2-methyl-4-(1H-tetrazol-1-yl)phenyl)ethyl)-1-oxa-4,9-diazaspiro[5.5]undecan-4-yl)furan-2(5H)-one;

4-(9-(2-hydroxy-2-(2-methyl-4-(1H-tetrazol-1-yl)phenyl)ethyl)-1-oxa-4,9-diazaspiro[5.5]undecan-4-yl)-3-methylfuran-2(5H)-one;

4-(9-(2-(2-fluoro-4-(1H-tetrazol-1-yl)phenyl)-2-hydroxyethyl)-1-oxa-4,9-diazaspiro[5.5]undecan-4-yl)-3-methylfuran-2(5H)-one;

4-(9-(2-hydroxy-2-(2-methoxy-4-(1H-tetrazol-1-yl)phenyl)ethyl)-1-oxa-4,9-diazaspiro[5.5]undecan-4-yl)-3-methylfuran-2(5H)-one;

(R)-9-(2-hydroxy-2-(4-methyl-1-oxo-1,3-dihydroisobenzofuran-5-yl)ethyl)-1-methyl-4-(4-methyl-5-oxo-2,5-dihydrofuran-3-yl)-1,4,9-triazaspiro[5.5]undecan-5-one;

9-(2-hydroxy-2-(2-methyl-6-(1H-tetrazol-1-yl)pyridin-3-yl)ethyl)-1-methyl-4-(4-methyl-5-oxo-2,5-dihydrofuran-3-yl)-1,4,9-triazaspiro[5.5]undecan-5-one;

(1R,2'R,5S)-8-((R)-2-hydroxy-2-(4-methyl-1-oxo-1,3-dihydroisobenzofuran-5-yl)ethyl)-4'-(5-oxo-2,5-dihydrofuran-3-yl)-8-azaspiro[bicyclo[3.2.1]octane-3,2'-morpholin]-3'-one;

(R)-3-(2-hydroxy-2-(4-methyl-1-oxo-1,3-dihydroisobenzofuran-5-yl)ethyl)-11-(4-methyl-5-oxo-2,5-dihydrofuran-3-yl)-7-oxa-3,11-diazaspiro[5.6]dodecan-12-one;

3-(2-hydroxy-2-(2-methyl-6-(1H-tetrazol-1-yl)pyridin-3-yl)ethyl)-11-(4-methyl-5-oxo-2,5-dihydrofuran-3-yl)-7-oxa-3,11-diazaspiro[5.6]dodecan-12-one;

9-(2-hydroxy-2-(2-methyl-6-(1H-tetrazol-1-yl)pyridin-3-yl)ethyl)-4-(4-methyl-5-oxo-2,5-dihydrofuran-3-yl)-1-oxa-4,9-diazaspiro[5.5]undecan-5-one;

4-(3-(2-(5-(1H-tetrazol-1-yl)pyrazin-2-yl)-2-hydroxyethyl)-7-oxa-3,10-diazaspiro[5.6]dodecan-10-yl)-3-methylfuran-2(5H)-one;

(R)-5-(1-hydroxy-2-(10-(4-methyl-5-oxo-2,5-dihydrofuran-3-yl)-7-oxa-3,10-diazaspiro[5.6]dodecan-3-yl)ethyl)-4-methylisobenzofuran-1(3H)-one;

(1R,2'R,5S)-8-((R)-2-hydroxy-2-(4-methyl-1-oxo-1,3-dihydroisobenzofuran-5-yl)ethyl)-4'-(4-methyl-5-oxo-2,5-dihydrofuran-3-yl)-8-azaspiro[bicyclo[3.2.1]octane-3,2'-morpholin]-3'-one;

9-(2-(5-(1H-tetrazol-1-yl)pyridin-2-yl)-2-hydroxyethyl)-4-(4-methyl-5-oxo-2,5-dihydrofuran-3-yl)-1-oxa-4,9-diazaspiro[5.5]undecan-5-one;

(1R,2'r,5S)-8-(2-(5-(1H-tetrazol-1-yl)pyrazin-2-yl)-2-hydroxyethyl)-4'-(4-methyl-5-oxo-2,5-dihydrofuran-3-yl)-8-azaspiro[bicyclo[3.2.1]octane-3,2'-morpholin]-3'-one;

9-(2-(6-(1H-tetrazol-1-yl)pyridazin-3-yl)-2-hydroxyethyl)-4-(4-methyl-5-oxo-2,5-dihydrofuran-3-yl)-1-oxa-4,9-diazaspiro[5.5]undecan-5-one;

9-(2-(2-(1H-tetrazol-1-yl)pyrimidin-5-yl)-2-hydroxyethyl)-4-(4-methyl-5-oxo-2,5-dihydrofuran-3-yl)-1-oxa-4,9-diazaspiro[5.5]undecan-5-one;

(1R,2'R,5S)-8-((R)-2-(6-(1H-tetrazol-1-yl)pyridin-3-yl)-2-hydroxyethyl)-4'-(4-methyl-5-oxo-2,5-dihydrofuran-3-yl)-8-azaspiro[bicyclo[3.2.1]octane-3,2'-morpholin]-3'-one;

4-(9-(2-(5-(1H-tetrazol-1-yl)pyrazin-2-yl)-2-hydroxyethyl)-1-oxa-4,9-diazaspiro[5.5]undecan-4-yl)-3-methylfuran-2(5H)-one;

9-(2-(4-methyl-1-oxo-1,3-dihydroisobenzofuran-5-yl)ethyl)-4-(4-methyl-5-oxo-2,5-dihydrofuran-3-yl)-1-oxa-4,9-diazaspiro[5.5]undecan-5-one;

9-(2-(4-methyl-1-oxo-1,3-dihydroisobenzofuran-5-yl)ethyl)-4-(4-methyl-5-oxo-2,5-dihydrofuran-3-yl)-1-oxa-4,9-diazaspiro[5.5]undecan-5-one;

9-(2-(6-(1H-tetrazol-1-yl)pyridazin-3-yl)ethyl)-4-(4-methyl-5-oxo-2,5-dihydrofuran-3-yl)-1-oxa-4,9-diazaspiro[5.5]undecan-5-one;

9-(2-(5-(1H-tetrazol-1-yl)pyrazin-2-yl)ethyl)-4-(4-methyl-5-oxo-2,5-dihydrofuran-3-yl)-1-oxa-4,9-diazaspiro[5.5]undecan-5-one;

9-(2-(6-(1H-tetrazol-1-yl)pyridin-3-yl)ethyl)-4-(4-methyl-5-oxo-2,5-dihydrofuran-3-yl)-1-oxa-4,9-diazaspiro[5.5]undecan-5-one;

(1R,2'r,5S)-8-(2-(6-(1H-tetrazol-1-yl)pyridazin-3-yl)ethyl)-4'-(5-oxo-2,5-dihydrofuran-3-yl)-8-azaspiro[bicyclo[3.2.1]octane-3,2'-morpholin]-3'-one;

(R)-9-(2-(6-(1H-tetrazol-1-yl)pyridin-3-yl)-2-fluoroethyl)-4-(4-methyl-5-oxo-2,5-dihydrofuran-3-yl)-1-oxa-4,9-diazaspiro[5.5]undecan-5-one;

(S)-9-(2-(6-(1H-tetrazol-1-yl)pyridin-3-yl)-2-fluoro-ethyl)-4-(4-methyl-5-oxo-2,5-dihydrofuran-3-yl)-1-oxa-4,9-diazaspiro[5.5]undecan-5-one;

(R)-9-(2-fluoro-2-(4-methyl-1-oxo-1,3-dihydroisobenzofuran-5-yl)ethyl)-4-(4-methyl-5-oxo-2,5-dihydrofuran-3-yl)-1-oxa-4,9-diazaspiro[5.5]undecan-5-one;

(S)-9-(2-fluoro-2-(4-methyl-1-oxo-1,3-dihydroisobenzofuran-5-yl)ethyl)-4-(4-methyl-5-oxo-2,5-dihydrofuran-3-yl)-1-oxa-4,9-diazaspiro[5.5]undecan-5-one;

(R)-9-(2-hydroxy-2-(4-methyl-1-oxo-1,3-dihydroisobenzofuran-5-yl)ethyl)-4-(4-methyl-5-oxo-2,5-dihydrofuran-3-yl)-1-oxa-4,9-diazaspiro[5.5]undecan-3-one;

9-(2-hydroxy-2-(2-methyl-6-(1H-tetrazol-1-yl)pyridin-3-yl)ethyl)-4-(4-methyl-5-oxo-2,5-dihydrofuran-3-yl)-1-oxa-4,9-diazaspiro[5.5]undecan-3-one;

or a pharmaceutically acceptable salt thereof.

16. A pharmaceutical composition comprising a compound of one of claim 1 or a pharmaceutically acceptable salt thereof and a pharmaceutically acceptable carrier.

17. The pharmaceutical composition of claim 16 further comprising an additional active agent selected from losartan, valsartan, candesartan, olmesartan, telmesartan, eprosartan, irbesartan, amlodipine, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril, amiloride, spironolactone, epleranone or triamterene, or a pro-drug thereof, or a pharmaceutically acceptable salt of any of the foregoing.

18. A method for inhibiting ROMK comprising administering a compound of one of claim 1 or a pharmaceutically acceptable salt thereof in a ROMK-inhibitory effective amount to a patient in need thereof.

19. A method for causing diueresis, natriuresis or both, comprising administering a compound of one of claim 1 or a pharmaceutically acceptable salt thereof in a therapeutically effective amount to a patient in need thereof.

20. A method for the treatment of one or more disorders selected from hypertension, acute heart failure, chronic heart failure, pulmonary arterial hypertension, cardiovascular disease, diabetes, endothelial dysfunction, diastolic dysfunction, stable and unstable angina pectoris, thromboses, restenosis, myocardial infarction, stroke, cardiac insufficiency, pulmonary hypertonia, atherosclerosis, hepatic cirrhosis, ascites, pre-eclampsia, cerebral edema, nephropathy, nephrotic syndrome, acute kidney insufficiency, chronic kidney disease, hypercalcemia, Dent's disease, Meniere's disease, or edematous states comprising administering a compound of one of claim 1 or a pharmaceutically acceptable salt thereof in a therapeutically effective amount to a patient in need thereof.

* * * * *

UNITED STATES PATENT AND TRADEMARK OFFICE
CERTIFICATE OF CORRECTION

PATENT NO. : 9,850,245 B2  
APPLICATION NO. : 15/505277  
DATED : December 26, 2017  
INVENTOR(S) : Alexander Pasternak et al.

Page 1 of 1

It is certified that error appears in the above-identified patent and that said Letters Patent is hereby corrected as shown below:

In the Claims

Claim 1, Column 119, Line 33:
Replace "X2 is –O–, –OCH2– or –N(R)" with "X2 is –O–, –OCH2– or –N(R8)".

Signed and Sealed this
Twenty-eighth Day of April, 2020

Andrei Iancu
*Director of the United States Patent and Trademark Office*